US011510996B2

(12) United States Patent
Pearson et al.

(10) Patent No.: US 11,510,996 B2
(45) Date of Patent: Nov. 29, 2022

(54) COVALENT POLYMER-ANTIGEN CONJUGATED PARTICLES

(71) Applicants: COUR PHARMACEUTICALS DEVELOPMENT COMPANY, INC., Northbrook, IL (US); THE REGENTS OF THE UNIVERSITY OF MICHIGAN, Ann Arbor, MI (US)

(72) Inventors: Ryan Pearson, Baltimore, MD (US); Daniel Getts, Northbrook, IL (US); John Puisis, Northbrook, IL (US); James Herrmann, Northbrook, IL (US); Lonnie D. Shea, Ann Arbor, MI (US)

(73) Assignees: COUR PHARMACEUTICALS DEVELOPMENT COMPANY INC., Northbrook, IL (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/064,528

(22) PCT Filed: Dec. 22, 2016

(86) PCT No.: PCT/US2016/068423
§ 371 (c)(1),
(2) Date: Jun. 21, 2018

(87) PCT Pub. No.: WO2017/112899
PCT Pub. Date: Jun. 29, 2017

(65) Prior Publication Data
US 2019/0282707 A1 Sep. 19, 2019

Related U.S. Application Data

(60) Provisional application No. 62/387,183, filed on Dec. 23, 2015, provisional application No. 62/292,098, filed on Feb. 5, 2016.

(51) Int. Cl.
A61K 39/00 (2006.01)
A61K 47/69 (2017.01)
A61P 37/06 (2006.01)
A61K 39/385 (2006.01)
A61K 9/00 (2006.01)
A61K 9/51 (2006.01)

(52) U.S. Cl.
CPC ...... A61K 47/6937 (2017.08); A61K 39/0008 (2013.01); A61K 39/385 (2013.01); A61K 47/6933 (2017.08); A61P 37/06 (2018.01); A61K 9/0019 (2013.01); A61K 9/5153 (2013.01); A61K 2039/577 (2013.01); A61K 2039/6093 (2013.01)

(58) Field of Classification Search
CPC ............... A61K 39/00; A61K 39/0001; A61K 39/0002; A61K 39/0005; A61K 39/0008; A61K 39/001
See application file for complete search history.

(56) References Cited

U.S. PATENT DOCUMENTS

| | | |
|---|---|---|
| 4,751,180 A | 6/1988 | Cousens et al. |
| 4,935,233 A | 6/1990 | Bell et al. |
| 6,281,256 B1 | 8/2001 | Harris et al. |
| 6,797,738 B2 | 9/2004 | Harris et al. |
| 6,890,556 B1 | 5/2005 | Segura et al. |
| 7,029,697 B2 | 4/2006 | Segura et al. |
| 7,427,602 B1 | 9/2008 | Shea et al. |
| 7,846,466 B2 | 12/2010 | Shea et al. |
| 8,476,228 B2 | 7/2013 | Kodra et al. |
| 2002/0045672 A1 | 4/2002 | Harris et al. |
| 2005/0090008 A1 | 4/2005 | Segura et al. |
| 2006/0002978 A1 | 1/2006 | Shea et al. |
| 2009/0238879 A1 | 9/2009 | Shea et al. |
| 2010/0129439 A1* | 5/2010 | Alexis ............... A61K 39/00 424/451 |
| 2010/0233251 A1* | 9/2010 | Von Andrian ......... A61K 39/00 424/450 |
| 2011/0293644 A1 | 12/2011 | Anderson et al. |
| 2012/0076831 A1 | 3/2012 | Miller et al. |
| 2015/0190485 A1 | 7/2015 | Shea et al. |
| 2015/0209293 A1* | 7/2015 | Shea ................... A61K 9/127 424/451 |

(Continued)

FOREIGN PATENT DOCUMENTS

| | | |
|---|---|---|
| WO | WO-93/16724 A1 | 9/1993 |
| WO | WO-94/27634 A1 | 12/1994 |

(Continued)

OTHER PUBLICATIONS

Arano et al., A novel bifunctional metabolizable linker for the conjugation of antibodies with radionuclides, Bioconjug. Chem., 2(2):71-6 (Mar.-Apr. 1991).

(Continued)

Primary Examiner — Micah Paul Young
(74) Attorney, Agent, or Firm — Marshall, Gerstein & Borun LLP

(57) ABSTRACT

The present invention provides compositions comprising tolerizing immune modified particles (TIMPs) and methods for using and making said TIMPs. In particular, carrier polymer is covalently conjugated with antigenic peptide before particle formation, which allows for exquisite control of particle size and antigen encapsulation (e.g., for use in eliciting induction of immunological tolerance).

18 Claims, 24 Drawing Sheets
Specification includes a Sequence Listing.

(56) References Cited

U.S. PATENT DOCUMENTS

2016/0166664 A1    6/2016    Miller et al.

FOREIGN PATENT DOCUMENTS

| WO | WO-2010/085509 A1 | 7/2010 |
| WO | WO-2013/192532 A2 | 12/2013 |
| WO | WO-2015/023796 A2 | 2/2015 |

OTHER PUBLICATIONS

Astete et al., Synthesis and characterization of PLGA nanoparticles, J. Biomater. Sci. Polym. Ed., 17(3):247-89 (2006).

Bach et al., Tolerance to islet autoantigens in type 1 diabetes, Annu. Rev. Immunol., 19:131-61 (2001).

Ben-Nun et al., The rapid isolation of clonable antigen-specific T lymphocyte lines capable of mediating autoimmune encephalomyelitis, Eur. J. Immunol., 11(3):195-9 (1981).

Bruchez et al., Semiconductor nanocrystals as fluorescent biological labels, Science, 281 (5385):2013-6 (1998).

Brus, A simple model for the ionization potential, electron affinity, and aqueous redox potentials of small semiconductor crystallites, J. Chem. Physics, 79 (11): 5566 (1983).

Chao et al., Molecular characterization of MHC class II antigens (β1 domain) in the BB diabetes-prone and -resistant rat, Immunogenetics, 29(4):231-4 (Jul. 1989).

Choy, Oral toleragens in rheumatoid arthritis, Curr. Opin. Investig. Drugs, 1(1):58-62 (Sep. 2000).

Etienne et al., Third-order nonlinear optical properties of a cadmiun sulfide-dendrimer nanocomposite, Appl. Phys. Lett., 87:181913 (2005).

Getts et al., Ly6c+ "inflammatory monocytes" are microglial precursors recruited in a pathogenic manner in West Nile virus encephalitis, J. Exp. Med., 205(10):2319-37 (Sep. 2008).

Iglesias et al., T- and B-cell responses to myelin oligodendrocyte glycoprotein in experimental autoimmune encephalomyelitis and multiple sclerosis, Glia, 36(2):220-34 (Nov. 2001).

International Application No. PCT/US2016/068423, International Preliminary Report on Patentability, dated Jun. 26, 2018.

International Application No. PCT/US2016/068423, International Search Report and Written Opinion, dated Apr. 24, 2017.

Joumaa et al., Synthesis of quantum dot-tagged submicrometer polystyrene particles by miniemulsion polymerization, Langmuir, 22(4):1810-6 (2006).

Kang et al., Transactivation by AP-1 is a molecular target of T cell clonal anergy, Science, 257(5073):1134-8 (1992).

Lemon et al., Preparation and Characterization of Dendrimer-Encapsulated CdS Semiconductor Quantum Dots, J. Am. Chem. Soc., 122(51):12886-7 (2000).

Maratea et al., Deletion and fusion analysis of the phage phi X174 lysis gene E, Gene, 40(1):39-46 (1985).

Miller et al., Suppressor T cells generated by oral tolerization to myelin basic protein suppress both in vitro and in vivo immune responses by the release of transforming growth factor beta after antigen-specific triggering, Proc. Natl. Acad. Sci. USA, 89(1):421-5 (1992).

Murphy et al., Genetic construction, expression, and melanoma-selective cytotoxicity of a diphtheria toxin-related alpha-melanocyte-stimulating hormone fusion protein, Proc. Natl. Acad. Sci. USA, 83(21):8258-62 (1986).

Neimeyer, Functional hybrid devices of proteins and inorganic nanoparticles, Angew. Chem. Int. Ed. Eng., 42(47):5796-800 (2003).

Paidassi et al., C1q binds phosphatidylserine and likely acts as a multiligand-bridging molecule in apoptotic cell recognition, J. Immunol., 180(4):2329-38 (Feb. 2008).

Shevach et al., Control of T-cell activation by CD4+ CD25+ suppressor T cells, Immunol. Rev., 182:58-67 (Aug. 2001).

Waggoner, Covalent labeling of proteins and nucleic acids with fluorophores, Methods Enzymol., 246:362-73 (1995).

Waldner et al., Activation of antigen-presenting cells by microbial products breaks self tolerance and induces autoimmune disease, J. Clin. Invest., 113(7):990-7 (Apr. 2004).

Walker et al., The enemy within: keeping self-reactive T cells at bay in the periphery, Nat. Rev. Immunol., 2(1):11-9 (2002).

Getts et al., Microparticles bearing encephalitogenic peptides induce T-cell tolerance and ameliorate experimental autoimmune encephalomyelitis, Nat. Biotechnol., 30(12):1217-24 (Nov. 2012).

Maldonado et al., Polymeric synthetic nanoparticles for the induction of antigen-specfic immunological tolerance, Proc. Natl. Acad. Sci., 112(2):E156-E165 (Jan. 2015).

Makadia et al., Poly lactic-co-Glycolic acid (PLGA) as biodegradable controlled drug delivery carriers, Polymers, 3(4):1377-97 (Aug. 2011). .

Jin et al., The selective Immobilization of curcumln onto the Internal surface of mesoporous hollow silica particles by coalent bonding and its controlled release, J. Mater. Chem., 21:3641 (2011).

* cited by examiner

| Polymer | Coupling Efficiency |
|---|---|
| PLG-PLP$_{139-151}$ | 13.8% |
| PLG-PLP$_{178-191}$ | 28% |
| PLG-OVA$_{323-339}$ | 7.8% |

| Polymer | Coupling Efficiency |
|---|---|
| PLG-OVA$_{323-339}$ | 66.9% |
| PLG-PLP$_{139-151}$ | 73.6% |
| PLG-PLP$_{178-191}$ | 74.1% |

COVALENT POLYMER-ANTIGEN CONJUGATED PARTICLES

CROSS REFERENCE TO RELATED APPLICATIONS

This application is a National Stage Application of PCT/US2016/068423, filed Dec. 22, 2016, which claims the benefit of U.S. Provisional Application No. 62/387,183, filed Dec. 23, 2015 and U.S. Provisional Application No. 62/292,098, filed Feb. 5, 2016, the contents of each of which are incorporated herein by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: COUR-011_00 US_Seqlist.txt, date recorded: Dec. 23, 2015, file size 1.16 MB).

BACKGROUND OF INVENTION

Inflammatory diseases and disorders are conditions in which an abnormal or otherwise deregulated inflammatory response contributes to the etiology or severity of disease. Examples include autoimmune diseases such as type 1 diabetes and Celiac disease.

Many of these diseases are characterized by a mononuclear cell infiltration at a site of tissue injury or other insult. Examples of mononuclear cells that have been observed in these infiltrations include lymphocytes, especially T lymphocytes, and cells of the mononuclear phagocyte system (MPS cells) such as monocytes, macrophages, dendritic cells, microglial cells and others.

Many of the cells observed in the mononuclear cell infiltrates are suspected of having a role in these abnormal inflammatory responses. For example, in diseases such as multiple sclerosis, $CD4^+$ T cells are known to play a central role in the pathologic autoimmune response. At an earlier time point in T cell activation, dendritic cells and other MPS cells may be responsible for activation of $CD4^+$ T cells. MPS cells could also contribute to inflammation through phagocytosis although in at least some inflammatory diseases it is not clear whether such cells would be capable of this in the absence of $CD4^+$ T cells.

Peripheral blood monocytes may be classified into one of two groups according to the expression or not of certain cell surface molecules. In particular, human "resident monocytes" or "mature monocytes" are understood to have a $CD14^{lo}CD16^+$ phenotype (the mouse counterpart is $CX_3CR1^{hi}CCR2^-Gr1^-$). Another group of cells, the "inflammatory monocytes" or "immature monocytes" are understood to have a $CD14^+CD16^-$ phenotype (the mouse counterpart is $CX_3CR1^{lo}CCR2^+Gr1^+$). (Geissmann F. et al. 2003 Immunity 19: 71-82)

Importantly, while the latter are understood to be "inflammatory" in the sense that they are observed to migrate into inflamed tissue from bone marrow derived peripheral blood cells, these cells have not been shown to cause inflammation either directly or through the action of other cells. Further, the various MPS cells that may be formed when these cells differentiate have also not been shown to cause inflammation.

Conventional clinical strategies for general long-term immunosuppression in disorders associated with an undesired immune response are based on the long-term administration of broad acting immunosuppressive drugs, for example, signal 1 blockers such as cyclosporin A (CsA), FK506 (tacrolimus) and corticosteroids. Long-term use of high doses of these drugs can have toxic side-effects. Moreover, even in those patients that are able to tolerate these drugs, the requirement for life-long immunosuppressive drug therapy carries a significant risk of severe side effects, including tumors, serious infections, nephrotoxicity and metabolic disorders.

Methods of inducing antigen-specific tolerance have been developed, including cell coupling of an antigen or peptide. For example, in one method, peptide induced cell coupled tolerance involved collection, separation and treatment of peripheral blood cells with disease specific autoantigens and the ethylene carbodiimide (EDCI) coupling reagent under sterile conditions, and subsequent re-infusion into the donor/patient. This process is costly and must be conducted under closely monitored conditions by skilled practitioners and is limited in the number of centers that can conduct the procedure. The use of red blood cells as the donor cell type expands the potential source to include allogeneic donors thus increasing the supply of source cells dramatically and potentially expanding the delivery of this therapy to any setting certified for blood transfusion. These approaches have significant limitations in terms of supply of source cells and necessity for tissue type matching to minimize immune response to the donor cells. In addition the local treatment of the cells to couple autoantigens via EDCI presents a significant quality control issue. Furthermore, these approaches also require at least some knowledge of the pathological antigen for which immune tolerance is sought.

Antigen-specific tolerance is generally not ideal because specific antigens/epitopes are generally not known in human diseases. Furthermore, antigens can vary from subject to subject. In order for an antigen specific approach to be effective, therefore, it would be necessary to determine which antigens each individual patient would recognize, or it would require coupling a library of possible peptides to the particles prior to administration.

Recently, peptide-coupled particles have been described which eliminates the requirement for a supply of source cells and circumvents the tissue-typing requirement of the prior approaches, See WO 2010/085509; US 2012/0076831; and US 2016/0166664, the contents of which are incorporated by reference herein in their entirety. Notwithstanding, the use of antigens coupled to the outside of particles is associated with increased anaphylaxis and has significant chemistry, manufacturing and control issues.

When the antigen is encapsulated within the particle, these adverse events are avoided, See WO 2013/192532; US 2015/0209293; WO 2015/023796; US 2015/0190485; and US 2015/0283218, the contents of both of which are herein incorporated by reference in their entireties. Further the size and the charge can be altered to enhance tolerance to specific antigens. The problem with antigen encapsulation within nanoparticles, however, is the ability to control the loading of the antigens as well as the release of the antigen. Currently, the amount of antigen goes into each particle cannot be precisely controlled. Similarly, the amount of antigen released is also not tightly controlled leading to the potential for a burst release effect under certain conditions where a slower more controlled release may be desirable. The present invention provides a process where particle size and antigen encapsulation as well as antigen release can be precisely controlled.

SUMMARY OF THE INVENTION

The present disclosure is directed to tolerizing immune modified particles (TIMPs) in which encapsulated antigens are covalently attached to the internal surface. The covalent coupling to the internal particle surface allows for exquisite control of particle size and antigen encapsulation efficiency while at the same time reducing the risk antigen burst effects and avoiding unwanted side effects associated with surface coupled peptides.

The present disclosure provides a composition comprising one or more antigens covalently attached to a carrier particle having a negative zeta potential, wherein said one or more antigens is encapsulated in said particle.

The present disclosure provides a composition comprising one or more antigens encapsulated within a polymeric carrier particle, wherein said one or more antigens is covalently attached to a polymer that makes up said polymeric carrier particle.

In some embodiments, the composition further comprises an unconjugated carrier polymer. In some embodiments, the composition further comprises a pharmaceutically acceptable carrier.

In some embodiments, the present invention provides compositions (e.g., for induction of antigen-specific tolerance) comprising a carrier particle (e.g., PLG particle) covalently attached to one or more antigenic peptides, wherein said one or more antigenic peptides is encapsulated in said carrier particle. In certain embodiments, the carrier particle is a poly(lactide-co-glycolide) (PLG) particle. In other embodiments, the carrier particle is a PLURONIC® stabilized polypropylene sulfide particle.

In some embodiments, the present invention provides compositions comprising: an antigen coupled to a carrier particle having a negative zeta potential. In some embodiments, the zeta potential of the particle is less than about −100 mV. In some embodiments, the zeta potential of the particle is between about −100 mV and about −15 mV. In some embodiments, the zeta potential of the particle is between about −100 mV and about −75 mV. In some embodiments, the zeta potential of the particle is between about −50 mV and about −20 mV. In some embodiments, the particle is a co-polymer having a molar ratio from about 50:50, 80:20 to about 100:0. In some embodiments, the co-polymers ratio may be, but not limited to, polystyrene: poly(vinyl carboxylate)/80:20, polystyrene:poly(vinyl carboxylate)/90:10, poly(vinyl carboxylate):polystyrene/80:20, poly(vinyl carboxylate):polystyrene/90:10, polylactic acid: polyglycolic acid/80:20, or polylactic acid:polyglycolic acid/90:10, or polylactic acid:polyglycolic acid/50:50. Yet in other embodiments, the particle is a polystyrene particle, a carboxylated polystyrene particle, PLURONIC® stabilized polypropylene sulfide particle, or a poly(lactic-co-glycolic acid) particle. In some embodiments, the particle is a poly (lactic-co-glycolic acid) particle.

In some embodiments, the particle has an average diameter of between about 0.1 μm to about 10 μm. In some embodiments, the particle has an average diameter of between 0.2 μm and about 2 μm. In some embodiments, the particle has an average diameter of between about 0.3 μm to about 5 μm. In some embodiments, the particle has an average diameter of between about 0.5 μm to about 3 μm. In some embodiments, the particle has an average diameter of between about 0.5 μm to about 1 μm. In some embodiments, the particle has an average diameter of about 0.5 μm.

In further embodiments, the one or more antigens comprises at least a portion of an autoimmune antigen, allergens, an antigen expressed on a tissue to be transplanted into a subject, an enzyme for enzyme replacement therapy, or an allergen. In some embodiments, the antigen comprises at least a portion of myelin basic protein, acetylcholine receptor, endogenous antigen, myelin oligodendrocyte glycoprotein, pancreatic beta-cell antigen, insulin, proinsulin, islet-specific glucose-6-phophatase catalytic subunit-related protein (IGRP), glutamic acid decarboxylase (GAD), collagen type 11, human cartilage gp39, fp130-RAPS, proteolipid protein, fibrillarin, small nucleolar protein, thyroid stimulating factor receptor, histones, glycoprotein gp70, pyruvate dehydrogenase dehydrolipoamide acetyltransferase (PCD-E2), hair follicle antigen, aqua porin 4, Desmoglein 1, Desmoglein 3, nicotinic acetylcholine receptor, A-gliaden, and human tropomyosin isoform 5, Bahia grass pollen (BaGP), peach allergen Pru p 3, alpha s 1-Caein Milk allergen, Apig1 celery allergen, Bere1 Brazil nut allergen, B-Lactoglobulin Milk allergen, Bovine serum albumin, Cor a 1.04 Hazelnut allergen, Ovalbumin Egg allergen, Advate, antihemophilic factor, Kogenate, Eloctate, recombinant factor VIII Fc fusion protein, Refacto, Novo VIIa, recombinant factor VII, eptacog alfa, Helixate, Monanine, Coagulation Factor IX, Wilate, Ceredase, Alglucerase, Cerezyme, Imiglucerase, Elelso, taliglucerase alfa, Fabrazyme, Agalsidase beta, Aldurazyme, —I-iduronidase, Myozyme, Acid-glucosidase, Elaprase, iduronate-2-sulfatase, Naglazyme arylsufatase B, or N-acetylgalactosamin e-4-sulfatase, proteinaceous therapies used in enzyme or coagluation factor replacement such as myozyme, alglucerase, imiglucerase, taliglucerase, agalsidase beta, 1-iduronidase, acid glucosidase, Iduronate-2-sulfatase, N-acetylgalactosamnie-4-sulfatase, antihemophilic factor, factor VII, eptacogalfa, factor IX, miglustat, romiplastim, epotetin alpha, protein C, laronidase, lumizyme, or Factor VIII.

In further embodiments, the one or more antigens comprises an autoimmune antigen, an antigen expressed on a tissue to be transplanted into a subject, an enzyme for enzyme replacement therapy, or an allergen. In non-limiting embodiments, the antigen comprises, for example, myelin basic protein, acetylcholine receptor, endogenous antigen, myelin oligodendrocyte glycoprotein, pancreatic beta-cell antigen, insulin, glutamic acid decarboxylase (GAD), collagen type 11, human cartilage gp39, fp130-RAPS, proteolipid protein, fibrillarin, small nucleolar protein, thyroid stimulating factor receptor, histones, glycoprotein gp70, pyruvate dehydrogenase dehydrolipoamide acetyltransferase (PCD-E2), hair follicle antigen, aqua porin 4, Desmoglein 1, Desmoglein 3, nicotinic acetylcholine receptor, A-gliaden, and human tropomyosin isoform 5, Bahia grass pollen (BaGP), peach allergen Pru p 3, alpha s 1-Caein Milk allergen, Apig1 celery allergen, Bere1 Brazil nut allergen, B-Lactoglobulin Milk allergen, Bovine serum albumin, Cor a 1.04 Hazelnut allergen, insulin, proinsulin, islet-specific glucose-6-phophatase catalytic subunit-related protein (IGRP), Ovalbumin Egg allergen, proteinaceous therapies used in enzyme or coagluation factor replacement such as myozyme, alglucerase, imiglucerase, taliglucerase, agalsidase beta, 1-iduronidase, acid glucosidase, Iduronate-2-sulfatase, N-acetylgalactosamnie-4-sulfatase, antihemophilic factor, factor VII, eptacogalfa, factor IX, miglustat, romiplastim, epotetin alpha, protein C, laronidase, lumizyme, or Factor VIII.

In further embodiments, the particles are covalently coupled to one or more antigens comprising one or more epitopes. In a further embodiment, the epitope is associated with an allergy, an autoimmune disease, an enzyme used in enzyme replacement therapy, lysosomal storage disease, or an inflammatory disease or disorder. In one embodiment, the epitope is associated with type 1 diabetes, multiple sclerosis, Systemic Lupus, Neuromyelitis Optica, Idiopathic Thrombocytopenic Purpura, Thrombotic Thrombocytopenic Purpura, Membranous Nephropathy, Bullous Phemphigoid, Phemphigus Vulgaris, Myasthenia Gravis, a mucopolysaccharide storage disorder, gangliosidosis, alkaline hypophosphatasia, cholesterol ester storage disease, hyperuricemia, growth hormone deficiency, renal anemia, Gaucher's disease, Fabry's disease, Hurler's disease, Hunter's disease, Maroteaux-Lamy disease, hemophilia A, hemophilia B, von Wilebrand disease, venous thrombosis, purpura fulminans, mucopolysaccaridosis VI, pompe disease, Celiac's disease, or inflammatory bowel disease, including Crohn's disease or colitis, e.g. ulcerative colitis. In a further embodiment the epitopes are found within proteinaceous therapies used in enzyme or coagulation factor replacement such as myozyme, alglucerase, imiglucerase, taliglucerase, agalsidase beta, 1-iduronidase, acid glucosidase, Iduronate-2-sulfatase, N-acetylgalactosamnie-4-sulfatase, antihemophilic factor, factor VII, eptacogalfa, factor IX, miglustat, romiplastim, epotetin alpha, protein C, laronidase, lumizyme Factor VIII. In a further embodiment, the epitope is an epitope described in Tables 2 or 3. In one embodiment, the particles are coupled to antigens comprising only one epitope associated with one disease and/or disorder. In a further embodiment, antigens comprise more than one epitope associated with the same disease and/or disorder. In a further embodiment, the antigens comprise more than one epitope associated with different diseases and/or disorders.

In some embodiments, the one or more antigens is covalently coupled to said particle by a conjugate molecule. In some embodiments, the one or more antigens is directly covalently bound to said carrier particle. In some embodiments, the one or more antigens is covalently coupled to said particle by a linker. In some embodiments, the conjugate molecule comprises a carbodiimide compound. In some embodiments, the conjugate molecule comprises 1-Ethyl-3-(3-dimethylaminopropyl)carbodiimide (EDC). In some embodiments, the linkers can include, but are not limited to, a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde, paraformaldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene), Biotinylation and streptavidin complexing. Particular coupling agents include N-succinimidyl-3-(2-pyridyldithio)propionate (SPDP) and N-succinimidyl-4-(2-pyridylthio)pentanoate (SPP) to provide for a disulfide linkage.

In some embodiments, the one or more antigens is encapsulated in the particle which has a negative surface zeta potential. In some embodiments, the particle is biodegradable.

In some embodiments, the present invention provides methods of inducing antigen-specific tolerance in a subject comprising: administering to said subject an effective amount of a composition comprising one or more antigens covalently coupled to a carrier particle having a negative zeta potential, wherein said one or more antigens is encapsulated in said particle, and wherein said particle and antigen induce tolerance of said antigen in said subject.

In some embodiments, the present invention provides a method of inducing antigen-specific tolerance in a subject comprising: administering to said subject an effective amount of a composition comprising one or more antigens covalently attached to a carrier particle having a negative zeta potential, wherein said one or more antigens is encapsulated in said particle.

In some embodiments, administering is performed to treat or prevent a disease or condition. In some embodiments, administering is performed prior or subsequent to onset of a disease or condition that is caused by said antigen. In some embodiments, the disease or condition is selected from the group consisting of: an autoimmune disease, inflammatory disease, an allergy, transplantation rejection, a lysosomal storage disease, an enzyme deficiency, inflammatory response and a hyperimmune response. In some embodiments, the disease or condition is selected from the group consisting of: multiple sclerosis, type 1 diabetes, asthma, a food allergy, an environmental allergy, Celiac disease, inflammatory bowel disease, including Crohn's disease or ulcerative colitis, a mucopolysaccharide storage disorder, gangliosidosis, alkaline hypophosphatasia, cholesterol ester storage disease, hyperuricemia, growth hormone deficiency, renal anemia Hemophilia, Hemophilia A, Hemophilia B, von Willebrand disease, Gaucher's Disease, Fabry's Disease, Hurler's Disease, Pompe's Disease, Hunter's Disease, Maroteaux-Lary Disease and a condition caused by said antigen in said subject to reduce overreaction to said antigen. In some embodiments, said composition minimizes or eliminates burst release of said antigen in said subject after administration. In some embodiments, methods further comprise repeating said administration of said composition into said subject.

In a further embodiment, the administration of the particles results in activation induced death of effector T cells.

In a further embodiment, the administration of the particles results in anergy of effector T cells.

In a further embodiment, the administration of particles results in apoptosis of effector T cells.

In a further embodiment, the administration of particles results in the conversion of effector T cells to regulatory T cells.

In a further embodiment, the administration of particles results in the conversion of effector T cells to FOXP3 expressing regulatory T cells.

In a further embodiment, the administration of particles results in the conversion of effector T cells to regulatory T cells devoid of FOXP3 expression.

In a further embodiment, the administration of particles results in the induction and expansion of both antigen specific and non-specific regulatory T cells. In a further embodiment, the administration of particles results in the isolation of effector T cells in the lymph nodes and spleen inhibiting their ability to traffic to peripheral sites and cause inflammation.

In a further embodiment, the administration of particles results in the down regulation of T cell dependent antibody production.

In certain embodiments, the present invention provides methods for treating celiac disease in a subject comprising administering to said subject an effective amount of a composition comprising an antigen covalently coupled to a carrier particle having a negative zeta potential. In certain embodiments, the antigen is gliaden or a gliaden epitope. In some embodiments, the antigen is one or more antigens selected from the group consisting of SEQ ID NOs: 1295-1724, SEQ ID NOs: 1726-1766 and SEQ ID NOs: 4986-5140. In some embodiments, the antigen is gliaden and the antigen-coupled particle has a post-synthesis average size of about 600-1500 nanometers and a post-synthesis average charge of about −30 to about −80 mV. In some embodiments, the particle has a post-synthesis average size of about 600-1200 nanometers and a post-synthesis average charge of about −40 to about −70 mV. In certain embodiments, the particle has a post-synthesis average size of about 600 microns and a post-synthesis average charge of about −50 mV. In further embodiments, the particle is a polystyrene particle, a carboxylated polystyrene particle, a PLURONIC® stabilized polypropylene sulfide particle, or a polylactic-co-glycolic acid) particle.

In some embodiments, the present invention provides methods of treating diabetes in a subject comprising administering to said subject an effective amount of a composition comprising an antigen covalently coupled to a carrier particle having a negative zeta potential, wherein said antigen is encapsulated in said particle. In some embodiments, the diabetes is type I diabetes. In some embodiments, the diabetes is type II diabetes.

In some embodiments, the antigen is insulin, proinsulin, islet-specific glucose-6-phophatase catalytic subunit-related protein (IGRP) or epitopes derived from insulin proinsulin, or IGRP. In some embodiments, the antigen is one or more antigen selected from the group consisting of ID NOs: 1767-1840, SEQ ID NOs: 1842-1962, SEQ ID NOs: 19642027, SEQ ID NOs: 2029-2073, SEQ ID NOs: 2075-2113, SEQ ID NOs: 2115-2197, SEQ ID NOs: 2199-2248, SEQ ID NOs: 2250-2259, SEQ ID NOs: 2261-2420, SEQ ID NOs: 24222486, and SEQ ID NOs: 2489-2505. In some embodiments, the antigen is insulin and the antigen-coupled particle has a post-synthesis average size of about 300-800 nanometers and a post-synthesis average charge of about −30—to about −70 mV. In some embodiments, the particle has a post-synthesis average size of about 350-600 nanometers and a post-synthesis average charge of about −40 to about −60 mV. In some embodiments, the particle has a post-synthesis average size of about 500 nanometers and a post-synthesis average charge of about −50 mV. In some embodiments, the antigen is pro-insulin and the antigen-coupled particle has a post-synthesis average size of about 300-800 nanometers and a post-synthesis average charge of about −30 to about −70 mV. In certain embodiments, the particle has a post-synthesis average size of about 400-600 nanometers and a post-synthesis average charge of about −40 to about −60 mV. In some embodiments, the particle has a post-synthesis average size of about 570 nanometers and a post-synthesis average charge of about −45 mV. In some embodiments, the antigen is IGRP and the antigen-coupled particle has a post-synthesis average size of about 300-800 nanometers and a post-synthesis average charge of about −30 to about −70 mV. In some embodiments, the particle has a post-synthesis average size of about 400-700 nanometers and a post-synthesis average charge of about −40 to about −60 mV. In some embodiments, the particle has a post-synthesis average size of about 600 nanometers and a post-synthesis average charge of about −40 mV. In certain embodiments, the particle is a polystyrene particle, a carboxylated polystyrene particle, a PLURONIC® stabilized polypropylene sulfide particle, or a polylactic-co-glycolic acid) particle.

In some embodiments, the present invention provides methods of treating a subject undergoing enzyme replacement therapy, comprising administering to said subject an effective amount of a composition comprising one or more antigens covalently coupled to a carrier particle having a negative zeta potential, wherein said one or more antigens is encapsulated in said particle. In some embodiments, the subject is undergoing enzyme replacement therapy for treatment of a disease selected from the group consisting of Hemophilia, Hemophilia A, Hemophilia B, von Willebrand disease, a mucopolysaccharide storage disorder, gangliosidosis, alkaline hypophosphatasia, cholesterol ester storage disease, hyperuricemia, growth hormone deficiency, renal anemia Gaucher's Disease, Fabry's Disease, Hurler's Disease, Pompe's Disease, Hunter's Disease, and Maroteaux-Lary Disease. In some embodiments the antigen coupled particle comprises one or more enzyme selected from the group consisting of Advate, antihemophilic factor, Kogenate, Eloctate, recombinant factor VIII Fc fusion protein, Refacto, Novo VIIa, recombinant factor VII, eptacog alfa, Helixate, Monanine, Coagulation Factor IX, Wilate, Ceredase, Alglucerase, Cerezyme, Imiglucerase, Elelso, taliglucerase alfa, Fabrazyme, Agalsidase beta, Aldurazyme, —I-iduronidase, Myozyme, Acid-glucosidase, Elaprase, iduronate-2-sulfatase, Naglazyme arylsufatase B, and N-acetylgalactosamin e-4-sulfatase. In some embodiments, the particle is a polystyrene particle, a carboxylated polystyrene particle, a PLURONIC stabilized polypropylene sulfide particle, or a polylactic-co-glycolic acid) particle. In certain embodiments, the particle is a co-polymer having a molar ratio from about 80:20 to about 100:0. In certain embodiments, the particle is a polystyrene particle, a carboxylated polystyrene particle, a PLURONIC stabilized polypropylene sulfide particle, or a polylactic-co-glycolic acid) particle. In other embodiments, the particle is a polylactic-co-glycolic acid) particle and has a copolymer ratio of about 50:50 polylactic acid:polyglycolic acid.

In a further embodiment, the administration of the particles of the invention prevents the accumulation of neutrophils and other granulocytes in a subject. In a further embodiment, the particles of the invention are administered to a subject who has cancer.

In one embodiment, administration of the particles of the invention increases regeneration of damaged tissue. In a further embodiment, the particles increase regeneration of epithelial cells. In yet a further embodiment, the particles increase remyelination of neurons. In another embodiment, the subject has an autoimmune disease. In yet another embodiment, the subject has inflammatory bowel disease, including ulcerative colitis, and/or Crohn's disease. In yet another embodiment, the subject has multiple sclerosis.

In one embodiment, administration of the particles of the invention to a subject minimizes or eliminates burst release of said antigen in said subject after administration.

In some embodiments the composition is administered intravenously. In some embodiments, the composition is administered subcutaneously, orally, intramuscularly, intralymphatically, portally or via aerosol. In one embodiment, administration of the negatively charged particles induces antigen-specific tolerance in a subject. In one embodiment, the particles that induce antigen-specific tolerance comprise one or more epitopes associated with an allergy, autoimmune disease, and/or inflammatory disease. In one embodiment, the epitopes are selected from those described in Tables 2 or 3. In one embodiment, the negatively charged particles are polystyrene, diamond, PLURONIC® stabilized polypropylene sulfide, or polylactic-co-glycolic acid) particles. In one embodiment the particles are carboxylated. In one embodiment, the particles have a zeta potential of less than about −100 mV. In some embodiments, the particles have a zeta potential between about −100 mV and about −15 mV. In some embodiments, the particles have a zeta potential between about −100 mV and about −75 mV. In some embodiments, the particles have a zeta potential between about −50 mV and about −20 mV. In one embodiment, the particle has an average diameter of about 0.1 µm to about 10 µm, for example from about 0.2 µm to about 2 µm or about 0.3 µm to about 5 µm, or 0.5 µm to about 3 µm or about 0.5 µm to about 1 µm.

In one embodiment, the subject has an autoimmune disease. In one embodiment, the autoimmune disease is multiple sclerosis, scleroderma, type-I diabetes, rheumatoid arthritis, thyroiditis, systemic lupus erythmatosis, Reynaud's syndrome, Sjorgen's syndrome, autoimmune uveitis, autoimmune myocarditis, inflammatory bowel disease, Amyotrophic Lateral Sclerosis (ALS), Systemic Lupus, Neuromyelitis Optica, Idiopathic Thrombocytopenic Purpura, Thrombotic Thrombocytopenic Purpura, Membranous Nephropathy, Bullous Phemphigoid, Phemphigus Vulgaris, Myasthenia Gravis, Celiac disease, ulcerative colitis, or Crohn's disease. In one embodiment, the particle comprises a full-length polypeptide or fragment thereof. In one embodiment, the particle comprises one or more myelin basic protein epitopes. In one embodiment, the myelin basic protein epitope is from SEQ ID NO: 4975 or SEQ ID NO: 4976. In one embodiment, the particles comprise one or more myelin oligodendrocyte glycoprotein epitopes. In one embodiment, the myelin oligodendrocyte glycoprotein epitope is from SEQ ID NO: 1 or SEQ ID NO: 4978. In one embodiment, the particle contains one or more insulin epitopes. In one embodiment, the one or more insulin epitopes is from SEQ ID NO: 4981. In one embodiment, the particle comprises one or more glutamic acid decarboxylase epitopes. In one embodiment, the glutamic acid decarboxylase epitopes is from SEQ ID NO: 4982. In one embodiment, the particle contains one or more proteolipid protein epitopes. In one embodiment, the proteolipid protein epitope is from SEQ ID NO: 4977. In one embodiment, the particle comprises one or more gliaden epitopes. In one embodiment, the gliaden epitopes comprise SEQ ID NOs: 4983-4985.

In one embodiment, the present invention provides for a method of inducing regulatory T cells comprising treating said T cells with an effective amount of a composition comprising one or more antigens covalently coupled to a carrier particle having a negative zeta potential, wherein said one or more antigens is encapsulated in said particle, and wherein the particle size is greater than 80 nm.

In some embodiments, the present invention further provides a process for the preparation of a tolerizing immune modified particle (TIMP) having a negative zeta potential, said process comprising: a) covalently linking one or more carrier polymers with one or more antigens to form carrier polymer-antigen conjugates; and b) combining carrier polymer-antigen conjugates with unconjugated carrier polymer at predetermined mixing ratios in a solution under conditions effective to form the TIMP, wherein a TIMP having a negative zeta potential is formed, and wherein the one or more antigens is encapsulated in the TIMP.

In some embodiments, the present invention further provides a process for the preparation of a tolerizing immune modified particle (TIMP) having a negative zeta potential, said process comprising: a) covalently linking one or more carrier polymers with one or more antigens to form carrier polymer-antigen conjugates; and b) contacting the carrier polymer-antigen conjugates with a solution under conditions effective to form the TIMP, wherein the TIMP having a negative zeta potential is formed, and wherein the one or more antigens is encapsulated in the TIMP. In some embodiments, the contacting the carrier polymer-antigen conjugates with a solution occurs in the presence of an unconjugated carrier polymer at predetermined mixing ratios.

In some embodiments, the particle created by the process has a zeta potential of less than about −100 mV. In some embodiments, the particle has a zeta potential between about −100 mV and about −15 mV. In some embodiments, the particle has a zeta potential between about −100 mV and about −75 mV. In some embodiments, the particle has a zeta potential between about −50 mV and about −20 mV.

In some embodiments, the particle created by the process has an average diameter of about 0.1 µm to about 10 µm, for example from about 0.2 µm to about 2 µm or about 0.3 µm to about 5 µm, or 0.5 µm to about 3 µm or about 0.5 µm to about 1 µm.

In some embodiments, the particle created by the process comprises a polystyrene particle, a carboxylated polystyrene particle, PLURONIC® stabilized polypropylene sulfide particle, or a poly(lactic-co-glycolic acid) particle. In some embodiments, the particle comprises a poly(lactic-co-glycolic acid) particle.

In some embodiments, the one or more antigens of the process is covalently coupled to said one or more carrier polymers by a conjugate molecule. In some embodiments, the one or more antigens is covalently coupled to said one or more carrier polymers by a linker. In some embodiments, the conjugate molecule comprises a carbodiimide compound. In some embodiments, the conjugate molecule comprises 1-Ethyl-3-(3-dimethylaminopropyl)carbodiimide (EDC).

In some embodiments, the one or more carrier polymers is formed by co-polymerization. In some embodiments, the solution is a buffer solution. In some embodiments, the solution has a basic pH. In some embodiments, the solution comprises sodium bicarbonate, potassium bicarbonate, lithium bicarbonate, potassium dihydrogen phosphate, sodium dihydrogen phosphate, or lithium dihydrogen phosphate.

In some embodiments, the TIMPs does not contain other bioactive agents (i.e. drugs, immunomodulators, cytokines). In some embodiments, the TIMP is biodegradable. In some embodiments, the process further comprises formulating said TIMP in a pharmaceutically acceptable carrier.

BRIEF DESCRIPTION OF THE DRAWINGS

(FIG. 4A and FIG. 4D) MHCII marker expression following treatment with 400 nm and 80 nm particles, respectively, (FIG. 4B and FIG. 4E) CD80 marker expression following treatment with 400 nm and 80 nm particles, respectively, (FIG. 4C and FIG. 4F) CD86 marker expression following treatment with 400 nm and 80 nm particles, respectively.

FIG. 8A, mice were injected either intravenously (IV) or subcutaneously (SC) with 1.25 mg of 400 nm or 80 nm PLG-Cy5.5 nanoparticle formulation. Cells from the liver, kidney, heart, lung, spleen and inguinal lymph nodes were isolated. Data was analyzed by flow cytometry 24 hr after injection. FIG. 8B, the proportion of cells that were CD45+ versus CD45– was determined for liver, spleen and lung. FIG. 8C, mice were injected IV with 1.25 mg of PLG-Cy5.5 nanoparticle formulations of various particle sizes. Data was analyzed by flow cytometry 24 hr after injection. The proportion of Cy5.5+ cells found in the liver, spleen and lung was determined for a given particle size. FIG. 8D, the percentage of either CD45+ or CD45– cells that were Cy5.5+ was determined for a given particle size. FIG. 8E, the percentage of either CD45+ or CD45– cells that were Cy5.5+ was determined for the 400 nm PLG-Cy5.5 particle size.

FIG. 11 shows synthesis and characterization of PLG-peptide conjugates and nanoparticle formation.

(FIG. 12A and FIG. 12B) The effect of antigen loading on CD25 and (FIG. 12C and FIG. 12D) Foxp3 expression of T cells was measured. Although both particles formulations were able to increase CD25 expression similarly, only 400 nm acPLG-OVA$_{323\text{-}339}$ particles could efficiently induce CD4$^+$CD25$^+$Foxp3$^+$ regulatory T cells.

(FIG. 14A) Treatment of mice with nanoparticle formulations resulted in significantly abrogated clinical disease scores compared to PBS. (FIG. 14B) Corresponding cumulative clinical score for mice treated with tolerogenic particles. (n=3-7).

(FIG. 15A) Schematic representation of antigen-polymer conjugate nanoparticles delivering multiple Ags. (FIG. 15B) Treatment of mice with acPLG nanoparticle formulated with both pathogenic epitopes resulted in significantly abrogated mean clinical disease scores compared to mice treated with only a single or irrelevant epitope. (FIG. 15C) Corresponding cumulative clinical score for mice treated with particles. (n=3-7).

DETAILED DESCRIPTION OF THE INVENTION

Figure 1:
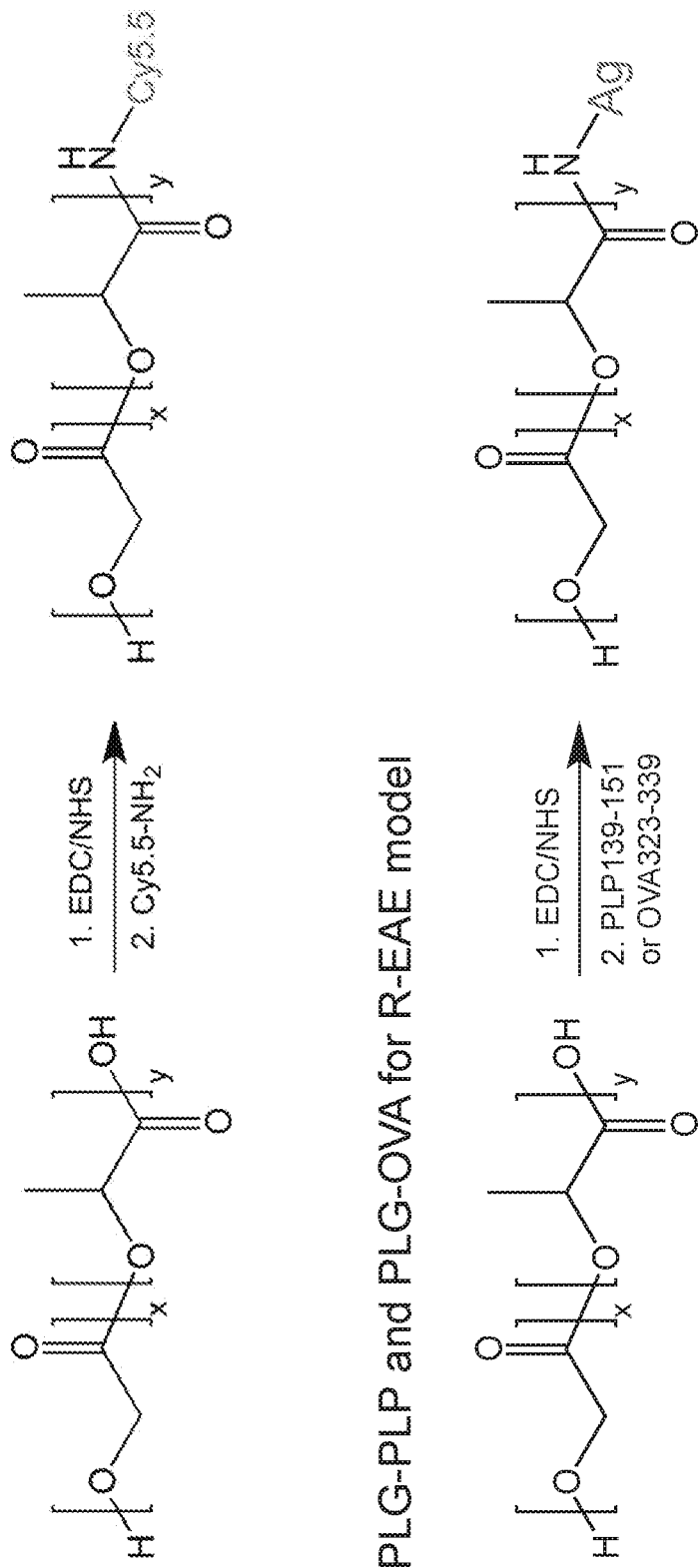
FIG. 1 shows the synthesis of PLG-fluorescent dye and PLG-antigen conjugates using EDC/NHS as the coupling reagent.
Figure 2A:
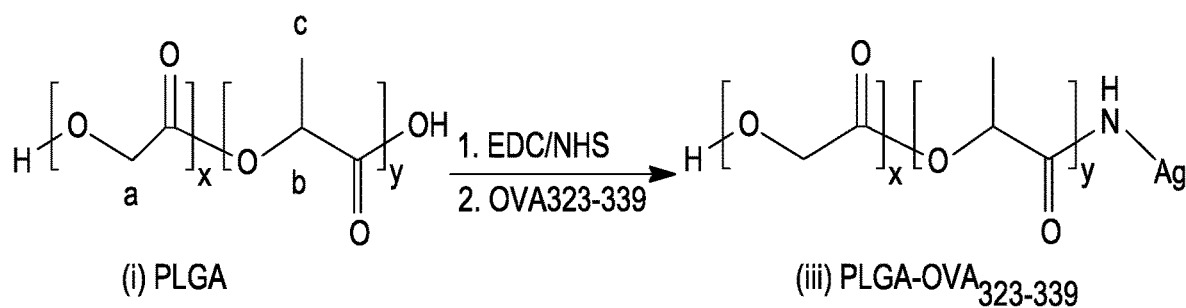
FIG. 2 shows the synthesis and characterization of PLG-peptide conjugates and nanoparticle formation. $^1$H-NMR spectrum of (i) PLG, (ii) $OVA_{323-339}$, and (iii) PLG-$OVA_{323-339}$ measured in DMSO-d6 (calibrated at 2.5 ppm) (FIG. 2A). The coupling efficiency of $OVA_{323-339}$, $PLP_{139-151}$ and $PLP_{178-191}$ to PLG was calculated by comparing the integration values of the overlapping methyl proton peaks of leucine and isoleucine present at 1.4 ppm in $OVA_{323-339}$ (d, d') to the methylene proton peak present at 5.3 ppm in PLG (b).
(FIG. 2B). A schematic representation of polymer-conjugate nanoparticles is provided in FIG. 2C.
Figure 2A:
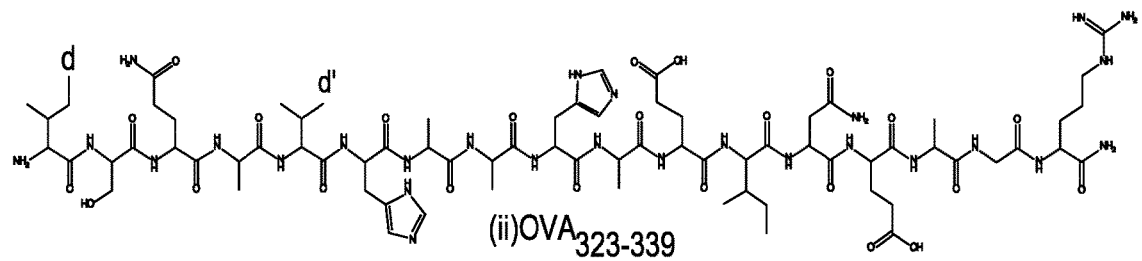
Figure 2A:
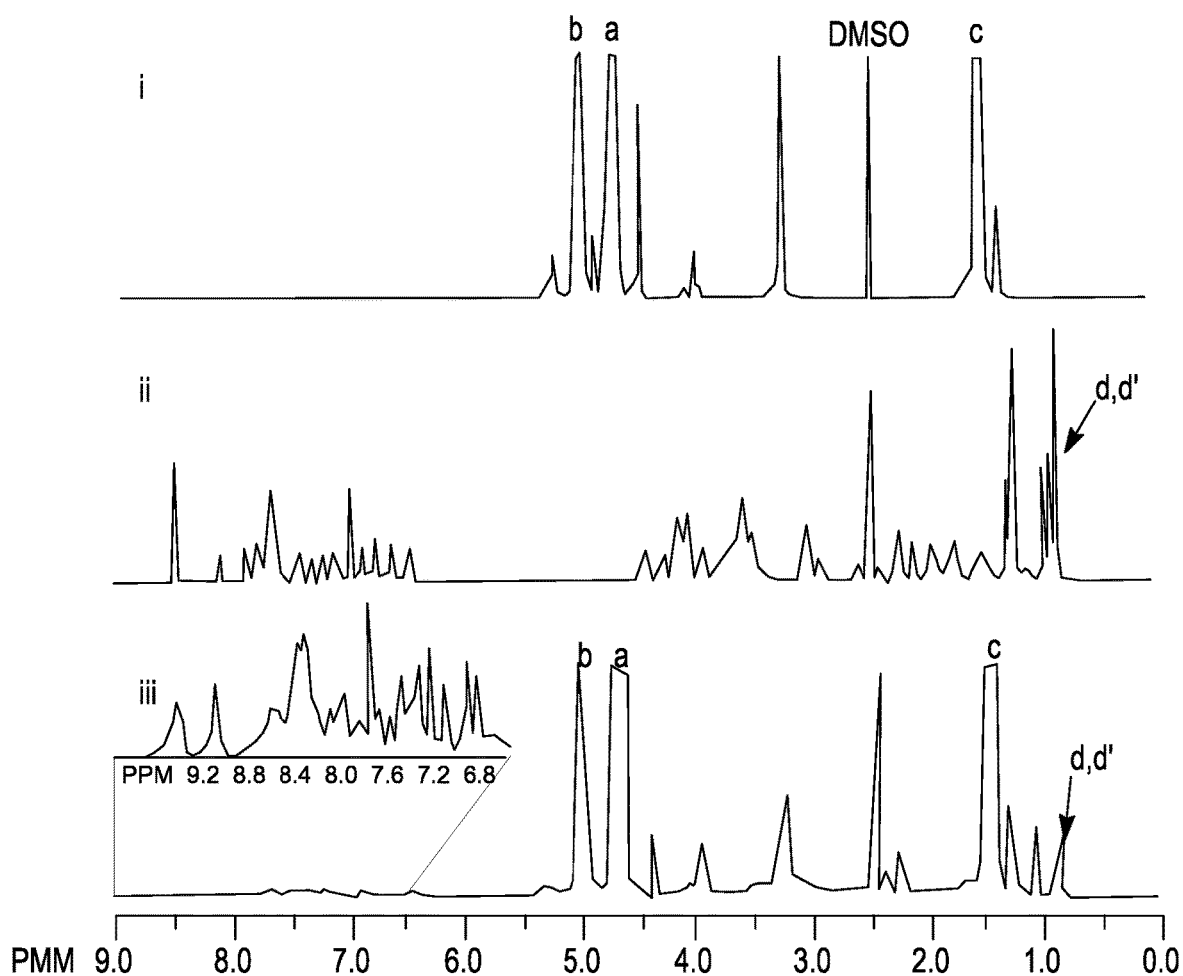
Figures 2B, 2C:
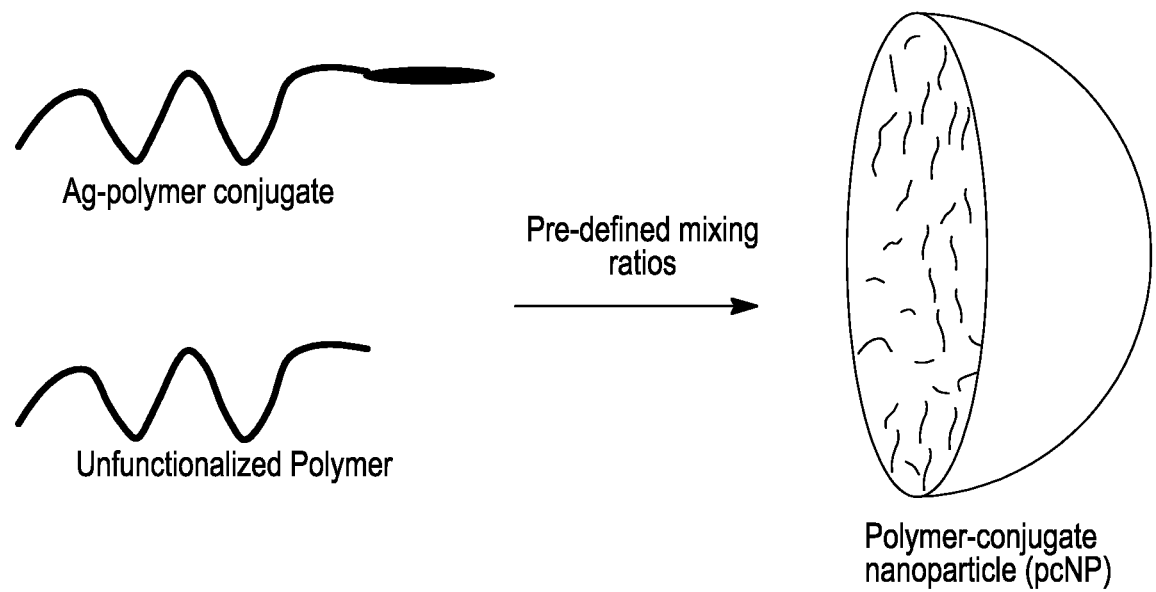

The present inventors have found that tolerizing immune modified particles (TIMPs) in which encapsulated antigens are covalently linked to the internal surface of the particles allow for exquisite control of particle size and antigen encapsulation and reduction of antigen burst effects while still avoiding the unwanted side effects associated with surface coupled peptides. The process for producing such TIMPs comprises covalently coupling one or more antigens to one or more carrier polymers to form carrier polymer-antigen conjugates, followed by combining carrier polymer-antigen conjugates with unconjugated carrier polymer at predetermined mixing ratios in a solution under conditions effective to form TIMPs, with one or more antigens encapsulated therein. These TIMPs can induce tolerance to autoimmune disease and decrease the immune response. These particles, therefore, may be useful in the treatment of any disease or condition characterized by an excessive inflammatory immune response, such as autoimmune diseases or allergies. These TIMPs can minimize or eliminate burst release of one or more antigens from the particle. Minimizing or eliminating burst release of an antigen may be desirable, for example, to better control the amount of antigen released during treatment, to avoid toxic levels of the antigen, and/or to avoid ineffective antigen delivery.

As used herein and in the appended claims, the singular forms "a," "an," and "the" include plural reference unless the context clearly indicates otherwise.

It is understood that aspects and embodiments of the invention described herein include "comprising," "consisting," and "consisting essentially of" aspects and embodiments.

In some embodiments, reference to "about" a value or parameter herein includes (and describes) variations that are directed to that value or parameter per se. For example, description referring to "about X" includes description of "X".

"Particle" as used herein refers to any non-tissue derived composition of matter. It may be a sphere or sphere-like entity, bead, or liposome. The term "particle", the term "immune modifying particle", the term "carrier particle", and the term "bead" may be used interchangeably depending on the context. Additionally, the term "particle" may be used to encompass beads and spheres.

"Negatively charged particle" as used herein refers to particles which have been modified to possess a net surface charge that is less than zero.

"Carboxylated particles" or "carboxylated beads" or "carboxylated spheres" includes any particle that has been modified to contain a carboxyl group on its surface. In some embodiments the addition of the carboxyl group enhances phagocyte/monocyte uptake of the particles from circulation, for instance through the interaction with scavenger receptors such as MARCO. Carboxylation of the particles can be achieved using any compound which adds carboxyl groups, including, but not limited to, poly(ethylene-maleic anhydride) (PEMA).

"Carrier particle" as used herein refers to a particle that is covalently coupled to an antigen before forming a tolerizing immune modified particle (TIMP). Also, "carrier particle" or "carrier polymer" as used herein refers to a polymer that can be covalently attached to an antigen to form a tolerizing immune modified particle (TIMP). The particle may be a polymer which can be, but is not limited to, polystyrene, carboxylated polystyrene, diamond, PLURONIC® stabilized polypropylene sulfide or polylactic-co-glycolic acid).

"Unconjugated carrier polymer" or "unconjugated carrier particle" refers to a carrier polymer or carrier particle that does not comprise an antigen covalently bound thereto.

"Loading" as used herein refers to the amount of antigen per amount of carrier polymer. Loading can be expressed as micrograms (µg) of antigen per milligram (mg) of carrier polymer.

"Antigenic moiety" as used herein refers to any moiety, for example, a peptide that is recognized by the host's immune system. Examples of antigenic moieties include, but are not limited to, autoantigens, enzymes, and/or bacterial or viral proteins, peptides, drugs or components. Without being bound by theory, while the carboxylated beads themselves may be recognized by the immune system, the carboxylated beads with nothing more attached thereto are not considered an "antigenic moiety" for the purposes of the invention.

"Naked beads" or "naked particles" or "naked spheres" as used herein refers to beads, particles or spheres that have not been carboxylated.

"Pro-inflammatory mediators" or "pro-inflammatory polypeptides" as used herein refers to polypeptides or fragments thereof which induce, maintain, or prolong inflammation in a subject. Examples of pro-inflammatory mediators include, but are not limited to, cytokines and chemokines.

As used herein, the term "Inflammatory monocyte" refers to any myeloid cell expressing any combination of CD14/CD26 and CCR2.

As used herein, the term "inhibitory neutrophil" refers to neutrophils, and/or monocyte derived suppressor cells.

As used herein, the term "Th cell" or "helper T cell" refers to CD4$^+$ cells. CD4$^+$ T cells assist other white blood cells with immunologic processes, including maturation of B cells into plasma cells and memory B cells, and activation of cytotoxic T cells and macrophages. T cells become activated when they are presented with peptide antigens by MHC class II molecules, which are expressed on the surface of antigen-presenting cells (APCs).

As used herein, the term "Th1 cell" refers to a subset of Th cells which produce proinflammatory mediators. Th1 cells secrete cytokines to facilitate immune response and play a role in host defense against pathogens in part by mediating the recruitment of neutrophils and macrophages to infected tissues. Th1 cells secrete cytokines including IFN-gamma, IL2, IL-10, and TNF alpha/beta to coordinate defense against intracellular pathogens such as viruses and some bacteria.

As used herein, the term "Th2 cell" refers to a subset of Th cells that mediate the activation and maintenance of the antibody-mediated immune response against extracellular parasites, bacteria, allergens, and toxins. Th2 cells mediate these functions by producing various cytokines such as IL-4, IL-5, IL-6, IL-9, IL-13, and IL-17E (IL-25) that are responsible for antibody production, eosinophil activation, and inhibition of several macrophage functions, thus providing phagocyte-independent protective responses.

As used herein, the term "Th17 cell" refers to a subset of Th cells. Th17 cells secrete cytokines to facilitate immune response and play a role in host defense against pathogens by mediating the recruitment of neutrophils and macrophages to infected tissues. TH17 cells secrete cytokines such as IL17, IL21, IL22, IL24, IL26 and TNF alpha to coordinate defense against extracellular pathogens including fungi and bacteria.

"Coupled", "linked" or "crosslinked" as used herein with reference to an antigen refers to an antigen covalently bound or covalently attached to a carrier particle and encapsulated within the particle.

The term "IMP" as used herein refers to immune-modifying particles which are not coupled to an antigen. The term "TIMP" as used herein refers to tolerizing immune modifying particles which are coupled to an antigen. In certain embodiments, the term "IMP" as used herein refers to immune-modifying particles which do not comprise an antigen. The term "TIMP" as used herein refers to tolerizing immune modifying particles which comprise an antigen.

The term "bioactive agents" refers to agents other than those used to construct the particle (i.e. polymers, linkers) and the antigens contained therein. Examples of bioactive agents include drugs, immunomodulators and cytokines.

The particle may have any particle shape or conformation. However, in some embodiments it is preferred to use particles that are less likely to clump in vivo. Examples of particles within these embodiments are those that have a spherical shape.

One aspect of the invention relates to a composition which comprises an immune modified particle with a negative zeta potential coupled to one or more antigens, wherein the one or more antigens is encapsulated within the particle.

Yet another aspect of the invention relates to a process for the preparation of a tolerizing immune modified particle (TIMP) with a negative zeta potential, said process comprising: a) covalently linking one or more carrier polymers with one or more antigens to form carrier polymer-antigen conjugates; and b) combining carrier polymer-antigen conjugates with unconjugated carrier polymer at predetermined mixing ratios in a solution under conditions effective to form the TIMP, wherein a TIMP with a negative zeta potential is formed. In some embodiments of this invention, the carrier polymer is formed via copolymerization. The particle microstructure may depend on the method of co-polymerization.

In some embodiments, the present disclosure provides a process for the preparation of a tolerizing immune modified particle (TIMP) having a negative zeta potential, said process comprising: a) covalently linking one or more carrier polymers with one or more antigens to form carrier polymer-antigen conjugates; and b) contacting the carrier polymer-antigen conjugates with a solution under conditions effective to form the TIMP, wherein the TIMP having a negative zeta potential is formed, and wherein the one or more antigens is encapsulated in the TIMP. In some embodiments, the contacting the carrier polymer-antigen conjugates with a solution occurs in the presence of an unconjugated carrier polymer at predetermined mixing ratios.

In some embodiments, an antigenic peptide molecule is coupled to the carrier polymer (e.g. PLG) by a conjugate molecule and/or linker group. In some embodiments, coupling of the antigenic peptide and/or apoptotic signalling molecule to the carrier polymer (e.g., PLG) comprises one or more covalent interactions. In some embodiments, the antigenic peptide is encapsulated within the carrier particle with a negative zeta potential.

In one embodiment, the solution contacting the carrier polymer-antigen conjugates and unconjugated carrier polymer may have a basic pH. Suitable basic pH for the basic solution include 7.1, 7.5, 8.0, 8.5, 9.5, 10.0, 10.5, 11.0, 11.5, 12.0, 12.5, 13.0, and 13.5. The solution may also be made of any suitable base and its conjugate. In some embodiments of the invention, the solution may include, without limitation, sodium bicarbonate, potassium bicarbonate, lithium bicarbonate, potassium dihydrogen phosphate, sodium dihydrogen phosphate, or lithium dihydrogen phosphate and conjugates thereof.

In one embodiment of the invention, the tolerizing immune modified particles contain co-polymers. These co-polymers may have varying molar ratio. Suitable co-polymer ratio of present tolerizing immune modified particles may be 25:75, 30:70, 35:65, 40:60, 45:55, 50:50, 55:45, 60:40, 65:35, 70:30, 75:25, 80:20, 81:19, 82:18, 83:17, 84:16, 85:15, 86:14, 87:13, 88:12, 89:11, 90:10, 91:9, 92:8, 93:7, 94:6, 95:5, 96:4, 97:3, 98:2, 99:1, or 100:0. In another embodiment, the co-polymer may be periodical, statistical, linear, branched (including star, brush, or comb co-polymers) co-polymers. In some embodiments, the copolymers ratio may be, but not limited to, polystyrene:poly(vinyl carboxylate)/80:20, polystyrene:poly(vinyl carboxylate)/90:10, poly(vinyl carboxylate):polystyrene/80:20, poly(vinyl carboxylate):polystyrene/90:10, polylactic acid:polyglycolic acid/50:50, polylactic acid:polyglycolic acid/80:20, or polylactic acid:polyglycolic acid/90:10.

In one embodiment, the particles of the invention are made by adding a composition comprising the carrier particle to a solution of an unconjugated carrier polymer. In some embodiments, the carrier particle is contacted with a solution in the presence of an unconjugated carrier polymer at predetermined mixing ratios. In some embodiments, the unconjugated carrier polymer is PLG (poly(lactide-co-glycolic acid)).

In one embodiment, the particles of the invention are made by adding a composition comprising the polymer to a solution of a biocompatible polymer. Examples of biocompatible polymers include Poly(ethylene-maleic anhydride) (PEMA) and citric acid based polymer scaffolds. Further examples of biocompatible polymers include poly(alpha-esters), polyurethanes, poly(ester amide), poly(ortho esters), polyanhydrides, poly(anhydride-co-imide), cross-linked polyanhydrides, poly(propylene fumarate), psuedo poly (amino acid), poly(alkyl cyanoacrylates), polyphosphazenes, polyphosphoester, poly(amino acids), polysaccharides, poly(ethylene glycol). (Nair et al. Progress in Polymer Science, 32 (2007) 762-798, which is incorporated herein by reference) A solution of biocompatible polymer can include same or different polymers and mixed in different ratios to provide different effects.

In one embodiment, the particles of the invention are made by adding a composition comprising the polymer (e.g. PLGA) to a solution of Poly(ethylene-maleic anhydride)

(PEMA). The concentration of PEMA in the solution can be between about 0.1% and about 10%. In one embodiment, the concentration of PEMA in the solution is between about 0.2% and about 5%. In another embodiment, the concentration of PEMA in the solution is between about 0.1% and 4%. In another embodiment, the concentration of PEMA in the solution is between about 0.1% and 2%. In another embodiment, the concentration of PEMA in the solution is between about 0.5% and 1%. In one embodiment, the percentage of PEMA in
solution is 0.1%, 0.2%, 0.3%, 0.4%, 0.5%, 0.6% 0.7%, 0.8%, 0.9%, 1%, 1.5%, 2%, 2.5%, 3%, 3.5%, 4%, 4.5%, 5%, 6%, 6.5%, 7%, 7.5%, 8%, 8.5%, 9%, 9.5% or 10%. In one embodiment, the percentage of PEMA in the solution is about 0.5%. In another embodiment, the percentage of PEMA in the solution is about 1.0%. Other compounds that may be used include, but are not limited to, Poly(ethylene-alt-maleic anhydride), Poly(isobutylene-co-maleic acid), Poly(methyl vinyl ether-alt-maleic acid), Poly(methyl vinyl ether-alt-maleic acid monoethyl ester), Poly(methyl vinyl ether-alt-maleic anhydride), Poly(methyl vinyl ether-alt-maleic anhydride) cross-linked with 1,9-decadiene powder, and/or Poly(styrene-alt-maleic acid) sodium salt.

In one embodiment, the particle is a liposome. In a further embodiment, the particle is a liposome composed of the following lipids at the following molar ratios—30:30:40 phosphatidylcholine:phosphatidylglycerol:cholesterol. In yet a further embodiment, the particle is encapsulated within a liposome.

It is not necessary that each particle be uniform in size, although the particles must generally be of a size sufficient to be sequestered in the spleen or liver and trigger phagocytosis or uptake through receptor or non-receptor mediated mechanism by an antigen presenting cell, including endothelial cell or other MPS cell. Preferably, the particles are microscopic or nanoscopic in size, in order to enhance solubility, avoid possible complications caused by aggregation in vivo and to facilitate pinocytosis. Particle size can be a factor for uptake from the interstitial space into areas of lymphocyte maturation. A particle having a diameter of from about 0.1 µm to about 10 µm is capable of triggering phagocytosis. Thus in one embodiment, the particle has a diameter within these limits. In another embodiment, the particle has an average diameter of about 0.3 µm to about 5 µm. In still another embodiment, the particle has an average diameter of about 0.5 µm to about 3 µm. In another embodiment, the particle has an average diameter of about 0.2 µm to about 2 µm. In a further embodiment the particle has an average size of about 0.1 µm, or about 0.2 µm or
about 0.3 µm or about 0.4 µm or about 0.5 µm or about 1.0 µm or about 1.5 µm or about 2.0 µm or about 2.5 µm or about 3.0 µm or about 3.5 µm or about 4.0 µm or about 4.5 µm or about 5.0 µm. In a particular embodiment the particle has an average size of about 0.5 µm. In some embodiments, the overall weights of the particles are less than about 10,000 kDa, less than about 5,000 kDa, or less than about 1,000 kDa, 500 kDa, 400 kDa, 300 kDa, 200 kDa, 100 kDa, 50 kDa, 20 kDa, 10 kDa. The particles in a composition need not be of uniform diameter. By way of example, a pharmaceutical formulation may contain a plurality of particles, some of which are about 0.5 µm, while others are about 1.0 µm. Any mixture of particle sizes within these given ranges will be useful.

The particles of the current invention can possess a particular zeta potential. In certain embodiments, the zeta potential is negative. In one embodiment, the zeta potential is less than about −100 mV. In one embodiment, the zeta potential is less than about −50 mV. In certain embodiments, the particles possess a zeta potential between −100 mV and 0 mV. In a further embodiment, the particles possess a zeta potential between −75 mV and 0 mV. In a further embodiment, the particles possess a zeta potential between −60 mV and 0 mV. In a further embodiment, the particles possess a zeta potential between −50 mV and 0 mV. In still a further embodiment, the particles possess a zeta potential between −40 mV and 0 mV. In a further embodiment, the particles possess a zeta potential between −30 mV and 0 mV. In a further embodiment, the particles possess a zeta potential between −20 mV and +0 mV. In a further embodiment, the particles possess a zeta potential between −10 mV and −0 mV. In a further embodiment, the particles possess a zeta potential between −100 mV and −50 mV. In another particular embodiment, the particles possess a zeta potential between −75 mV and −50 mV. In a particular embodiment, the particles possess a zeta potential between −50 mV and −40 mV.

In some embodiments, the charge of a carrier (e.g., positive, negative, neutral) is selected to impart application-specific benefits (e.g., physiological compatibility, beneficial surface-peptide interactions, etc.). In some embodiments, a carrier has a net neutral or negative charge (e.g., to reduce non-specific binding to cell surfaces which, in general, bear a net negative charge). In certain embodiments carrier polymers are capable of being covalently conjugated, either directly or indirectly, to an antigen to which tolerance is desired (also referred to herein as an antigen-specific peptide, antigenic peptide, autoantigen, inducing antigen or tolerizing antigen). In some embodiments, carrier polymer-antigen conjugates are mixed with unconjugated carrier polymer at predetermined mixing ratios. In some embodiments, the predetermined mixing ratios can be 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5. In some embodiments, the predetermined mixing ratio is 50:50. In some instances, a carrier has multiple binding sites (e.g., 2, 3, 4, 5, 6, 7, 8, 9, 10 . . . 20 . . . 50 . . . 100, or more) in order to have multiple copies of an antigen-specific peptide, or multiple different peptides encapsulated within the carrier particle (e.g., to increase the likelihood of a tolerance response). In some embodiments, a carrier encapsulates a single type of antigenic peptide. In some embodiments, a carrier encapsulates multiple different antigenic peptides.

In some embodiments, the loading of antigen is about 0.10, 0.20, 0.30, 0.40, 0.50, 0.60, 0.70, 0.80, 0.90, 1, 2, 3, 4, 5, 6, 7, 8, 9, 10, 11, 12, 13, 14, 15, 16, 17, 18, 19, 20 µg antigen/mg carrier polymer and all values in between. In some embodiments, the loading of antigen is about 0.10 to about 0.50 µg antigen/mg carrier polymer. In some embodiments, the loading of antigen is about 0.50 to about 2 µg antigen/mg carrier polymer. In some embodiments, the loading of antigen is about 2 to about 4 µg antigen/mg carrier polymer. In some embodiments, the loading of antigen is about 4 to about 8 µg antigen/mg carrier polymer. In some embodiments, the loading of antigen is about 8 to about 16 µg antigen/mg carrier polymer. In some embodiments, the loading of antigen is about 16 to about 20 µg antigen/mg carrier polymer. In some embodiments, the loading of antigen is about 20 to about 30 µg antigen/mg carrier polymer. In some embodiments, the loading of antigen is about 30 to about 40 µg antigen/mg carrier polymer. In some embodiments, the loading of antigen is about 40 to about 50 µg antigen/mg carrier polymer. In some embodiments, the loading of antigen is about 50 to about 60 µg antigen/mg carrier polymer. In some embodiments, the loading of antigen is about 60 to about 70 µg antigen/mg carrier polymer. In some embodiments, the loading of antigen is about 70 µg antigen or more/mg carrier polymer.

The size and charge of the particles are critical for tolerance induction. While the particles will differ in size and charge based on the antigen encapsulated within them (See Table 1 and Table 5 for examples of specific particles), in general, particles of the current invention are effective at inducing tolerance when they are between about 100 nanometers and about 1500 nanometers and have a charge of 0 to about −100 mV and are most effective at inducing tolerance when they are 400-800 microns and have a charge of between about −25 mV and −70 mV. As used herein, the term "post-synthesis size" and "post synthesis charge" refer to the size and charge of the particle prior to lyophilization. The term "post lyophilization size" and "post lyophilization charge" refer to the size and charge of the particle after lyophilization. Table 1 shows the sizes and zeta potentials of representative nanoparticle formulations. Particles with various sizes were prepared by the double emulsion and nanoprecipitation methods. Loading (µg antigen (Ag)/mg PLG) was precisely controlled by combining PLG-Ag conjugates with unconjugated PLG at predetermined mixing ratios. Tables 1 and 5 show sizes and zeta potentials of representative nanoparticle formulations.

TABLE 1

Sizes and zeta potentials of representative nanoparticle formulations

| Type | Particle | Loading (µg/mg) | Size (nm ± S.D.) | Zeta (mV ± S.D.) |
|---|---|---|---|---|
| Double Emulsion | PLG | 0 | 521.5 ± 23. | −56.0 ± 0.67 |
| | PLG-Cy5.5 | 0 | 454.8 ± 26. | −39.7 ± 0.47 |
| | PLG-OVA | 0.1 | 406.0 ± 6.4 | −52.2 ± 1.1 |
| | PLG-OVA | 0.5 | 456.5 ± 9.3 | −34.9 ± 2.0 |
| | PLG-OVA | 2 | 421.2 ± 1.5 | −58.1 ± 2.9 |
| | PLG-OVA | 8 | 443.7 ± 7.8 | −52.6 ± 1.2 |
| | PLG-PLP | 8 | 656.5 ± 13.7 | −45.5 ± 1.4 |
| | PLG-OVA | 16 | 470.7 ± 15. | −50.5 ± 2.3 |
| Nano-precipitation | PLG | 0 | 72.2 ± 1.9 | −33.5 ± 1.1 |
| | PLG-Cy5.5 | 0 | 79.04 ± 0.78 | −31.3 ± 0.55 |
| | PLG-OVA | 0.1 | 74.8 ± 0.25 | −34.5 ± 0.25 |
| | PLG-OVA | 0.5 | 85.6 ± 1.9 | −31.5 ± 1.2 |
| | PLG-OVA | 1 | 103.9 ± 0.25 | −32.4 ± 0.56 |
| | PLG-OVA | 2 | 112.0 ± 0.60 | −32.0 ± 0.85 |

In some embodiments, the particle is non-metallic. In these embodiments the particle may be formed from a polymer. In a preferred embodiment, the particle is biodegradable in an individual. In this embodiment, the particles can be provided in an individual across multiple doses without there being an accumulation of particles in the individual. Examples of suitable particles include polystyrene particles, PLGA particles, PLURONIC® stabilized polypropylene sulfide particles, and diamond particles. In some embodiments, suitable particles include particles prepared from general classes of polymers such as poly(alphaesters), polyurethanes, poly(ester amide), poly(ortho esters), polyanhydrides, poly(anhydride-co-imide), cross-linked polyanhydrides, poly(propylene fumarate), psuedo poly (amino acid), poly(alkyl cyanoacrylates), polyphosphazenes, polyphosphoester, poly(amino acids), and polysaccharides.

Preferably the particle surface is composed of a material that minimizes non-specific or unwanted biological interactions. Interactions between the particle surface and the interstitium may be a factor that plays a role in lymphatic uptake. The particle surface may be coated with a material to prevent or decrease non-specific interactions. Steric stabilization by coating particles with hydrophilic layers such as poly(ethylene glycol) (PEG) and its copolymers such as PLURONIC® (including copolymers of poly(ethylene glycol)-b1-poly(propylene glycol)-b1-poly(ethylene glycol)) may reduce the non-specific interactions with proteins of the interstitium as demonstrated by improved lymphatic uptake following subcutaneous injections. All of these facts point to the significance of the physical properties of the particles in terms of lymphatic uptake. Biodegradable polymers may be used to make all or some of the polymers and/or particles and/or layers. Biodegradable polymers may undergo degradation, for example, by a result of functional groups reacting with the water in the solution. The term "degradation" as used herein refers to becoming soluble, either by reduction of molecular weight or by conversion of hydrophobic groups to hydrophilic groups. Polymers with ester groups are generally subject to spontaneous hydrolysis, e.g., polylactides and polyglycolides.

Particles of the present invention may also contain additional components. For example, carriers may have imaging agents incorporated or conjugated to the carrier. An example of a carrier nanosphere having an imaging agent that is currently commercially available is the Kodak X-sight nanospheres. Inorganic quantum-confined luminescent nanocrystals, known as quantum dots (QDs), have emerged as ideal donors in FRET applications: their high quantum yield and tunable size-dependent Stokes Shifts permit different sizes to emit from blue to infrared when excited at a single ultraviolet wavelength. (Bruchez, et al., Science, 1998, 281, 2013; Niemeyer, C. M Angew. Chem. Int. Ed. 2003, 42, 5796; Waggoner, A. Methods Enzymol. 1995, 246, 362; Brus, L. E. J. Chem. Phys. 1993, 79, 5566). Quantum dots, such as hybrid organic/inorganic quantum dots based on a class of polymers known as dendrimers, may used in biological labeling, imaging, and optical biosensing systems. (Lemon, et al., J. Am. Chem. Soc. 2000, 122, 12886). Unlike the traditional synthesis of inorganic quantum dots, the synthesis of these hybrid quantum dot nanoparticles does not require high temperatures or highly toxic, unstable reagents. (Etienne, et al., Appl. Phys. Lett. 87, 181913, 2005).

Particles of the present invention may be covalently linked to an imaging agent such as a cyanine fluorescent dye. In some embodiments, the cyanines comprise open chain cyanines, hemicyanines and/or closed chain cyanines. In some embodiments, the cyanine fluorescent dye comprises Cy2, Cy3, Cy3B, Cy3.5, Cy5, Cy5.5 and Cy7. In some embodiments, the particles are covalently linked to Cy5.5 for in vivo imaging.

Particles can be formed from a wide range of materials. The particle is preferably composed of a material suitable for biological use. For example, particles may be composed of glass, silica, polyesters of hydroxy carboxylic acids, polyanhydrides of dicarboxylic acids, or copolymers of hydroxy carboxylic acids and dicarboxylic acids. More generally, the carrier particles may be composed of polyesters of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy hydroxy acids, or polyanhydrides of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy dicarboxylic acids.

Additionally, carrier particles can be quantum dots, or composed of quantum dots, such as quantum dot polystyrene particles (Joumaa et al. (2006) Langmuir 22: 1810-6). Carrier particles including mixtures of ester and anhydride bonds (e.g., copolymers of glycolic and sebacic acid) may also be employed. For example, carrier particles may comprise materials including polyglycolic acid polymers (PGA), polylactic acid polymers (PLA), polysebacic acid polymers (PSA), polylactic-co-glycolic) acid copolymers (PLGA or PLG; the terms are interchangeable), [rho]oly(lactic-co-sebacic) acid copolymers (PLSA), poly(glycolic-co-sebacic) acid copolymers (PGSA), polypropylene sulfide polymers, poly(caprolactone), chitosan, etc. Other biocompatible, biodegradable polymers useful in the present invention include polymers or copolymers of caprolactones, carbonates, amides, amino acids, orthoesters, acetals, cyanoacrylates and degradable urethanes, as well as copolymers of these with straight chain or branched, substituted or unsubstituted, alkanyl, haloalkyl, thioalkyl, aminoalkyl, alkenyl, or aromatic hydroxy- or di-carboxylic acids. In addition, the biologically important amino acids with reactive side chain groups, such as lysine, arginine, aspartic acid, glutamic acid, serine, threonine, tyrosine and cysteine, or their enantiomers, may be included in copolymers with any of the aforementioned materials to provide reactive groups for conjugating to antigen peptides and proteins or conjugating moieties. Biodegradable materials suitable for the present invention include diamond, PLA, PGA, polypropylene sulfide, and PLGA polymers. Biocompatible but non-biodegradable materials may also be used in the carrier particles of the invention. For example, non-biodegradable polymers of acrylates, ethylene-vinyl acetates, acyl substituted cellulose acetates, non-degradable urethanes, styrenes, vinyl chlorides, vinyl fluorides, vinyl imidazoles, chlorosulphonated olefins, ethylene oxide, vinyl alcohols, TEFLON® (DuPont, Wilmington, Del.), and nylons may be employed.

Preparation of Compositions

The particles of the instant invention can be manufactured by any means commonly known in the art. Exemplary methods of manufacturing particles include, but are not limited to, microemulsion polymerization, interfacial polymerization, precipitation polymerization, emulsion evaporation, emulsion diffusion, solvent displacement, and salting out (Astete and Sabliov, J. Biomater. Sci. Polymer Edn., 17:247-289(2006)). Manipulation of the manufacturing process for PLGA particles can control particle properties (e.g. size, size distribution, zeta potential, morphology, hydrophobicity/hydrophilicity, polypeptide entrapment, etc). The size of the particle is influenced by a number of factors including, but not limited to, the concentration of PLGA, the solvent used in the manufacture of the particle, the nature of the organic phase, the surfactants used in manufacturing, the viscosity of the continuous and discontinuous phase, the nature of the solvent used, the temperature of the water used, sonication, evaporation rate, additives, shear stress, sterilization, and the nature of any encapsulated antigen or polypeptide.

Particle size is affected by the polymer concentration; higher particles are formed from higher polymer concentrations. For example, an increase in PLGA concentration from 1% to 4% (w/v) can increase mean particle size from about 205 nm to about 290 nm when the solvent propylene carbonate is used. Alternatively, in ethyl acetate and 5% Pluronic F-127, an increase in PLGA concentration from 1% to 5% (w/v) increases the mean particle size from 120 nm to 230 nm.

The viscosity of the continuous and discontinuous phase is also an important parameter that affects the diffusion process, a key step in forming smaller particles. The size of the particles increases with an increase in viscosity of the dispersed phase, whereas the size of the particles decreases with a more viscous continuous phase. In general, the lower the phase ratio of organic to aqueous solvent, the smaller the particle size.

Homogenizer speed and agitation also affect particle size; in general, higher speeds and agitation cause a decrease in particle size, although there is a point where further increases in speed and agitation no longer decrease particle size. There is a favorable impact in the size reduction when the emulsion is homogenized with a high pressure homogenizer compared with just high stirring. For example, at a phase ratio of 20% in 5% PVA, the mean particle size with stirring is 288 nm and the mean particle size with homogenization (high pressure of 300 bars) is 231 nm.

An important size reduction of the particles can be achieved by varying the temperature of the water added to improve the diffusion of the solvent. The mean particle size decreases with an increase in water temperature.

The nature of the polypeptide encapsulated in the particle also affects particle size. In general, encapsulation of hydrophobic polypeptides leads to the formation of smaller particles compared with the encapsulation of more hydrophilic polypeptides. In the double emulsion process, the entrapment of more hydrophilic polypeptides is improved by using high molecular mass PLGA and a high molecular mass of the first surfactant which causes a higher inner phase viscosity. The interaction between the solvent, polymer, and polypeptide affects the efficiency of incorporating the polypeptide into the particle.

The PLGA molecular mass impacts the final mean particle size. In general, the higher the molecular mass, the higher the mean particle size. For example, as the composition and molecular mass of PLGA varies (e.g. 12 to 48 kDa for 50:50 PLGA; 12 to 98 kDa for 75:25 PLGA) the mean particle size varies (about 102 nm-154 nm; about 132 nm to 152 nm respectively). Even when particles are the same molecular mass, their composition can affect average particle size; for example, particles with a 50:50 ratio generally form particles smaller than those with a 75:25 ratio. The end groups on the polymer also affect particle size. For example, particles prepared with ester end-groups form particles with an average size of 740 nm (PI=0.394) compared with the mean size for the acid PLGA end-group is 240 nm (PI=0.225).

The solvent used can also affect particle size; solvents that reduce the surface tension of the solution also reduce particle size.

The organic solvent is removed by evaporation in a vacuum to avoid polymer and polypeptide damage and to promote final particle size reduction. Evaporation of the organic solvent under vacuum is more efficient in forming smaller particles. For example, evaporation in vacuum produces a mean particle size around 30% smaller than the mean particle size produced under a normal rate of evaporation.

The amplitude of the sonication wavelength also affects the particle characteristics. The amplitude of the wavelength should be over 20% with 600 to 800 s of sonication to form stable miniemulsions with no more droplet size changes. However, the main draw-back of sonication is the lack of monodispersity of the emulsion formed.

Organic phases that may be used in the production of the particles of the invention include, but are not limited to, methylene chloride, ethyl acetate, methyl ethyl ketone, propylene carbonate, and benzyl alcohol. The continuous phases that may be used include, but are not limited to, the surfactant poloxamer 188.

A variety of surfactants can be used in the manufacturing of the particles of the invention. The surfactant can be anionic, cationic, or nonionic. Surfactants in the poloxamer and poloaxamines family are commonly used in particle synthesis. Surfactants that may be used, include, but are not limited to PEG, Tween-80, gelatin, dextran, pluronic L-63, PVA, methylcellulose, lecithin, DMAB, PEMA, sodium deoxycholate, poly(acrylic acid), hyaluronic acid, and other negatively-charged naturally occurring or synthetic small molecules or polymers. Additionally, biodegradable and biocompatible surfactants including, but not limited to, vitamin E TPGS (D-α-tocopheryl polyethylene glycol 1000 succinate). In certain embodiments, two surfactants are needed (e.g. in the double emulsion evaporation method). These two surfactants can include a hydrophobic surfactant for the first emulsion, and a hydrophobic surfactant for the second emulsion.

Another manufacturing technique includes nanoprecipitation. For example, a polymer is soluble in an organic solvent, yet the organic solvent is miscible with the aqueous phase. Upon mixing the organic (polymer-containing solution) with the aqueous phase, the polymer can precipitate and form particles since the aqueous phase is a non-solvent for the polymer.

Solvents that may be used in the production of the particles of the invention include, but are not limited to, ethyl acetate, acetone, Tetrahydrofuran (THF), chloroform, and members of the chlorinate family, methylene chloride. The choice of organic solvents require two selection criteria: the polymer must be soluble in this solvent, and the solvent must be completely immiscible with the aqueous phase.

Salts that may be used in the production of the particles of the invention include, but are not limited to magnesium chloride hexahydrate, magnesium acetate tetrahydrate.

Common salting-out agents include, but are not limited to, electrolytes (e.g. sodium chloride, magnesium acetate, magnesium chloride), or non-electrolytes (e.g. sucrose).

The stability and size of the particles of the invention may be improved by the addition of compounds including, but not limited to, fatty acids or short chains of carbons. The addition of the longer carbon chain of lauric acid is associated with the improvement of particle characteristics. Furthermore, the addition of hydrophobic additives can improve the particle size, incorporation of the polypeptide into the particle, and release profile. Preparations of particles can be stabilized by lyophilization. The addition of a cryoprotectant such as trehalose can decrease aggregation of the particles upon lyophilization.

Suitable beads which are currently available commercially include polystyrene beads such as FluoSpheres (Molecular Probes, Eugene, Oreg.).

In some embodiments, the present invention provides systems comprising: (a) a delivery scaffold configured for the delivery of chemical and/or biological agents to a subject; and (b) antigen-coupled poly(lactide-co-glycolide) particles for induction of antigen-specific tolerance. In some embodiments, at least a portion of said delivery scaffold is microporous. In some embodiments, the antigen-coupled poly(lactide-co-glycolide) particles are encapsulated within said scaffold. In some embodiments, the chemical and/or biological agents are selected from the group consisting of: protein, peptide, small molecules, nucleic acids, cells, and particles. In some embodiments, chemical and/or biological agents comprise cell, and said cells comprise pancreatic islet cells.

Physical properties are also related to a nanoparticle's usefulness after uptake and retention in areas having immature lymphocytes. These include mechanical properties such as rigidity or rubberiness. Some embodiments are based on a rubbery core, e.g., a poly(propylene sulfide) (PPS) core with an overlayer, e.g., a hydrophilic overlayer, as in PEG, as in the PPS-PEG system recently developed and characterized for systemic (but not targeted or immune) delivery. The rubbery core is in contrast to a substantially rigid core as in a polystyrene or metal nanoparticle system. The term rubbery refers to certain resilient materials besides natural or synthetic rubbers, with rubbery being a term familiar to those in the polymer arts. For example, cross-linked PPS can be used to form a hydrophobic rubbery core. PPS is a polymer that degrades under oxidative conditions to polysulphoxide and finally polysulphone, transitioning from a hydrophobic rubber to a hydrophilic, water-soluble polymer. Other sulphide polymers may be adapted for use, with the term sulphide polymer referring to a polymer with a sulphur in the backbone of the mer. Other rubbery polymers that may be used are polyesters with glass transition temperature under hydrated conditions that is less than about 37° C. A hydrophobic core can be advantageously used with a hydrophilic overlayer since the core and overlayer will tend not to mingle, so that the overlayer tends to sterically expand away from the core. A core refers to a particle that has a layer on it. A layer refers to a material covering at least a portion of the core. A layer may be adsorbed or covalently bound. A particle or core may be solid or hollow. Rubbery hydrophobic cores are advantageous over rigid hydrophobic cores, such as crystalline or glassy (as in the case of polystyrene) cores, in that higher loadings of hydrophobic drugs can be carried by the particles with the rubbery hydrophobic cores.

Another physical property is the surface's hydrophilicity. A hydrophilic material may have a solubility in water of at least 1 gram per liter when it is uncrosslinked. Steric stabilization of particles with hydrophilic polymers can improve uptake from the interstitium by reducing nonspecific interactions; however, the particles' increased stealth nature can also reduce internalization by phagocytic cells in areas having immature lymphocytes. The challenge of balancing these competing features has been met, however, and this application documents the creation of nanoparticles for effective lymphatic delivery to DCs and other APCs in lymph nodes. Some embodiments include a hydrophilic component, e.g., a layer of hydrophilic material. Examples of suitable hydrophilic materials are one or more of polyalkylene oxides, polyethylene oxides, polysaccharides, polyacrylic acids, and polyethers. The molecular weight of polymers in a layer can be adjusted to provide a useful degree of steric hindrance in vivo, e.g., from about 1,000 to about 100,000 or even more; artisans will immediately appreciate that all the ranges and values within the explicitly stated ranges are contemplated, e.g., between 10,000 and 50,000.

The nanoparticles may incorporate functional groups for further reaction. Functional groups for further reaction include electrophiles or nucleophiles; these are convenient for reacting with other molecules. Examples of nucleophiles are primary amines, thiols, and hydroxyls. Examples of electrophiles are succinimidyl esters, aldehydes, isocyanates, and maleimides.

A great variety of means, well known in the art, may be used to conjugate antigenic peptides and proteins to carrier polymers. These methods include any standard chemistries which do not destroy or severely limit the biological activity of the antigen peptides and proteins, and which allow for a sufficient number of antigen peptides and proteins to be conjugated to the carrier polymer in an orientation which allows for interaction of the antigen peptide or protein with a cognate T cell receptor. Generally, methods are preferred which conjugate the C-terminal regions of an antigen peptide or protein, or the C-terminal regions of an antigen peptide or protein fusion protein, to the earner. The exact chemistries will, of course, depend upon the nature of the earner material, the presence or absence of C-terminal fusions to the antigen peptide or protein, and/or the presence or absence of conjugating moieties.

Functional groups can be located on the carrier polymer as needed for availability. One location can be as side groups or termini on the core polymer or polymers that are layers on a core or polymers otherwise tethered to the particle. For instance, examples are included herein that describe PEG stabilizing the nanoparticles that can be readily functionalized for specific cell targeting or protein and peptide drug delivery.

Conjugation Procedure

The present disclosure provides conjugates of carrier particles (e.g., carrier polymers). The polymer is typically a chemical species containing a plurality of repeating units that are bonded to each other. A polymer may contain more than one different repeating unit. The repeating unit typically derives from polymerization of a monomer. A copolymer specifically refers to a polymer containing two or more structurally different repeating units. The different repeating units of a polymer may be randomly ordered in the polymer chain or the same repeating units may be grouped into contiguous blocks in the polymer. When there are contiguous blocks of the two or more repeating units in a polymer, the polymer is a block co-polymer. In certain embodiments, the polymer is a graft co-polymer. As used herein the term polymer refers to a chemical species containing more than about 10 repeating units.

Suitable carrier particle (e.g., carrier polymer) for conjugation comprises functional group for reaction. The carrier particle (e.g., carrier polymer) described herein can be chemically modified by reactions to introduce a desired terminal functional group. Terminal functional groups include among others, carboxyl, hydroxyl, thiol, amine, azide, alkyne, alkene, ketone, phenol, halide, imidazole, guanidinium, carboxylate, or phosphate groups. These functional groups can be introduced at the terminus of the carrier particle (e.g., carrier polymer) herein employing well known chemical methods.

The functional groups can be employed to further conjugate the carrier particle (e.g., carrier polymer) with other chemical species, such as other polymers, other oligomers, peptides, proteins, small molecules, carbohydrates, antibodies, nucleic acids, and/or aptamers.

In certain embodiments, the carrier particle (e.g., carrier polymer) comprises a carboxyl group, which can be conjugated to an amino-containing conjugate partner with use of carbodiimide crosslinking chemistry. Carbodiimide reagents are used as coupling reagents for reaction of carboxylic acids towards amide or ester formation. Examples of carbodiimide reagents include EDCI (1-ethyl-3-(3-dimethylaminopropyl)carbodiimide, or EDC, or ECDI), DCC (N,N'-dicyclohexylcarbodiimide), and DIC (N,N'-diisopropylcarbodiimide). In addition to the coupling reagent, activation reagents may be used to facilitate the reaction. Examples of activating reagents include hydroxysuccinimide. Reaction of carbodiimide-activated carboxylic acid on a carrier particle (e.g., carrier polymer) with an amino-containing conjugate partner can produce an amide bond connecting the carrier polymer and conjugate partner.

In certain embodiments, the carrier particle (e.g., carrier polymer) and the conjugate partner (e.g., antigen) are coupled with use of polyfunctional coupling reagents (e.g., bifunctional coupling reagents). The selection of the polyfunctional coupling reagent depends on the functional groups present on the carrier particle (e.g., carrier polymer) and the conjugate partner (e.g., antigen).

The groups of the polyfunctional coupling reagent can independently include a carboxyl-reactive group, carbonyl-reactive group, an amine-reactive group, a thiol-reactive group or a photo-reactive group, but are not the same (e.g., orthogonal). Examples of carboxyl-reactive groups include hydrazine derivatives and amines. Examples of carbonyl-reactive groups include aldehyde- and ketone-reactive groups like hydrazine derivatives and amines. Examples of amine-reactive groups include active esters such as NHS or sulfo-NHS, isothiocyanates, isocyanates, acyl azides, sulfonyl chlorides, aldehydes, glyoxals, epoxides, oxiranes, carbonates, aryl halides, imidoesters, anhydrides and the like. Examples of thiol-reactive groups include non-polymerizable Michael acceptors, haloacetyl groups (such as iodoacetyl), alkyl halides, maleimides, aziridines, acryloyl groups, vinyl sulfones, benzoquinones, aromatic groups that can undergo nucleophilic substitution such as fluorobenzene groups (such as tetra and pentafluorobenzene groups), and disulfide groups such as pyridyl disulfide groups and thiols activated with Ellman's reagent. Examples of photo-reactive groups include aryl azide and halogenated aryl azides. Additional examples of each of these types of groups will be apparent to those skilled in the art. Further examples and information regarding reaction conditions and methods for exchanging one type of reactive group for another are provided in Hermanson, "Bioconjugate Techniques," Academic Press, San Diego, 1996, which is incorporated by reference herein.

Alternate Conjugation Procedure

Conjugates such as ethylene carbodiimide (EDCI), hexamethylene diisocyanate, propyleneglycol di-glycidylether which contain 2 epoxy residues, and epichlorohydrin may be used for fixation of peptides or proteins to the carrier polymer. Without being bound by theory, EDCI is suspected of carrying out two major functions for induction of tolerance: (a) it chemically couples the protein/peptides to the carrier polymer via catalysis of peptide bond formation between free amino and free carboxyl groups; and (b) it induces the carrier to mimic apoptotic cell death such that they are picked up by host antigen presenting cells (which may include endothelial cells) in the spleen and induce tolerance. It is this presentation to host T-cells in a non-immunogenic fashion that leads to direct induction of anergy in autoreactive cells. In addition, EDCI serves as a potent stimulus for the induction of specific regulatory T cells.

In one series of embodiments, the antigen peptides and proteins are bound to the carrier polymer via a covalent chemical bond. For example, a reactive group or moiety near the C-terminus of the antigen (e.g., the C-terminal carboxyl group, or a hydroxyl, thiol, or amine group from an amino acid side chain) may be conjugated directly to a reactive group or moiety of the carrier polymer (e.g., a hydroxyl or carboxyl group of a PLA or PGA polymer, a terminal amine or carboxyl group of a dendrimer, or a hydroxyl, carboxyl or phosphate group of a phospholipid) by direct chemical reaction. Alternatively, there may be a conjugating moiety which covalently conjugates to both the antigen peptides and proteins and the carrier polymer, thereby linking them together.

Reactive carboxyl groups of a carrier polymer may be joined to free amines (e.g., from Lys residues) on the antigen peptide or protein, by reacting them with, for example, 1-ethyl-3-[3,9-dimethyl aminopropyl]carbodiimide hydrochloride (EDC) or N-hydroxysuccinimide ester (NETS). Similarly, the same chemistry may be used to conjugate free amines on the surface of a carrier polymer with free carboxyls (e.g., from the C-terminus, or from Asp or Glu residues) on the antigen peptide or protein. Alternatively, free amine groups on a carrier polymer may be covalently bound to antigen peptides and proteins, or antigen peptide or protein fusion proteins, using sulfo-SIAB chemistry, essentially as described by Arano et al. (1991) Chem. 2:71-6.

Conjugation of a nucleic acid moiety to a platform molecule can be effected in any number of ways, typically involving one or more crosslinking agents and functional groups on the nucleic acid moiety and platform molecule. Linking groups are added to platforms using standard synthetic chemistry techniques. Linking groups can be added to nucleic acid moieties using standard synthetic techniques. The practitioner has a number of choices for antigens used in the combinations of this invention. The inducing antigen present in the combination contributes to the specificity of the tolerogenic response that is induced. It may or may not be the same as the target antigen, which is the antigen present or to be placed in the subject being treated which is a target for the unwanted immunological response, and for which tolerance is desired.

Biological and Chemical Antigens

An inducing antigen of this invention may be a polypeptide, polynucleotide, carbohydrate, glycolipid, or other molecule isolated from a biological source, or it may be a chemically synthesized small molecule, polymer, or derivative of a biological material, providing it has the ability to induce tolerance according to this description when combined with the mucosal binding component.

In some embodiments, the present invention provides a carrier polymer covalently coupled to one or more peptides, polypeptides, and/or proteins. In some embodiments, a carrier (e.g., PLG carrier), such as those described herein, are effective to induce antigen-specific tolerance and/or prevent the onset of an immune related disease (such as EAE in a mouse model) and/or diminish the severity of a pre-existing immune related disease. In some embodiments, the compositions and methods of the present invention can cause T cells to undertake early events associated with T-cell activation, but do not allow T-cells to acquire effector function. For example, administration of compositions of the present invention can result in T-cells having a quasi-activated phenotype, such as CD69 and/or CD44 upregulation, but do not display effector function, such as indicated by a lack of IFN-γ or IL-17 synthesis. In some embodiments, administration of compositions of the present invention results in T-cells having a quasi-activated phenotype without having conversion of naive antigen-specific T-cells to a regulatory phenotype, such as those having $CD25^{+/}Foxp3^{+}$ phenotypes.

In some embodiments, a carrier comprises one or more biological or chemical agents adhered to, adsorbed on, encapsulated within, and/or contained throughout the carrier. In some embodiments, a chemical or biological agent is encapsulated in and/or contained throughout the particles. The present invention is not limited by the nature of the chemical or biological agents. Such agents include, but are not limited to, proteins, nucleic acid molecules, small molecule drugs, lipids, carbohydrates, cells, cell components, and the like. In some embodiments, two or more (e.g., 3, 4, 5, etc.) different chemical or biological agents are included on or within the carrier. In some embodiments, agents are configured for specific release rates. In some embodiments, multiple different agents are configured for different release rates. For example, a first agent may release over a period of hours while a second agent releases over a longer period of time (e.g., days, weeks, months, etc.). In some embodiments, the carrier or a portion thereof is configured for slow-release of biological or chemical agents. In some embodiments, the slow release provides release of biologically active amounts of the agent over a period of at least 30 days (e.g., 40 days, 50 days, 60 days, 70 days, 80 days, 90 days, 100 days, 180 days, etc.). In some embodiments, the carrier or a portion thereof is configured to be sufficiently porous to permit ingrowth of cells into the pores. The size of the pores may be selected for particular cell types of interest and/or for the amount of ingrowth desired. In some embodiments, the particles comprise the antigen of interest without other non-peptide active agents, such as drugs or immunomodulators. Furthermore, in some embodiments the particles of the invention do not contain immunostimulatory or immunosuppressive peptides in addition to the antigen of interest. Furthermore, in some embodiments, the particles do not contain other proteins or peptides (e.g. costimulatory molecules, MHC molecules, immunostimulatory peptides or immunosuppressive peptides) either on the surface or encapsulated within the particle.

Encapsulation of the antigen, biological, and/or chemical agents in the particle of the invention has been surprisingly found to induce immunological tolerance and has several advantages. First, the encapsulated particles have a slower cytokine response. Second, when using multiple antigens, biological, and/or chemical agents, encapsulation removes the competition between these various molecules that might occur if the agents were attached to the surface of the particle. Third, encapsulation allows more antigens, biological, and/or chemical agents to be incorporated with the particle. Fourth, encapsulation allows for easier use of complex protein antigens or organ homogenates (e.g. pancreas homogenate for type 1 diabetes or peanut extract in peanut allergy). Finally, encapsulation of antigens, biological, and/or chemical agents within the particle instead of conjugation to the surface of the particle maintains the net negative charge on the surface of the particle. The encapsulation of the antigen, biological, and/or chemical agents in the particles of the invention may be performed by any method known in the art. In one embodiment, polypeptide antigens are encapsulated in the particles by a double-emulsion process. In a further embodiment, the polypeptide antigens are water soluble.

In another embodiment, the polypeptide antigens are encapsulated in the particles by a single-emulsion process. In a further embodiment, the polypeptide antigens are more hydrophobic. Sometimes, the double emulsion process leads to the formation of large particles which may result in the leakage of the hydrophilic active component and low entrapment efficiencies. The coalescence and Ostwald ripening are two mechanisms that may destabilize the double-emulsion droplet, and the diffusion through the organic phase of the hydrophilic active component is the main mechanism responsible of low levels of entrapped active component. In some embodiments, it may be beneficial to reduce the nanoparticle size. One strategy to accomplish this is to apply a second strong shear rate. The leakage effect can be reduced by using a high polymer concentration and a high polymer molecular mass, accompanied by an increase in the viscosity of the inner water phase and in increase in the surfactant molecular mass.

In certain embodiments, the present invention provides carriers having thereon (or therein) cells or other biological or chemical agents. Where cells are employed, the carriers are not limited to a particular type of cells. In some embodiments, the carriers have thereon pancreatic islet cells. In some embodiments, the microporous carriers additionally have thereon ECM proteins and/or exendin-4. The carriers are not limited to a particular type. In some embodiments, a carrier has regions of varying porosity (e.g., varying pore size, pore depth, and/or pore density). In some embodiments, carriers have thereon (or therein) pharmaceutical agents, DNA, RNA, extracellular matrix proteins, exendin-4, etc. In certain embodiments, the present invention provides methods for transplanting pancreatic islet cells with such carriers. In certain embodiments of this invention, the inducing antigen is a single isolated or recombinantly produced molecule. For treating conditions where the target antigen is disseminated to various locations in the host, it is generally necessary that the inducing antigen be identical to or immunologically related to the target antigen. Examples of such antigens are most polynucleotide antigens, and some carbohydrate antigens (such as blood group antigens).

Any suitable antigens may find use within the scope of the present invention. In some embodiments, the inducing antigen contributes to the specificity of the tolerogenic response that is induced. The inducing antigen may or may not be the same as the target antigen, which is the antigen present or to be placed in the subject being treated which is a target for the unwanted immunological response, and for which tolerance is desired.

Where the target antigen is preferentially expressed on a particular organ, cell, or tissue type, the practitioner again has the option of using an inducing antigen which is identical with or immunologically related to the target antigen. However, there is also the additional option of using an antigen which is a bystander for the target. This is an antigen which may not be immunologically related to the target antigen, but is preferentially expressed in a tissue where the target antigen is expressed. A working theory as to the effectiveness of bystander suppression is that suppression is an active cell-mediated process that down-regulates the effector arm of the immune response at the target cells. The suppressor cells are specifically stimulated by the inducer antigen at the mucosal surface, and home to a tissue site where the bystander antigen is preferentially expressed. Through an interactive or cytokine-mediated mechanism, the localized suppressor cells then down-regulate effector cells (or inducers of effector cells) in the neighborhood, regardless of what they are reactive against. If the effector cells are specific for a target different from the inducing antigen, then the result is a bystander effect. For further elaboration of the bystander reaction and a list of tolerogenic peptides having this effect, the reader is referred to International Patent Publication WO 93/16724. An implication of bystander theory is that one of ordinary skill need not identify or isolate a particular target antigen against which tolerance is desired in order to practice the present invention. The practitioner need only be able to obtain at least one molecule preferentially expressed at the target site for use as an inducing antigen.

In certain embodiments of this invention, the inducing antigen is not in the same form as expressed in the individual being treated, but is a fragment or derivative thereof. Inducing antigens of this invention include peptides based on a molecule of the appropriate specificity but adapted by fragmentation, residue substitution, labeling, conjugation, and/or fusion with peptides having other functional properties. The adaptation may be performed for any desirable purposes, including but not limited to the elimination of any undesirable property, such as toxicity or immunogenicity; or to enhance any desirable property, such as mucosal binding, mucosal penetration, or stimulation of the tolerogenic arm of the immune response. Terms such as insulin peptide, collagen peptide, and myelin basic protein peptide, as used herein, refer not only to the intact subunit, but also to allotypic and synthetic variants, fragments, fusion peptides, conjugates, and other derivatives that contain a region that is homologous (preferably 70% identical, more preferably 80% identical and even more preferably 90% identical at the amino acid level) to at least 10 and preferably 20 consecutive amino acids of the respective molecule for which it is an analog, wherein the homologous region of the derivative shares with the respective parent molecule an ability to induce tolerance to the target antigen.

It is recognized that tolerogenic regions of an inducing antigen are often different from immunodominant epitopes for the stimulation of an antibody response. Tolerogenic regions are generally regions that can be presented in particular cellular interactions involving T cells. Tolerogenic regions may be present and capable of inducing tolerance upon presentation of the intact antigen. Some antigens contain cryptic tolerogenic regions, in that the processing and presentation of the native antigen does not normally trigger tolerance. An elaboration of cryptic antigens and their identification is found in International Patent Publication WO 94/27634.

In certain embodiments of this invention, two, three, or a higher plurality of inducing antigens is used. It may be desirable to implement these embodiments when there are a plurality of target antigens, or to provide a plurality of bystanders for the target. For example, both insulin and glucagon can be mixed with a mucosal binding component in the treatment of diabetes. It may also be desirable to provide a cocktail of antigens to cover several possible alternative targets. For example, a cocktail of histocompatibility antigen fragments could be used to tolerize a subject in anticipation of future transplantation with an allograft of unknown phenotype. Allovariant regions of human leukocyte antigens are known in the art: e.g., Immunogenetics 29:231, 1989. In another example, a mixture of allergens may serve as inducing antigen for the treatment of atopy.

Inducing antigens can be prepared by a number of techniques known in the art, depending on the nature of the molecule. Polynucleotide, polypeptide, and carbohydrate antigens can be isolated from cells of the species to be treated in which they are enriched. Short peptides are conveniently prepared by amino acid synthesis. Longer proteins of known sequence can be prepared by synthesizing an encoding sequence or PCR-amplifying an encoding sequence from a natural source or vector, and then expressing the encoding sequence in a suitable bacterial or eukaryotic host cell.

In certain embodiments of this invention, the combination comprises a complex mixture of antigens obtained from a cell or tissue, one or more of which plays the role of inducing antigen. The antigens may be in the form of whole cells, either intact or treated with a fixative such as formaldehyde, glutaraldehyde, or alcohol. The antigens may be in the form of a cell lysate, created by detergent solubilization or mechanical rupture of cells or tissue, followed by clarification. The antigens may also be obtained by subcellular fractionation, particularly an enrichment of plasma membrane by techniques such as differential centrifugation, optionally followed by detergent solubilization and dialysis. Other separation techniques are also suitable, such as affinity or ion exchange chromatography of solubilized membrane proteins.

In one embodiment, the antigenic peptide or protein is an autoantigen, an alloantigen or a transplantation antigen. In yet another particular embodiment, the autoantigen is selected from the group consisting of myelin basic protein, collagen or fragments thereof, DNA, nuclear and nucleolar proteins, mitochondrial proteins and pancreatic β-cell proteins.

The invention provides for the induction of tolerance to an autoantigen for the treatment of autoimmune diseases by administering the antigen for which tolerance is desired. For example, autoantibodies directed against the myelin basic protein (MBP) are observed in patients with multiple sclerosis, and, accordingly, MBP antigenic peptides or proteins may be used in the invention to be delivered using the compositions of the present invention to treat and prevent multiple sclerosis.

By way of another non-limiting example, an individual who is a candidate for a transplant from a non-identical twin may suffer from rejection of the engrafted cells, tissues or organs, as the engrafted antigens are foreign to the recipient. Prior tolerance of the recipient individual to the intended graft abrogates or reduces later rejection. Reduction or elimination of chronic anti-rejection therapies may be achieved by the practice of the present invention. In another example, many autoimmune diseases are characterized by a cellular immune response to an endogenous or self-antigen. Tolerance of the immune system to the endogenous antigen is desirable to control the disease.

In a further example, sensitization of an individual to an industrial pollutant or chemical, such as may be encountered on-the-job, presents a hazard of an immune response. Prior tolerance of the individual's immune system to the chemical, in particular in the form of the chemical reacted with the individual's endogenous proteins, may be desirable to prevent the later occupational development of an immune response.

Allergens are other antigens for which tolerance of the immune response thereto is also desirable. In one embodiment, the antigen is a gliaden. In a further embodiment, the antigen is A-gliaden.

Notably, even in diseases where the pathogenic autoantigen is unknown, bystander suppression may be induced using antigens present in the anatomical vicinity. For example, autoantibodies to collagen are observed in rheumatoid arthritis and, accordingly, a collagen-encoding gene may be utilized as the antigen-expressing gene module in order to treat rheumatoid arthritis (see e.g. Choy (2000) Curr Opin Investig Drugs 1:58-62). Furthermore, tolerance to beta cell autoantigens may be utilized to prevent development of type 1 diabetes (see e.g. Bach and Chatenoud (2001) Ann Rev Immunol 19:131-161).

As another example, auto-antibodies directed against myelin oligodendrocyte glycoprotein (MOG) are observed in autoimmune encephalomyelitis and in many other CNS diseases as well as multiple sclerosis (see e.g. Iglesias et al. (2001) Glia 36:22-34). Accordingly, use of MOG antigen expressing constructs in the invention allows for treatment of multiple sclerosis as well as related autoimmune disorders of the central nervous system.

Still other examples of candidate autoantigens for use in treating autoimmune disease include: pancreatic beta-cell antigens, insulin and GAD to treat insulin-dependent diabetes mellitus; collagen type 11, human cartilage gp 39 (HCgp39) and gp130-RAPS for use in treating rheumatoid arthritis; myelin basic protein (MBP), proteo lipid protein (PLP) and myelin oligodendrocyte glycoprotein (MOG, see above) to treat multiple sclerosis; fibrillarin, and small nucleolar protein (snoRNP) to treat scleroderma; thyroid stimulating factor receptor (TSH-R) for use in treating Graves' disease; nuclear antigens, histones, glycoprotein gp70 and ribosomal proteins for use in treating systemic lupus erythematosus; pyruvate dehydrogenase dehydrolipoamide acetyltransferase (PCD-E2) for use in treating primary billiary cirrhosis; hair follicle antigens for use in treating alopecia areata; and human tropomyosin isoform 5 (hTM5) for use in treating ulcerative colitis.

In one embodiment, the particles of the invention are covalently coupled to antigens comprising one or more epitopes associated with allergies, autoimmune diseases and/or inflammatory diseases or disorders. The antigens may comprise one or more copies of an epitope. In one embodiment, the antigens comprise a single epitope associated with one disease or disorder. In a further embodiment, the antigens comprise more than one epitope associated with the same disease or disorder. In yet a further embodiment, the antigens comprise more than one epitope associated with different diseases or disorders. In a further embodiment, the antigens comprise one or more epitopes associated with one or more allergies. In a further embodiment, the antigens comprise one or more epitopes associated with multiple sclerosis, type 1 diabetes. Celiac's disease, and/or inflammatory bowel disease, including Crohn's disease or ulcerative colitis. In one embodiment, the epitopes are from myelin basic protein (e.g. SEQ ID NOs:4975 & 4976), proteolipid protein (e.g. SEQ ID NO: 4977), myelin oligodendrocyte glycoprotein (e.g. SEQ ID NOs: 1 & 4978), aquaporin, (e.g. SEQ ID NO: 4979), myelin associated glycoprotein (e.g. SEQ ID NO: 4980), insulin (e.g. SEQ ID NO: 4981), glutamic acid decarboxylase (e.g. SEQ ID NO: 4982), gliadin (e.g. SEQ ID NOs:4983-4985 or 5136-5140), the α3 chain of type IV collagen (e.g. SEQ ID NO: 5017), or fragments, homologs, or isoforms thereof. In a further embodiment, the epitopes are from gluten, including from gliadin and/or glutenin. In one embodiment, the epitopes are from insulin homologs, such as those described in U.S. Pat. No. 8,476,228 hereby incorporated in its entirety for all purposes. In one embodiment, the gliaden epitopes are SEQ ID NOs: 13, 14, 16, 320, or 321 in U.S. Application No. 20110293644, hereby incorporated in its entirety for all purposes.

Further non-limiting examples of epitopes associated with various autoimmune diseases and/or inflammatory diseases or disorders that are contemplated by the instant invention are described in Tables 2 and 3.

TABLE 2

Representative Linear Epitopes

| Disease | Representative Epitopes |
| --- | --- |
| Multiple Sclerosis | SEQ ID NOs: 2-1294 |
| Celiac Disease | SEQ ID NOs: 1295-1724; |
| | SEQ ID NOs: 1726-1766; |
| | SEQ ID NOs: 4986-5140 |

TABLE 2-continued

Representative Linear Epitopes

| Disease | Representative Epitopes |
|---|---|
| Diabetes | SEQ ID NOs: 1767-1840; |
| | SEQ ID NOs: 1842-1962; |
| | SEQ ID NOs: 1964-2027; |
| | SEQ ID NOs: 2029-2073; |
| | SEQ ID NOs: 2075-2113; |
| | SEQ ID NOs: 2115-2197; |
| | SEQ ID NOs: 2199-2248; |
| | SEQ ID NOs: 2250-2259; |
| | SEQ ID NOs: 2261-2420; |
| | SEQ ID NOs: 2422-2486; |
| | SEQ ID NOs: 2489-2505 |
| Rheumatoid Arthritis | SEQ ID NOs: 2506-3260; |
| | SEQ ID NOs: 3262-3693 |
| Systemic Lupus Erythematosus | SEQ ID NOs: 3694-3857; |
| | SEQ ID NOs: 3860-4565 |
| Good Pasture's Syndrome | SEQ ID NOs: 4566-4576; |
| | SEQ ID NOs: 4578-4610; |
| | SEQ ID NOs: 4612-4613; |
| | SEQ ID NOs: 5018-5039 |
| Autoimmune Uveitis | SEQ ID NOs: 4614-4653 |
| Autoimmune Thyroiditis | SEQ ID NOs: 4654-4694; |
| | SEQ ID NOs: 4696-4894; |
| | SEQ ID NOs: 4896-4901 |
| Autoimmune Myositis | SEQ ID NOs: 4902-4906 |
| Autoimmune Vasculitis | SEQ ID NOs: 4907-4914 |
| Autoimmune Pancreatitis | SEQ ID NOs: 4915-4917 |
| Crohns Disease | SEQ ID NOs: 4918-4941 |
| Ulcerative Colitis | SEQ ID NOs: 4942-4952 |
| Psoriasis | SEQ ID NOs: 4953-4963 |
| Reactive Arthritis | SEQ ID NOs: 4964-4974 |

Not all epitopes are linear epitopes; epitopes can also be discontinuous, conformational epitopes. A number of discontinuous epitopes associated with autoimmune diseases or inflammatory diseases and/or disorders are known. Non-limiting examples of discontinuous epitopes are described in Table 3.

TABLE 3

Representative Discontinuous Epitopes

| Disease | Epitope | Full Length Polypeptide |
|---|---|---|
| Celiac Disease | D151, E153, E154, E155, E158; | Protein-glutamine gamma-glutamyltransferase 2 |
| | D306, N308, N310; | SEQ ID NO: 1725 |
| | D434, E435, E437, D438; | |
| | E329; | |
| | E153; | |
| | R19, E153, M659; or | |
| | C277, H335, D358 | |
| Diabetes | E517; | Glutamate decarboxylase 2 |
| | R255, F256, K257, K263, E264, K265, L270, P271, R272, L273, L285, K286, K287, I294, G295, T296, D297, S298, R317, R318; N483, I484, I485, K486, N487, R488, E489, G490, Y491, E492, M493, V494, F495, D496, G497, K498, P499, F556, F557, R558, M559, V560, I561, S562, N563, P564, A565, A566, T567, H568, Q569, D570, I571, D572, F573, L574, I575, E576, E577, I578, E579, R580, L581, G582, Q583, D584, L585; | SEQ ID NOs: 1841, 1963, 2114, & 2249 |
| | E264; | |
| | E517, E520, E521, S524, S527, V532; | |
| | E517, E521; | |
| | K358; | |
| | R536, Y540 | |
| Diabetes | P876, A877, E878, T880; | protein tyrosine phosphatase, receptor type, N precursor |
| | T804; | SEQ ID NOs: 2028 & 2074 |
| | T804, V813, D821, R822, Q862, P886; | |
| | T804, V813, D821, R822, Q862, P886; | |
| | W799, E836, N858; | |
| | D911; | |
| | Q862; | |
| | L831, H833, V834, E836, Q860; | |
| | W799, E836, N858; | |
| | W799, L831, H833, V834, Y835, E836, Q860; | |

TABLE 3-continued

Representative Discontinuous Epitopes

| Disease | Epitope | Full Length Polypeptide |
|---|---|---|
| Diabetes | R325, R332, E333, K336, K340; R325; W325 | zinc transporter 8 isoform a SEQ ID NO: 2421 |
| Diabetes | E872, C945 | Receptor-type tyrosine-protein phosphatase N2 SEQ ID NOs: 2198, 2260, & 2487 |
| Diabetes | W799, C909 | tyrosine phosphatase SEQ ID NO: 2488 |
| Rheumatoid Arthritis | L14, M15, I16, S17, R18, N147, G148, S187, M191, H196, N197, H198, Y199, Q201, S203 | Chain A, Crystal Structure Of A Human Igm Rheumatoid Factor Fab In Complex With Its Autoantigen Igg Fc SEQ ID NO: 3261 |
| Systemic Lupus Erythematosus | K591, S592, G593 | ATP-dependent DNA helicase 2 subunit 1 SEQ ID NO: 3858 |
| Systemic Lupus Erythematosus | M1, K2, L3, V4, R5, F6, L7, M8, K9, L10, S11, H12, E13, T14, V15, T16, I17, E18, L19, K20, N21, G22, T23, Q24, V25, H26, P85, K86, V87, K88, S89, K90, K91, R92, E93, A94, V95, A96, G97, R98, G99, R100, G101, R102, G103, R104, G105, R106, G107, R108, G109, R110, G111, R112, G113, R114, G115, G116, P117, R118, R119 | Small nuclear ribonucleoprotein Sm D1 SEQ ID NO: 3859 |
| Systemic Lupus Erythematosus | G59, R62 | beta-2-glycoprotein I SEQ ID NO: 4357 |
| Good Pasture's Syndrome | T24, A25, I26, S28, E31, V34, P35, S38, Q64 | type IV collagen alpha3 chain SEQ ID NO: 4577 |
| Good Pasture's Syndrome | T1455, A1456, I1457, S1459, E1462, T1464, V1465, P1466, Y1468, S1469, Q1495, T1537, T1565, P1569, H1572, K1579, A1634 | alpha3 type IV collagen SEQ ID NO: 4611 |
| Autoimmune Thyroiditis | E604, D620, K627, D630; R225, R646, D707; K627; R225; Y772; K713, F714, P715, E716; P715, D717 | Thyroid peroxidase SEQ ID NO: 4695 |
| Autoimmune Thyroiditis | D36, R38, K42, Q55, K58, I60, E61, R80, Y82, S84, T104, H105, E107, R109, N110, K129, F130, D151, F153, I155, E157, T181, K183, D203 | Thyrotropin receptor SEQ ID NO: 4895 |

Combinations of antigens and/or epitopes can be tested for their ability to promote tolerance by conducting experiments with isolated cells or in animal models.

In some embodiments, the tolerance inducing compositions of the present invention contain an immune modulating agent, such as rapamycin, tacrolimus, In some embodiments, the tolerance inducing compositions of the present invention contain an immune modulating agent such as a Janus Kinase antagonist and/or a Janus Kinase agonist.

In some embodiments, the tolerance inducing compositions of the present invention contain an immune modulating agent such as a cytokine and/or antibody to a cytokine.

In some embodiments, the tolerance inducing compositions of the present invention contain growth factors that may promote regulation of T cells. Such factors may include insulin, transforming growth factor beta, serum albumin and any other factor known to support immune cell regulation.

In some embodiments, the tolerance inducing compositions of the present invention contain antibodies that may promote tolerance induction.

In some embodiments, the tolerance inducing compositions of the present invention contain an apoptosis signaling molecule (e.g., in addition to an antigenic peptide or other antigenic molecule). In some embodiments, the apoptosis signaling molecule is coupled and/or associated with the surface of the carrier. In some embodiments an apoptotic signaling molecules allows a carrier to be perceived as an apoptotic body by antigen presenting cells of the host, such as cells of the host reticuloendothelial system; this allows presentation of the associated peptide epitopes in a tolerance-inducing manner. Without being bound by theory, this is presumed to prevent the upregulation of molecules involved in immune cell stimulation, such as MHC class I/II, and costimulatory molecules. These apoptosis signaling molecules may also serve as phagocytic markers. For example, apoptosis signaling molecules suitable for the present invention have been described in US Pat App No. 20050113297, which is hereby incorporated by reference in its entirety. Molecules suitable for the present invention include molecules that target phagocytes, which include macrophages, dendritic cells, monocytes, granulocytes and neutrophils.

In some embodiments, molecules suitable as apoptotic signalling molecules act to enhance tolerance of the associated peptides. Additionally, a carrier bound to an apoptotic signaling molecule can be bound by C1q in apoptotic cell recognition (Paidassi et al., (2008) J. Immunol. 180:2329-2338; herein incorporated by reference in its entirety). For example, molecules that may be useful as apoptotic signalling molecules include phosphatidyl serine, annexin-1, annexin-5, milk fat globule-EGF-factor 8 (MFG-E8), or the family of thrombospondins (e.g., thrombospondin-1 (TSP-1)). Various molecules suitable for use as apoptotic signalling molecules with the present invention are discussed, for example, in U.S. Pat. App. 2012/0076831; herein incorporated by reference in its entirety).

In some embodiments, the apoptotic signalling molecule may be conjugated to the antigen-specific peptide. In some instances, the apoptotic signalling molecule and antigen-specific peptide are conjugated by the creation of a fusion protein. For example a fusion protein may comprise at least one antigen-specific peptide (or a fragment or a variant thereof) coupled to at least one molecule of an apoptotic signalling molecule (or a fragment or a variant thereof). For the creation of fusion proteins, the terms "fusion protein," "fusion peptide," "fusion polypeptide," and "chimeric peptide" are used interchangeably. Suitable fragments of the antigen-specific peptide include any fragment of the full-length peptide that retains the function of generating the desired antigen-specific tolerance function of the present invention. The fusion protein may be created by various means understood in the art (e.g., genetic fusion, chemical conjugation, etc.). The two proteins may be fused either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. A peptide linker sequence may be employed to separate the first and second polypeptide components by a distance sufficient to ensure that each polypeptide folds into its secondary and tertiary structures. Amino acid sequences which may be usefully employed as linkers include those disclosed in Maratea et. al., Gene 40:39-46 (1985); Murphy et al., Proc. Natl. Acad. Sci. USA 83:8258-8262 (1986); U.S. Pat. Nos. 4,935,233 and 4,751,180; herein incorporated by reference in their entireties. The linker sequence may generally be from 1 to about 50 amino acids in length. In some embodiments, linker sequences are not required and/or utilized, for example, when the first and second polypeptides have non-essential N-terminal amino acid regions that can be used to separate the functional domains and prevent steric interference.

A proxy for tolerogenic activity is the ability of an intact antigen or fragment to stimulate the production of an appropriate cytokine at the target site. The immunoregulatory cytokine released by T suppressor cells at the target site is thought to be TGF-β (Miller et al., Proc. Natl. Acad. Sci. USA 89:421, 1992). Other factors that may be produced during tolerance are the cytokines IL4 and IL-10, and the mediator PGE. In contrast, lymphocytes in tissues undergoing active immune destruction secrete cytokines such as IL-1, IL-2, IL-6, and γ-IFN. Hence, the efficacy of a candidate inducing antigen can be evaluated by measuring its ability to stimulate the appropriate type of cytokines.

With this in mind, a rapid screening test for tolerogenic epitopes of the inducing antigen, effective mucosal binding components, effective combinations, or effective modes and schedules of mucosal administration can be conducted using syngeneic animals as donors for in vitro cell assays. Animals are treated at a mucosal surface with the test composition, and at some time are challenged with parenteral administration of the target antigen in complete Freund's adjuvant. Spleen cells are isolated, and cultured in vitro in the presence of the target antigen at a concentration of about 50 μg/mL. Target antigen can be substituted with candidate proteins or sub-fragments to map the location of tolerogenic epitopes. Cytokine secretion into the medium can be quantitated by standard immunoassay.

The ability of the cells to suppress the activity of other cells can be determined using cells isolated from an animal immunized with the target antigen, or by creating a cell line responsive to the target antigen (Ben-Nun et al., Eur. J. Immunol. 11:195, 1981, herein incorporated by reference in its entirety). In one variation of this experiment, the suppressor cell population is mildly irradiated (about 1000 to 1250 rads) to prevent proliferation, the suppressors are co-cultured with the responder cells, and then tritiated thymidine incorporation (or MTT) is used to quantitate the proliferative activity of the responders. In another variation, the suppressor cell population and the responder cell population are cultured in the upper and lower levels of a dual chamber transwell culture system (Costar, Cambridge Mass.), which permits the populations to coincubate within 1 mm of each other, separated by a polycarbonate membrane (WO 93/16724). In this approach, irradiation of the suppressor cell population is unnecessary, since the proliferative activity of the responders can be measured separately.

In embodiments of the invention where the target antigen is already present in the individual, there is no need to isolate the antigen or precombine it with the mucosal binding component. For example, the antigen may be expressed in the individual in a certain fashion as a result of a pathological condition (such as inflammatory bowel disease or Celiac disease) or through digestion of a food allergen. Testing is performed by giving the mucosal binding component in one or more doses or formulations, and determining its ability to promote tolerization against the antigen in situ.

The effectiveness of compositions and modes of administration for treatment of specific disease can also be elaborated in a corresponding animal disease model. The ability of the treatment to diminish or delay the symptomatology of the disease is monitored at the level of circulating biochemical and immunological hallmarks of the disease, immunohistology of the affected tissue, and gross clinical features as appropriate for the model being employed. Non-limiting examples of animal models that can be used for testing are included in the following section.

The invention contemplates modulation of tolerance by modulating TH1 response, TH2 response, TH17 response, or a combination of these responses. Modulating TH1 response encompasses changing expression of, e.g., interferon-gamma. Modulating TH2 response encompasses changing expression of, e.g., any combination of IL-4, IL-5, IL-10, and IL-13. Typically an increase (decrease) in TH2 response will comprise an increase (decrease) in expression of at least one of IL-4, IL-5, IL-10, or IL-13; more typically an increase (decrease) in TH2 response will comprise an increase in expression of at least two of IL-4, IL-5, IL-10, or EL-13, most typically an increase (decrease) in TH2 response will comprise an increase in at least three of DL-4, IL-5, IL-10, or IL-13, while ideally an increase (decrease) in TH2 response will comprise an increase (decrease) in expression of all of IL-4, IL-5, IL-10, and IL-13. Modulating TH 17 encompasses changing expression of, e.g., TGF-beta, IL-6, IL-21 and IL23, and effects levels of IL-17, IL-21 and IL-22.

Other suitable methods for assessing the effectiveness of compositions and methods of the present invention are understood in the art, as are discussed, for example, in U.S. Pat. App. 2012/0076831 (herein incorporated by reference in its entirety).

Certain embodiments of this invention relate to priming of immune tolerance in an individual not previously tolerized by therapeutic intervention. These embodiments generally involve a plurality of administrations of a combination of antigen and mucosal binding component. Typically, at least three administrations, frequently at least four administrations, and sometimes at least six administrations are performed during priming in order to achieve a long-lasting result, although the subject may show manifestations of tolerance early in the course of treatment. Most often, each dose is given as a bolus administration, but sustained formulations capable of mucosal release are also suitable. Where multiple administrations are performed, the time between administrations is generally between 1 day and 3 weeks, and typically between about 3 days and 2 weeks. Generally, the same antigen and mucosal binding component are present at the same concentration, and the administration is given to the same mucosal surface, but variations of any of these variables during a course of treatment may be accommodated.

Other embodiments of this invention relate to boosting or extending the persistence of a previously established immune tolerance. These embodiments generally involve one administration or a short course of treatment at a time when the established tolerance is declining or at risk of declining. Boosting is generally performed 1 month to 1 year, and typically 2 to 6 months after priming or a previous boost. This invention also includes embodiments that involve regular maintenance of tolerance on a schedule of administrations that occur semiweekly, weekly, biweekly, or on any other regular schedule.

The particles of the current invention can be given in any dose effective to dampen the inflammatory immune response in a subject in need thereof or to treat a bacterial or viral infection in a subject in need thereof. In certain embodiments, about $10^2$ to about $10^{20}$ particles are provided to the individual. In a further embodiment between about $10^3$ to about $10^{15}$ particles are provided. In yet a further embodiment between about $10^6$ to about $10^{12}$ particles are provided. In still a further embodiment between about $10^8$ to about $10^{10}$ particles are provided. In a preferred embodiment the preferred dose is 0.1% solids/ml. Therefore, for 0.5 μm beads, a preferred dose is approximately $4 \times 10^9$ beads, for 0.05 μm beads, a preferred dose is approximately $4 \times 10^{12}$ beads, for 3 μm beads, a preferred dose is $2 \times 10^7$ beads. In some embodiments, the particle dose is about 25 mg/mL to about 50 mg/mL. In some embodiments, the particle dose is about 50 mg/mL to about 100 mg/mL. In some embodiments, the particle dose is about 100 mg/mL to about 150 mg/mL. In some embodiments, the particle dose is about 150 mg/mL to about 200 mg/mL. In some embodiments, the particle dose is about 200 mg/mL to about 250 mg/mL. In some embodiments, the particle dose is about 250 mg/mL to about 300 mg/mL. In some embodiments, the particle dose is about 300 mg/mL or more. However, any dose that is effective in treating the particular condition to be treated is encompassed by the current invention.

The invention is useful for treatment of immune related disorders such as autoimmune disease, transplant rejection, enzyme deficiencies and allergic reactions. Substitution of a synthetic, biocompatible particle system to induce immune tolerance could lead to ease of manufacturing, broad availability of therapeutic agents, increase uniformity between samples, increase the number of potential treatment sites and dramatically reduce the potential for allergic responses to a carrier cell.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages. Immune cells involved in the immune response include lymphocytes, such as B cells and T cells (CD4$^+$, CD8$^+$, Th1 and Th2 cells); antigen presenting cells (e.g., professional antigen presenting cells such as dendritic cells, macrophages, B lymphocytes, Langerhans cells, and nonprofessional antigen presenting cells such as keratinocytes, endothelial cells, astrocytes, fibroblasts, oligodendrocytes); natural killer cells; myeloid cells, such as macrophages, eosinophils, mast cells, basophils, and granulocytes. In some embodiments, the modified particles of the present invention are effective to reduce inflammatory cell trafficking to the site of inflammation.

As used herein, the term "anergy," "tolerance," or "antigen-specific tolerance" refers to insensitivity of T cells to T cell receptor-mediated stimulation. Such insensitivity is generally antigen-specific and persists after exposure to the antigenic peptide has ceased. For example, anergy in T cells is characterized by lack of cytokine production, e.g., IL-2. T-cell anergy occurs when T cells are exposed to antigen and receive a first signal (a T cell receptor or CD-3 mediated signal) in the absence of a second signal (a costimulatory signal). Under these conditions, re-exposure of the cells to the same antigen (even if re-exposure occurs in the presence of a costimulatory molecule) results in failure to produce cytokines and subsequently failure to proliferate. Thus, a failure to produce cytokines prevents proliferation. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate DL-2 gene transcription induced by a heterologous promoter under the control of the 5' IL-2 gene enhancer or by a multimer of the API sequence that can be found within the enhancer (Kang et al. 1992 Science. 257:1134).

As used herein, the term "immunological tolerance" refers to methods performed on a proportion of treated subjects in comparison with untreated subjects where: a) a decreased level of a specific immunological response (thought to be mediated at least in part by antigen-specific effector T lymphocytes, B lymphocytes, antibody, or their equivalents); b) a delay in the onset or progression of a specific immunological response; or c) a reduced risk of the onset or progression of a specific immunological response. "Specific" immunological tolerance occurs when immunological tolerance is preferentially invoked against certain antigens in comparison with others. "Non-Specific" immunological tolerance occurs when immunological tolerance is invoked indiscriminately against antigens which lead to an inflammatory immune response. "Quasi-Specific" immunological tolerance occurs when immunological tolerance is invoked semi-discriminately against antigens which lead to a pathogenic immune response but not to others which lead to a protective immune response.

Tolerance to autoantigens and autoimmune disease is achieved by a variety of mechanisms including negative selection of self-reactive T cells in the thymus and mechanisms of peripheral tolerance for those autoreactive T cells that escape thymic deletion and are found in the periphery. Examples of mechanisms that provide peripheral T cell tolerance include "ignorance" of self-antigens, anergy or unresponsiveness to autoantigen, cytokine immune deviation, and activation-induced cell death of self-reactive T cells. In addition, regulatory T cells have been shown to be involved in mediating peripheral tolerance. See, for example, Walker et al. (2002) Nat. Rev. Immunol. 2: 11-19; Shevach et al. (2001) Immunol. Rev. 182:58-67. In some situations, peripheral tolerance to an autoantigen is lost (or broken) and an autoimmune response ensues. For example, in an animal model for EAE, activation of antigen presenting cells (APCs) through TLR innate immune receptors was shown to break self-tolerance and result in the induction of EAE (Waldner et al. (2004) J. Clin. Invest. 113:990-997).

Accordingly, in some embodiments, the invention provides methods for increasing antigen presentation while suppressing or reducing TLR7/8, TLR9, and/or TLR 7/8/9 dependent cell stimulation. As described herein, administration of particular modified particles results in antigen presentation by DCs or APCs while suppressing the TLR 7/8, TLR9, and/or TLR7/8/9 dependent cell responses associated with immunostimulatory polynucleotides. Such suppression may include decreased levels of one or more TLR-associated cytokines.

As discussed above this invention provides novel compounds that have biological properties useful for the treatment of Mac-1 and LFA-1 mediated disorders.

Pharmaceutical Compositions

Accordingly, in another aspect of the present invention, pharmaceutical compositions are provided, which comprise the tolerizing immune modifying particles and optionally comprise a pharmaceutically acceptable carrier. In certain embodiments, these compositions optionally further comprise one or more additional therapeutic agents. Alternatively, the modified particles of the current invention may be administered to a patient in need thereof in combination with the administration of one or more other therapeutic agents. For example, additional therapeutic agents for conjoint administration or inclusion in a pharmaceutical composition with a compound of this invention may be an approved anti-inflammatory agent, or it may be any one of a number of agents undergoing approval in the Food and Drug Administration that ultimately obtain approval for the treatment of any disorder characterized by an uncontrolled inflammatory immune response or a bacterial or viral infection. It will also be appreciated that certain of the modified particles of present invention can exist in free form for treatment, or where appropriate, as a pharmaceutically acceptable derivative thereof.

The pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The particles of the invention may be administered orally, nasally, intravenously, intramuscularly, ocularly, transdermally, intraperitoneally, or subcutaneously. In one embodiment, the particles of the invention are administered intravenously.

Administration

The effective amounts and method of administration of the present invention for modulation of an immune response can vary based on the individual, what condition is to be treated and other factors evident to one skilled in the art. Factors to be considered include route of administration and the number of doses to be administered. Such factors are known in the art and it is well within the skill of those in the art to make such determinations without undue experimentation. A suitable dosage range is one that provides the desired regulation of immune. Useful dosage ranges of the carrier, given in amounts of carrier delivered, may be, for example, from about any of the following: 0.5 to 10 mg/kg, 1 to 9 mg/kg, 2 to 8 mg/kg, 3 to 7 mg/kg, 4 to 6 mg/kg, 5 mg/kg, 1 to 10 mg/kg, 5 to 10 mg/kg. Alternatively, the dosage can be administered based on the number of particles. For example, useful dosages of the carrier, given in amounts of carrier delivered, may be, for example, about $10^6$, $10^7$, $10^8$, $10^9$, $10^{10}$, or greater number of particles per dose. The absolute amount given to each patient depends on pharmacological properties such as bioavailability, clearance rate and route of administration. Details of pharmaceutically acceptable carriers, diluents and excipients and methods of preparing pharmaceutical compositions and formulations are provided in Remington's Pharmaceutical Sciences $18^{th}$ Edition, 1990, Mack Publishing Co., Easton, Pa., USA., which is hereby incorporated by reference in its entirety.

The effective amount and method of administration of the particular carrier formulation can vary based on the individual patient, desired result and/or type of disorder, the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient IRP-containing composition to attain a tissue concentration of about 1-50 µM as measured by blood levels. The absolute amount given to each patient depends on pharmacological properties such as bioavailability, clearance rate and route of administration.

The present invention provides carrier formulations suitable for topical application including, but not limited to, physiologically acceptable implants, ointments, creams, rinses and gels. Exemplary routes of dermal administration are those which are least invasive such as transdermal transmission, epidermal administration and subcutaneous injection.

Transdermal administration is accomplished by application of a cream, rinse, gel, etc. capable of allowing the carrier to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

Parenteral routes of administration include but are not limited to electrical (iontophoresis) or direct injection such as direct injection into a central venous line, intravenous, intramuscular, intraperitoneal, intradermal, or subcutaneous injection. Formulations of carrier suitable for parenteral administration are generally formulated in USP water or water for injection and may further comprise pH buffers, salts bulking agents, preservatives, and other pharmaceutically acceptable excipients. Immunoregulatory polynucleotide for parenteral injection may be formulated in pharmaceutically acceptable sterile isotonic solutions such as saline and phosphate buffered saline for injection.

Gastrointestinal routes of administration include, but are not limited to, ingestion and rectal routes and can include the use of, for example, pharmaceutically acceptable powders, pills or liquids for ingestion and suppositories for rectal administration.

Naso-pharyngeal and pulmonary administration include are accomplished by inhalation, and include delivery routes such as intranasal, transbronchial and transalveolar routes. The invention includes formulations of carrier suitable for administration by inhalation including, but not limited to, liquid suspensions for forming aerosols as well as powder forms for dry powder inhalation delivery systems. Devices suitable for administration by inhalation of carrier formulations include, but are not limited to, atomizers, vaporizers, nebulizers, and dry powder inhalation delivery devices.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

In some embodiments, the synthetic, biodegradable particles of the present invention provide ease of manufacturing, broad availability of therapeutic agents, and increased treatment sites. Experiments conducted during development of embodiments of the present invention demonstrated the conjugation of peptides (e.g., $PLP_{139-151}$ peptide) to these particles. Such peptide-coupled particles have shown that they are effective for the prevention of disease development and the induction of immunological tolerance (e.g., in the SJL/J $PLP_{139-151}$/CFA-induced R-EAE murine model of multiple sclerosis). Peptide coupled carriers of the present invention provide numerous advantages over other tolerance induction structures. In some embodiments, the particles are biodegradable, and therefore will not persist for long times in the body. The time for complete degradation can be controlled. In some embodiments, particles are functionalized to facilitate internalization without cell activation (e.g., phosphatidylserine loaded into PLG microspheres). In some embodiments, particles incorporate targeting ligands for a specific cell population. In some embodiments, anti-inflammatory cytokines such as IL-10 and TGF-β, are included on or within particles to limit activation of the cell type that is internalizing the particles and to facilitate the induction of tolerance via energy and/or deletion and the activation of regulatory T cells. The composition of the particles has been found to affect the length of time the particles persist in the body and tolerance requires rapid particle uptake and clearance/degradation. Since ratios of over 50:50 lactide:glycolide slow the degradation rate, the particles of the invention have a lactide:glycolide ratio of about 50:50 or below. In one embodiment the particles of the invention have about a 50:50 D,L-lactide:glycolide ratio.

Solid dosage forms for oral administration include capsules, tablets, pills, powders, and granules. In such solid dosage forms, the modified particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The modified particles can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the modified particles only, or preferentially, in a certain part of the intestinal tract, optionally, in a delayed manner. Examples of embedding compositions which can be used include polymeric substances and waxes.

The present invention encompasses pharmaceutically acceptable topical formulations of the inventive modified particles. The term "pharmaceutically acceptable topical formulation", as used herein, means any formulation which is pharmaceutically acceptable for intradermal administration of modified microparticles of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the modified particles. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allantoin, dimethicone, glycerin, petrolatum, and zinc oxide.

In certain embodiments, the pharmaceutically acceptable topical formulations of the invention comprise at least the modified particles of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

The modified particles can be administered by aerosol. This is accomplished by preparing an aqueous aerosol, liposomal preparation or solid particles containing the modified particles. A nonaqueous (e.g., fluorocarbon propellant) suspension could be used.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, PLURONIC®, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It will also be appreciated that the modified particles and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects).

In certain embodiments, the pharmaceutical compositions containing the modified particles of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

The invention provides methods of regulating an immune response in an individual, preferably a mammal, more preferably a human, comprising administering to the individual the modified particles described herein. Methods of immunoregulation provided by the invention include those that suppress and/or inhibit an innate immune response or an adaptive immune response, including, but not limited to, an immune response stimulated by immunostimulatory polypeptides or viral or bacterial components.

The modified particles are administered in an amount sufficient to regulate an immune response. As described herein, regulation of an immune response may be humoral and/or cellular, and is measured using standard techniques in the art and as described herein.

In some embodiments, compositions described herein are administered along with (e.g., concurrent with, prior to, or following) an implant (e.g., device) and/or transplant (e.g., tissue, cells, organ) to mediate, negate, regulate and/or reduce the immune response associated therewith.

Indications

In certain embodiments, the individual suffers from a disorder associated with unwanted immune activation, such as allergic disease or condition, allergy and asthma. An individual having an allergic disease or asthma is an individual with a recognizable symptom of an existing allergic disease or asthma. Tolerance can be induced in such an individual, for example, by particles complexed with the specific foods (e.g. peanut proteins, etc.), injected substances (e.g. bee venom proteins, etc.), or inhaled substances (e.g. ragweed pollen proteins, pet dander proteins, etc.) which elicit the allergic reaction.

In certain embodiments, the individual suffers from a disorder associated with unwanted immune activation, such as autoimmune disease and inflammatory disease. An individual having an autoimmune disease or inflammatory disease is an individual with a recognizable symptom of an existing autoimmune disease or inflammatory disease. Tolerance can be induced in such an individual, for example, by particles complexed with the relevant autoantigens driving the particular autoimmune disease.

In certain embodiments, the individual suffers from a disorder associated with enzyme replacement therapy. Tolerance can be induced in such an individual, for example, by particles covalently coupled with the enzymes which patients with genetic deficiencies fail to produce, to prevent them from making neutralizing antibody responses to recombinantly-produced enzymes administered to treat their particular deficiency, e.g. tolerance to human Factor VIII in patients with hemophilia due to a genetic deficiency in the ability to make Factor VIII. Another example may include enzyme replacement in for conditions such as mucopolysaccharide storage disorder, gangliosidosis, alkaline hypophosphatasia, cholesterol ester storage disease, hyperuricemia, growth hormone deficiency, renal anemia or with lysomal storage disorders including Fabry's disease, Gaucher's disease, Hurler's disease, Hunter's syndrome, Maroteaux-Lamy disease, Niemann-Pick disease, Tay-Sachs disease, and Pompe disease.

In certain embodiments, the individual suffers from a robust, or otherwise adverse, immune response towards an agent administered for the treatment of a disease that actually or potentially compromises patient health or treatment. Additionally, novel compounds provided by this invention may be provided to individuals who do not show an immune response to an agent but may potentially do so in the future. In certain embodiments, the individual is receiving enzyme replacement therapy. In certain embodiments, therapeutic agents include, but are not limited to, peptides or protein-based agents, DNA vaccines, siRNA, splice-site switching oligomers, and RNA-based nanoparticles. In some embodiments, the therapeutic agents include, but are not limited to, Advate, antihemophilic factor, Kogenate, Eloctate, recombinant factor VIII Fc fusion protein, Refacto, Novo VIIa, recombinant factor VII, eptacog alfa, Helixate, Monanine, Coagulation Factor IX, Wilate, Ceredase, Alglucerase, Cerezyme, Imiglucerase, Elelso, taliglucerase alfa, Fabrazyme, Agalsidase beta, Aldurazyme, —l-iduronidase, Myozyme, Acid-glucosidase, Elaprase, iduronate-2-sulfatase, Naglazyme arylsufatase B, and N-acetylgalactosamin e-4-sulfatase. In some embodiments, the individual is administered therapeutic agents administered to treat diseases including, but not limited to, Hemophilia, Hemophilia A, Hemophilia B, von Willebrand disease, Gaucher's Disease, Fabry's Disease, Hurler's Disease, Pompe's Disease, Hunter's Disease, mucopolysaccharide storage disorder, gangliosidosis, alkaline hypophosphatasia, cholesterol ester storage disease, hyperuricemia, growth hormone deficiency, renal anemia and Maroteaux-Lary Disease.

In certain embodiments, the individual suffers from an orphan autoimmune condition. Such conditions include, but are not limited to, idiopathic thrombocytopenic purpura, membranous nephropathy, bullous pemphigoid, pemphigus vulgaris, and Myasthenia Gravis.

In certain embodiments, the individual suffers from a disorder associated with disease therapy. In the case of recombinant antibodies, tolerance is induced for example, to a humanized antibody being employed in a therapeutic context to prevent a patient from making neutralizing antibodies against the antibody therapeutic, e.g. tolerance to a humanized immune subset depleting antibody or anti-cytokine antibody being used as a treatment for autoimmune disease.

Autoimmune diseases can be divided in two broad categories: organ-specific and systemic. Autoimmune diseases include, without limitation, rheumatoid arthritis (RA), systemic lupus erythematosus (SLE), type I diabetes mellitus, type II diabetes mellitus, multiple sclerosis (MS), immune-mediated infertility such as premature ovarian failure, scleroderma, Sjogren's disease, vitiligo, alopecia (baldness), polyglandular failure, Grave's disease, hypothyroidism, polymyositis, pemphigus vulgaris, pemphigus foliaceus, inflammatory bowel disease including Crohn's disease and ulcerative colitis, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, Celiac disease, hypoparathyroidism neuomyelitis optica, membraneous nephropathy, bullous pemphigoid, pemphigus vulgaris, myasthenia gravis.

Autoimmune diseases may also include, without limitation, Hashimoto's thyroiditis, Type I and Type II autoimmune polyglandular syndromes, paraneoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barre syndrome, chronic inflammatory demyelinating polyradiculoneuropathy, multifocal motor neuropathy with conduction block, chronic neuropathy with monoclonal gammopathy, opsonoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritides, polymyositis/dermatomyositis, mixed connective tissue disease, Bechet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiutis obliterans, sarcoidosis, glomerulonephritis, and cryopathies. These conditions are well known in the medical arts and are described, for example, in Harrison's Principles of Internal Medicine, 14th ed., Fauci A S et al., eds., New York: McGraw-Hill, 1998.

Animal models for the study of autoimmune disease are known in the art. For example, animal models which appear most similar to human autoimmune disease include animal strains which spontaneously develop a high incidence of the particular disease. Examples of such models include, but are not limited to, the nonobese diabetic (NOD) mouse, which develops a disease similar to type 1 diabetes, and lupus-like disease prone animals, such as New Zealand hybrid, MRL-Fas$^1_{p'}$ and BXSB mice. Animal models in which an autoimmune disease has been induced include, but are not limited to, experimental autoimmune encephalomyelitis (EAE), which is a model for multiple sclerosis, collagen-induced arthritis (CIA), which is a model for rheumatoid arthritis, Desmoglein 3 transgenic T cell mouse, which can be used as an experimental model of Pemphigus Vulgaris and experimental autoimmune uveitis (EAU), which is a model for uveitis. Animal models for autoimmune disease have also been created by genetic manipulation and include, for example, IL-2/IL-10 knockout mice for inflammatory bowel disease, Fas or Fas ligand knockout for SLE, and IL-I receptor antagonist knockout for rheumatoid arthritis.

In certain embodiments, the individual suffers from a bacterial or viral infection. An individual having a bacterial or viral infection is an individual with a recognizable symptom of an existing bacterial or viral infection.

A non-limiting list of viral infections treatable with the modified particles of the current invention includes herpes virus infections, hepatitis virus infections, west nile virus infections, flavivirus infections, influenza virus infections, rhinovirus infections, papillomavirus infections, paromyxovirus infections, parainfluenza virus infections, and retrovirus infections. Preferred viruses are those viruses that infect the central nervous system of the subject. Most preferred viruses are those that cause hemorrgic fever, encephalitis or meningitis.

A non-limiting list of bacterial infections treatable with the modified particles of the current invention include *staphlococcus* infections, *streptococcus* infections, *mycobacterial* infections, *bacillus* infections, *Salmonella* infections, *Vibrio* infections, *spirochete* infections, and *Neisseria* infections. Preferred are bacteria that infect the central nervous system of the subject. Most preferred are bacteria that cause encephalitis or meningitis.

In some embodiments, the invention relates to uses of compositions of this invention prior to the onset of disease. In other embodiments, the invention relates to uses of the compositions of this invention to inhibit ongoing disease. In some embodiments, the invention relates to ameliorating disease in a subject. By ameliorating disease in a subject is meant to include treating, preventing or suppressing the disease in the subject.

In some embodiments, the invention relates to preventing the relapse of disease. For example, an unwanted immune response can occur at one region of a peptide (such as an antigenic determinant). Relapse of a disease associated with an unwanted immune response can occur by having an immune response attack at a different region of the peptide. Since the immune modifying particles of the current invention are free from attached peptides or antigenic moieties, the particles will be effective against multiple epitopes. T-cell responses in some immune response disorders, including MS and other ThI/17-mediated autoimmune diseases, can be dynamic and evolve during the course of relapsing-remitting and/or chronic-progressive disease. The dynamic nature of the T-cell repertoire has implications for treatment of certain diseases, since the target may change as the disease progresses. Previously, pre-existing knowledge of the pattern of responses was necessary to predict the progression of disease. The present invention provides compositions that can prevent the effect of dynamic changing disease, a function of "epitope spreading." A known model for relapse is an immune reaction to proteolipid protein (PLP) as a model for multiple sclerosis (MS). Initial immune response can occur by a response to $PLP_{139-151}$. Subsequent disease onset can occur by a relapse immune response to PLP[pi]s-iβi.

Other embodiments of this invention relate to transplantation. This refers to the transfer of a tissue sample or graft from a donor individual to a recipient individual, and is frequently performed on human recipients who need the tissue in order to restore a physiological function provided by the tissue. Tissues that are transplanted include (but are not limited to) whole organs such as kidney, liver, heart, lung; organ components such as skin grafts and the cornea of the eye; and cell suspensions such as bone marrow cells and cultures of cells selected and expanded from bone marrow or circulating blood, and whole blood transfusions.

A serious potential complication of any transplantation ensues from antigenic differences between the host recipient and the engrafted tissue. Depending on the nature and degree of the difference, there may be a risk of an immunological assault of the graft by the host, or of the host by the graft, or both, may occur. The extent of the risk is determined by following the response pattern in a population of similarly treated subjects with a similar phenotype, and correlating the various possible contributing factors according to well accepted clinical procedures. The immunological assault may be the result of a preexisting immunological response (such as preformed antibody), or one that is initiated about the time of transplantation (such as the generation of Th cells). Antibody, Th cells, or Tc cells may be involved in any combination with each other and with various effector molecules and cells. However, the antigens which are involved in the immune response are generally not known, therefore posing difficulties in designing antigen-specific therapies or inducing antigen-specific tolerance.

Certain embodiments of the invention relate to decreasing the risk of host versus graft disease, leading to rejection of the tissue graft by the recipient. The treatment may be performed to prevent or reduce the effect of a hyperacute, acute, or chronic rejection response. Treatment is preferentially initiated sufficiently far in advance of the transplant so that tolerance will be in place when the graft is installed; but where this is not possible, treatment can be initiated simultaneously with or following the transplant. Regardless of the time of initiation, treatment will generally continue at regular intervals for at least the first month following transplant. Follow-up doses may not be required if a sufficient accommodation of the graft occurs, but can be resumed if there is any evidence of rejection or inflammation of the graft. Of course, the tolerization procedures of this invention may be combined with other forms of immunosuppression to achieve an even lower level of risk.

Certain embodiments of the invention relate to decreasing or otherwise ameliorating the inflammatory response induced as a response to surgery. In one embodiment of the invention, the immune-modifying particles are administered before surgery. In a further embodiment of the invention, the immune-modifying particles are administered concurrently with or during surgery. In yet a further embodiment of the invention, the immune-modifying particles are administered after surgery.

The particles of the invention may also be used to treat abscesses or empyemas to decrease the inflammatory response produced in the subject after exposure to infectious agents such as bacteria or parasites. In one embodiment of the invention, the immune-modifying particles are administered in conjunction with anti-bacterial and/or anti-parasitic treatments known in the art.

The particles of the invention may also be used to decrease or otherwise ameliorate the inflammatory response induced as a response to physical trauma or injury including, but not limited to, a sports injury, a wound, a spinal cord injury, a brain injury, and/or a soft tissue injury. In one embodiment of the invention, the immune-modifying particles are administered after the subject experiences trauma or injury.

The particles of the invention may also be used to decrease the inflammatory response associated with the development and/or growth of cancer cells. Cancers that can be treated include, but are not limited to, central nervous system cancer, basal cell carcinoma, cancerous brain tumors, Burkitt's lymphoma, lymphoma, cervical cancer, ovarian cancer, testicular cancer, liver cancer, non-small cell and small cell lung cancers, melanoma, bladder cancer, breast cancer, colon and rectal cancers, endometrial cancer, kidney (renal cell) cancer, leukemia, Non-Hodgkin lymphoma, pancreatic cancer, prostate cancer, melanoma, and thyroid cancer. In one embodiment, the subcutaneous injection of the particles of the invention prevents the accumulation of inhibitory neutrophils, thereby decreasing inflammation in the cancer patient.

The particles of the invention are also useful for the regeneration of damaged tissue. In one embodiment, administration of the particles to a patient increases the regeneration of damaged epithelial cells in the digestive tract. In a further embodiment, the patient suffers from colitis, Crohn's disease, or inflammatory bowel disease. In another embodiment, administration of the particles of the invention to a patient increases remyelination of neurons. In a further embodiment, the patient suffers from multiple sclerosis.

Scaffolds, Matrices, and Delivery Systems

In some embodiments, compositions of the present invention (e.g., PLG carrier polymer covalently coupled to antigenic molecule) find use with one or more scaffolds, matrices, and/or delivery systems (See, e.g., U.S. Pat. App. 2009/0238879; U.S. Pat. Nos. 7,846,466; 7,427,602; 7,029, 697; 6,890,556; 6,797,738; 6,281,256; herein incorporated by reference in their entireties). In some embodiments, particles (e.g., antigen-coupled PLG particles) are associated with, adsorbed on, embedded within, conjugated to, etc. a scaffold, matrix, and/or delivery system (e.g., for delivery of chemical/biological material, cells, tissue, and/or an organ to a subject). In some embodiments, a scaffold, matrix, and/or delivery system (e.g., for delivery of chemical/biological material, cells, tissue, and/or an organ to a subject) comprises and/or is made from materials described herein (e.g., PLG conjugated to one or more antigenic peptides).

In some embodiments, microporous scaffolds (e.g., for transplanting biological material (e.g., cells, tissue, etc.) into a subject) are provided. In some embodiments, microporous scaffolds are provided having thereon agents (e.g., extracellular matrix proteins, exendin-4) and biological material (e.g., pancreatic islet cells). In some embodiments, the scaffolds are used in the treatment of diseases (e.g., type 1 diabetes), and related methods (e.g., diagnostic methods, research methods, drug screening). In some embodiments, scaffolds are provided with the antigen-conjugated carriers described herein on and/or within the scaffold. In some embodiments, scaffolds are produced from antigen conjugated materials (e.g., antigen conjugated PLG).

In some embodiments, a scaffold and/or delivery system comprises one or more layers and/or has one or more chemical and/or biological entities/agents (e.g., proteins, peptide-conjugated particles, small molecules, cells, tissue, etc.), see, e.g., U.S. Pat. App. 2009/0238879; herein incorporated by reference in its entirety. In some embodiments, antigen-coupled particles are co-administered with a scaffold delivery system to elicit induction of immunological tolerance to the scaffold and the associated materials. In some embodiments, microporous scaffold is administered to a subject with particles described herein on or within the scaffold. In some embodiments, antigen-coupled particles coupled to a scaffold delivery system. In some embodiments, a scaffold delivery system comprises antigen-coupled particles.

Various modification, recombination, and variation of the described features and embodiments will be apparent to those skilled in the art without departing from the scope and spirit of the invention. Although specific embodiments have been described, it should be understood that the invention as claimed should not be unduly limited to such specific embodiments. Indeed, various modifications of the described modes and embodiments that are obvious to those skilled in the relevant fields are intended to be within the scope of the following claims. For example, U.S. Pat. Applications 2012/0076831, 2002/0045672, 2005/0090008, 2006/0002978, and 2009/0238879 (each of which is herein incorporated by reference in their entirety) and U.S. Pat. Nos. 7,846,466; 7,427,602; 7,029,697; 6,890,556; 6,797, 738; and 6,281,256 (each of which is herein incorporated by reference in their entirety) provide details, modifications, and variations that find use in various embodiments described herein.

All publications and patents mentioned in the present application and/or listed below are herein incorporated by reference in their entireties.

EXAMPLES

The following examples are provided to further illustrate the advantages and features of the invention, but are not intended to limit the scope of this disclosure.

Materials and Methods

Microscope and Image Acquisition

Images were acquired on an Olympus BX-51 microscope (Olympus, Japan), using a DP-70 camera and DP manager 2.2.1 software (Olympus).

Isolation of Leukocytes from the Brain and Liver

As previously described (Getts et al, J Exp Med. 29: 2319, 2007) leukocytes were obtained from the brains of PBS-perfused mice by digesting brains for 60 minutes at 37° C. in PBS with deoxy-ribonuclease (0.005 g/ml; Sigma Aldrich) and collagenase IV (0.05 g/ml; Sigma Aldrich). Digestion was stopped with 10% FCS, and the homogenate was passed through a 70 μm nylon cell strainer (Becton Dickinson, N.J., USA). The pellet, obtained after 10 minutes centrifugation at 340×g, was resuspended in 30% Percoll (Amersham, Norway) and layered over 80% Percoll. Leukocytes were collected from the 30%/80% interface after centrifugation at 1140×g for 25 minutes at room temperature. The same protocol is also used to derive leukocytes from the liver, with the tissue weighed before processing.

Isolation of Leukocytes from the Spleen, Blood and Bone Marrow

For flow cytometric analysis, the right femur was dissected out and bone marrow cells flushed out using PBS loaded syringes. For bone marrow precursor isolation, femurs and tibias from at least 4 mice were utilized. The cellular suspension achieved after flushing was filtered through a 70 μm cell strainer and centrifuged for 5 mins at 340 g. Red blood cells in the resulting pellet were lysed in $NH_4Cl$-based red cell lysis buffer (BD Pharm Lyse™; BD Pharmingen), before centrifugation for 5 mins at 340×g. In the case of peripheral blood, blood was collected via cardiac puncture and immediately transferred into citrate buffer (mMol, Sigma Alrich). The resulting suspension was layered over 70% Percoll and centrifuged at 1140×g for 20 minutes at room temperature with the brake off. The interface was collected and the cells washed once in PBS, centrifuged at 340×g. For the isolation of splenic leukocytes, spleens were passed through a 7070 μm cell strainer and centrifuged for 5 mins at 340 g. Red blood cells in the resulting pellet were lysed in $NH_4Cl$-based red cell lysis buffer (BD Pharm Lyse™; BD Pharmingen), before centrifugation for 5 mins at 340×g.

Flow Cytometry

Cells collected (as described above) from the brain, liver, blood, and bone marrow were washed in PBS, and blocked with anti-CD16/CD32 antibody (Biolegend). Viable cells were counted using trypan blue exclusion, which routinely showed >95% cell viability.

Cell surface molecule expression was measured and cell sorts carried out on a FACS ARIA (Becton Dickinson), equipped with an Argon ion and HeNe laser. Viable populations were gated by forward and side scatter and identified fluorescent populations determined by forward-gating thereafter. Sorting was carried out using specific fluorescent and scatter parameters identifying the population of interest. Sorting stringencies was set to purity to achieve >98% purity for bone marrow populations.

Acquired FACS data files were analysed using the flow cytometry program, Flow Jo (FlowJo, Ashland, Oreg., USA). Quantification of cell populations of interest were calculated based on flow cytometry percentages at analysis and absolute cell counts from each organ.

Induction and Evaluation of Experimental Autoimmune Encephalitis (EAE)

Mice were injected sub-cutaneously with emulsion containing 0.1 mg MOG Peptide (MEVGWYRSPFSRVVH-LYRNGK (SEQ ID NO:1); Auspep, Parkville, Victoria, Australia; >95% HPLC purified) and Complete Freund's adjuvant containing 2 mg/mL *Mycobacterium tuberculosis* (Sigma Aldrich). Two days later, mice were administered 500 μl Pertussis toxin (Sigma Aldrich) i.p. Mice were monitored for disease progression, and graded on the following scale: 1, limp tail and/or weakness of 1 hind limb; 2, weakness in more than one limb, gait disturbance; 3, paralysis in 1 limb; 4, paralysis in more than one limb, incontinence; 5, moribund.

Statistics

Graphs were made and computerized statistical analysis was performed in GraphPad Prism, and InStat, respectively (both programs from GraphPad software, San Diego, Calif., USA). Depending on the data, an unpaired, two-tailed Student t-test, or one way ANOVA with a Tukey-Kramer post-test was performed, with $P<0.05$ considered to be significant.

For correlation analysis between parameters such as weight loss, infiltration, and virus titre, a non-linear regression (curve fit) was used, with a second order polynomial ($Y=A+B*X+C*X^2$).

Example 1

Synthesis and Characterization of PLG Peptide Conjugates and Nanoparticle Formation Poly(lactide-co-glycolic acid) (PLG) was covalently linked to either Cy5.5 fluorescent dye or antigen with the coupling reagent 1-Ethyl-3-(3-dimethylaminopropyl)carbodiimide (EDC)/N-hydroxysuccinimide (NHS). The antigen was either proteolipid protein ($PLP_{139-151}$) or ovalbumin ($OVA_{323-339}$) (FIG. 1).

Particles with various sizes were prepared by the double emulsion and nanoprecipitation methods. The size and zeta potential of the nanoparticle formulations were determined and are provided above in Table 1.

The coupling efficiency of antigen to PLG was analysed by $^1$H-NMR. FIG. 2 shows the $^1$H-NMR spectrum of (i) PLG, (ii) $OVA_{323-339}$, and (iii) $PLG$-$OVA_{323-339}$ measured in DMSO-d6 (calibrated at 2.5 ppm). The coupling efficiency of $OVA_{323-339}$ to PLG was calculated by comparing the integration values of the overlapping methyl proton peaks of leucine and isoleucine present at 1.4 ppm in $OVA_{323-339}$ (d, d') to the methylene proton peak present at 5.3 ppm in PLG (b). A schematic representation of the polymer-conjugate nanoparticles is provided in FIG. 2C.

By changing the chemistry, the coupling efficiency of PLP to PLG can be increased to about 20%.

Loading (μg antigen (Ag)/mg PLG) was precisely controlled by combining PLG-Ag conjugates with unconjugated PLG at predetermined mixing ratios (see Table 1 above).

Example 2

Size and Time-Dependent Cellular Interactions of PLG Nanoparticles

Figure 3:
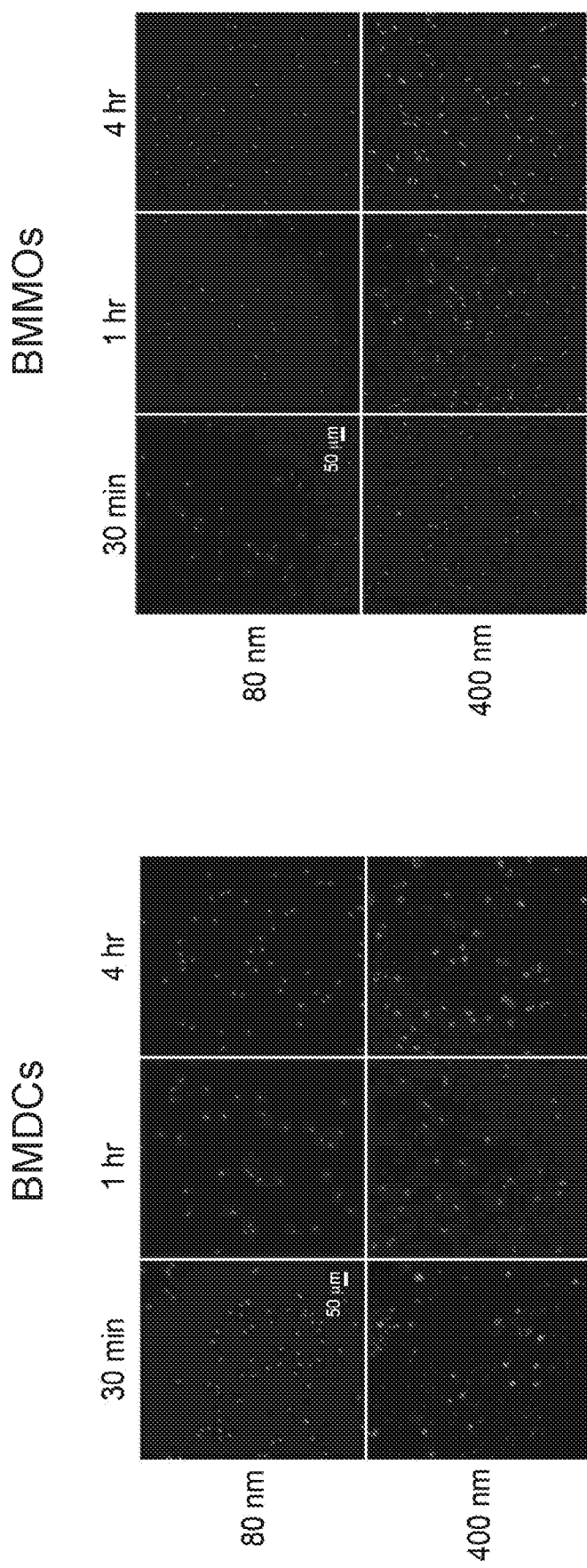
FIG. 3 shows size and time-dependent cellular interactions of PLG nanoparticles. 80 nm and 400 nm PLG nanoparticles were fluorescently labeled with 1% (by wt.) PLG-Cy5.5 conjugate and incubated with bone marrow-derived dendritic cells (BMDCs) or bone marrow-derived macrophages (BMMOs) up to 4 hr at 37° C. Blue: DAPI; Red: PLG-Cy5.5 nanoparticles).

Eighty nm and 400 nm PLG nanoparticles were fluorescently labeled with 1% (by wt.) PLG-Cy5.5 conjugate and incubated with bone marrow-derived dendritic cells (BMDCs) or bone marrow-derived macrophages (BMMOs) up to 4 hr at 37° C. (FIG. 3). The blue fluorescence indicates DAPI staining of nuclei and the red fluorescence indicates PLG-Cy5.5 nanoparticles.

Example 3

Figure 4:
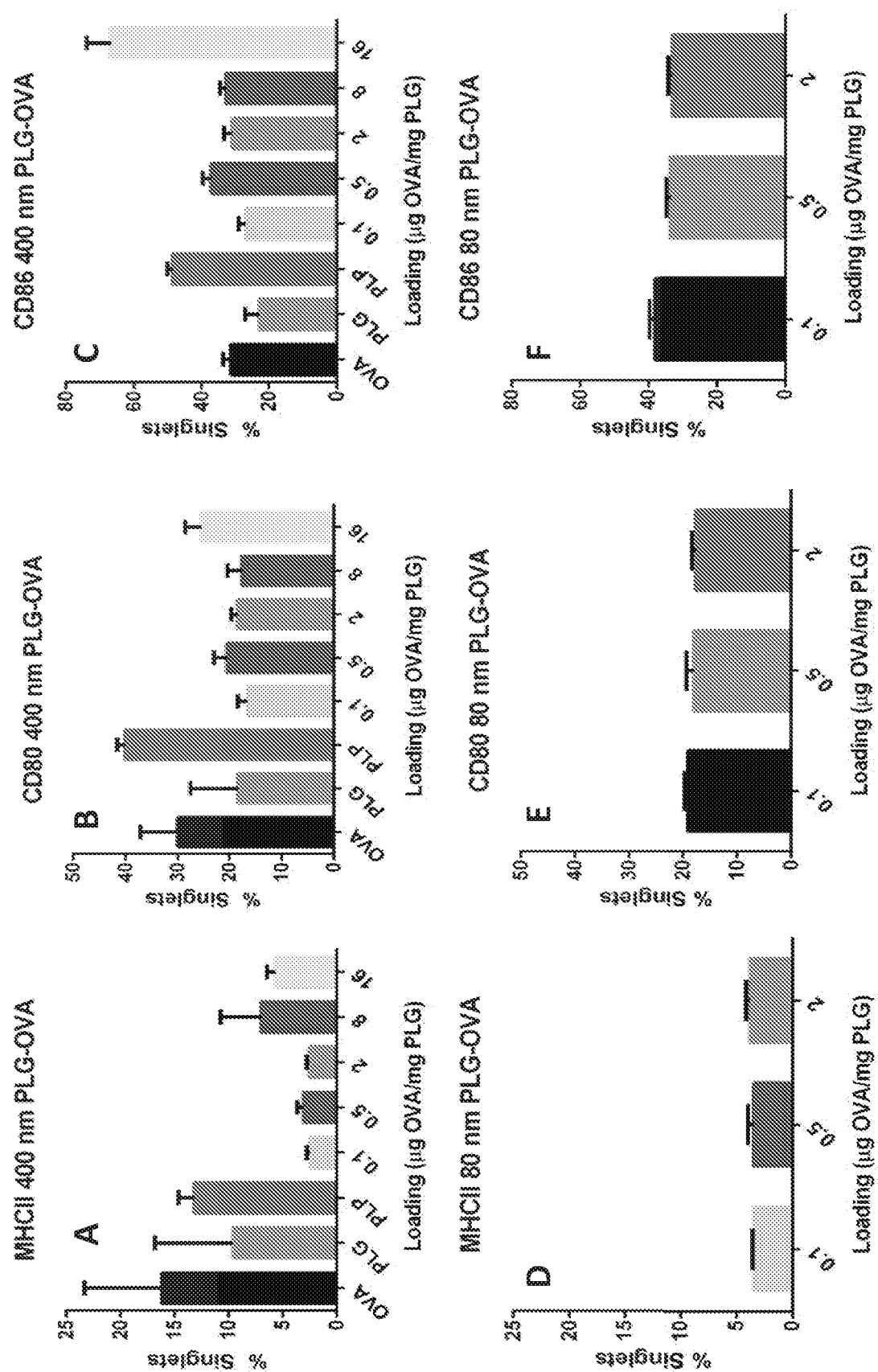
FIG. 4A-4F shows BMDC surface marker characterization after treatment with PLG-OVA$_{323\text{-}339}$ particles having various antigen loadings.

BMDC Surface Marker Characterization after Treatment with PLG-OVA Particles Having Various Antigen Loadings BMDCs were treated for 3 hr with 300 μg/mL of 400 nm and 80 nm PLG-OVA nanoparticle formulations with various antigen-loadings. Non-internalized PLG-OVA nanoparticles were subsequently washed from the cell surface. The cell surface markers MHCII, CD80 and CD86 were assayed using flow cytometry after 4 days of incubation. FIG. 4A and FIG. 4D show MHCII marker expression following treatment with 400 nm and 80 nm particles, respectively. FIG. 4B and FIG. 4E show CD80 marker expression following treatment with 400 nm and 80 nm particles, respectively. FIG. 4C and FIG. 4F show CD86 marker expression following treatment with 400 nm and 80 nm particles, respectively. Treatment of cells with PLG-OVA nanoparticles, regardless of antigen content, resulted in significantly downregulated MHCII and CD80 expression.

Example 4

Antigen-Specific Induction of Regulatory T Cells by PLG-OVA Particles Delivered to Antigen Presenting Cells (APCs)

Figure 5:
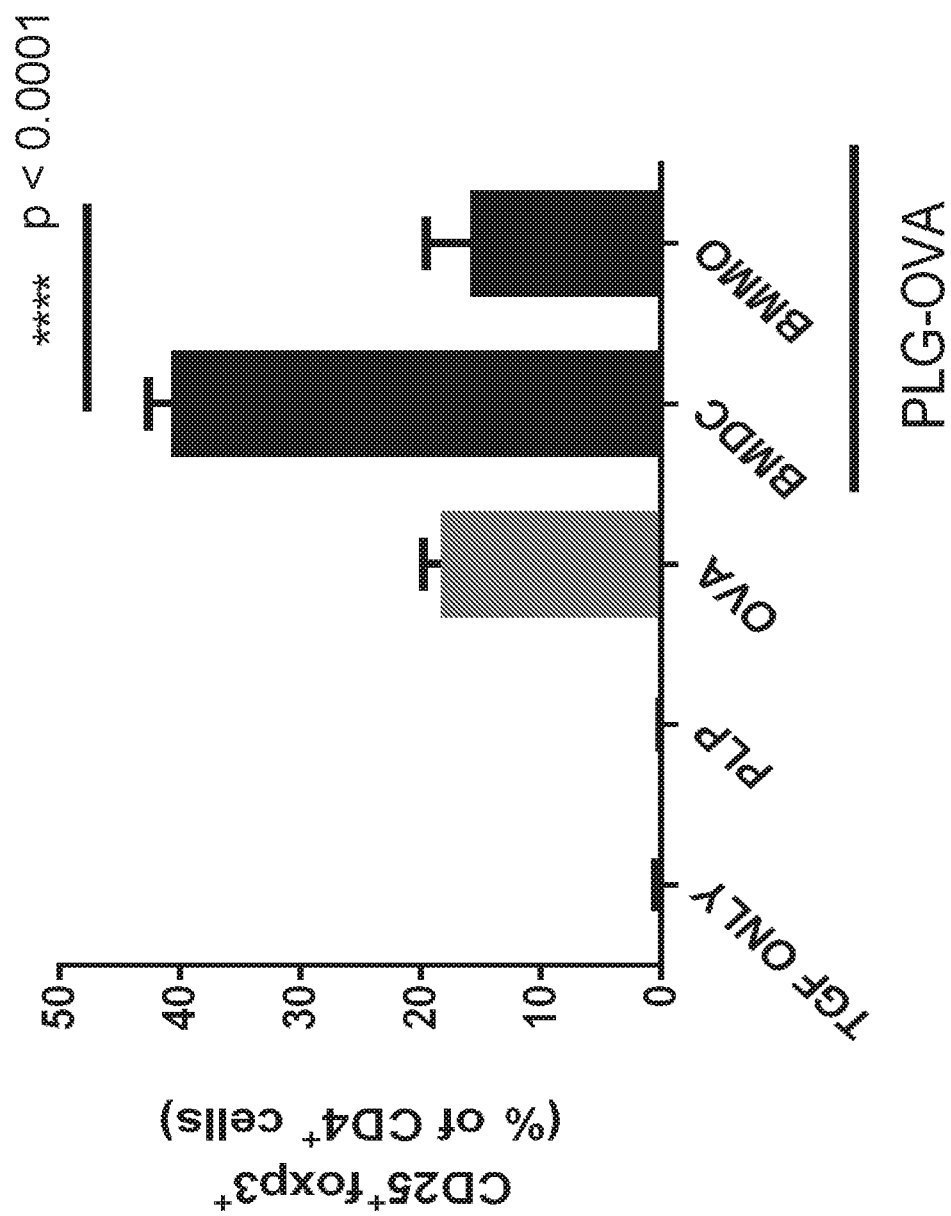
FIG. 5 shows antigen-specific induction of regulatory T cells by PLG-OVA$_{323\text{-}339}$ particles delivered to antigen presenting cells (APCs). The difference in induction in BMDC versus BMMO cells was significant, at $p<0.0001$.

BMDCs or BMMOs were treated for 3 hr with 300 μg/mL of 400 nm PLG-OVA nanoparticle formulations with 8 μg/mg PLG antigen loading. Non-internalized PLG-OVA nanoparticles were subsequently washed from the cell surface prior to addition of OT-II T cells and 2 ng/mL of TGF-β1. The cells were co-cultured for 4 days prior to using flow cytometry to measure CD25 activation and foxp3 expression of T cells as indication of induction of regulatory T cells. The difference in induction in BMDC versus BMMO was significant, at $p<0.0001$ (FIG. 5).

Example 5

Figure 6:
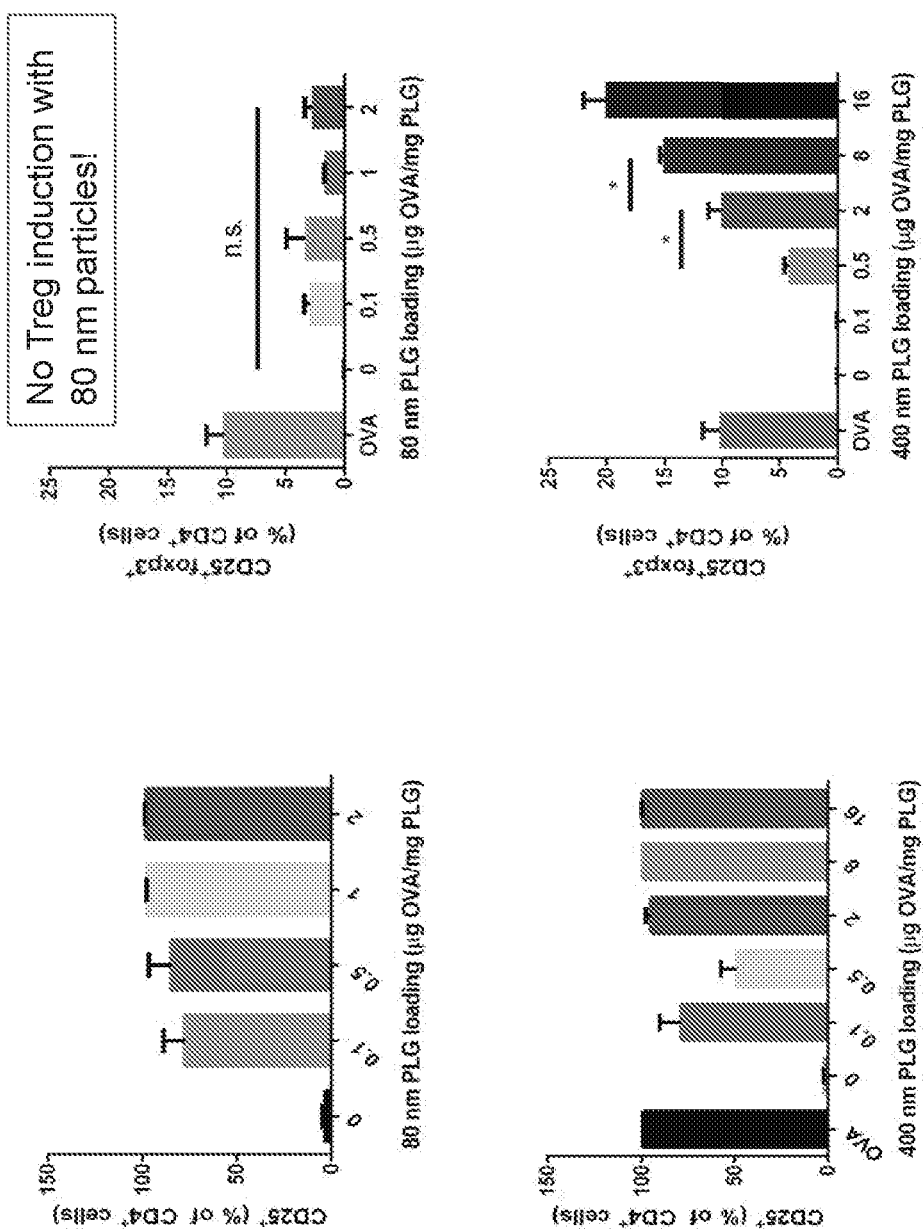
FIG. 6 shows size- and antigen-loading-dependent CD25 activation and induction of regulatory T cells by PLG-OVA$_{323\text{-}339}$ particles. * indicates significance at $p<0.05$.

Size- and Antigen-Loading-Dependent CD25 Activation and Induction of Regulatory T Cells by PLG-OVA Particles Bone marrow-derived dendritic cells (BMDCs) were treated for 3 hr with 300 μg/mL of 400 nm and 80 nm PLG-OVA nanoparticle formulation. Non-internalized PLG-OVA nanoparticles were subsequently washed from the cell surface prior to addition of OT-II T cells and 2 ng/mL of TGF-β1. The cells were co-cultured for 4 days prior to using flow cytometry to measure CD25 activation and foxp3 expression of T cells. Although both nanoparticle formulations were able to increase CD25 activation similarly, only 400 nm PLG-OVA nanoparticles could successfully induce regulatory T cells (FIG. 6).

Example 6

CD25 Activation and Induction of Regulatory T Cells as a Function of PLG-OVA Particle Dose Regulatory T cell induction is dependent on nanoparticle dose. Bone marrow-derived dendritic cells (BMDCs) were treated for 3 hr with various concentrations of 400 nm of PLG-OVA nanoparticles (8 μg/mg loading) formulation.

Figure 7:
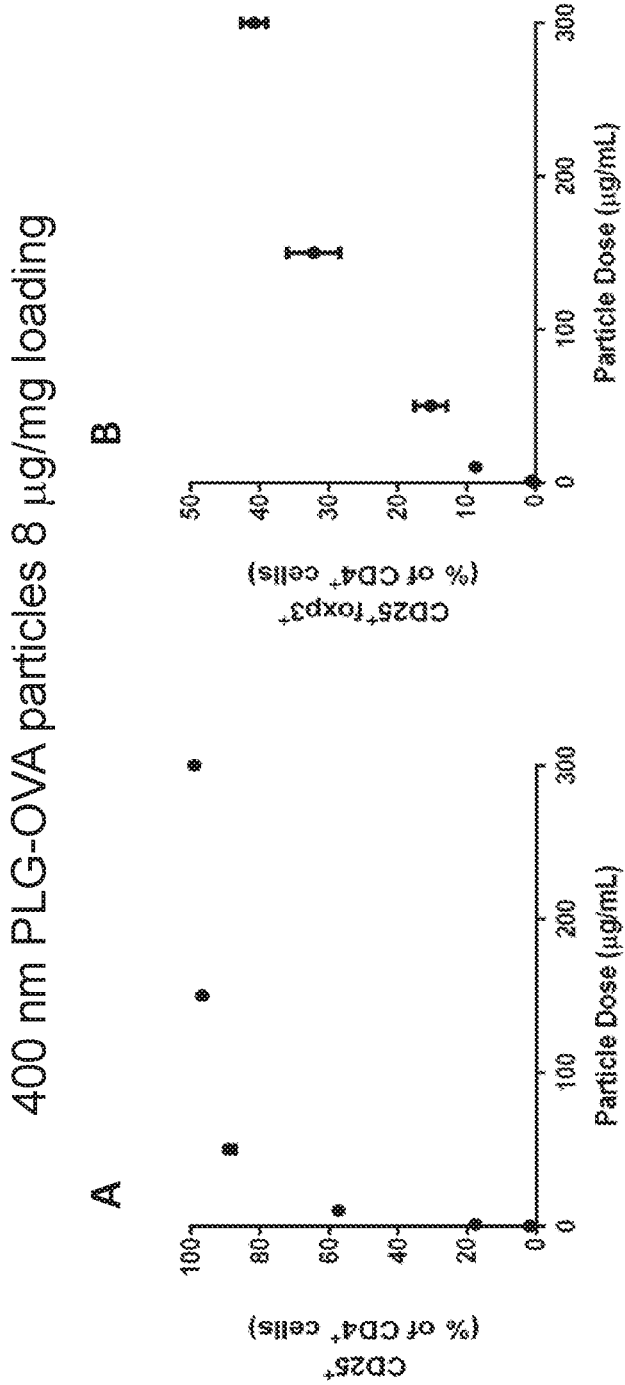
FIG. 7A-7B shows induction of regulatory T cells indicated by (FIG. 7A) CD25 activation and by (FIG. 7B) foxp3 expression as a function of PLG-OVA$_{323\text{-}339}$ particle dose.

Non-internalized PLG-OVA nanoparticles were subsequently washed from the cell surface prior to addition of OT-II T cells and 2 ng/mL of TGF-β1. The cells were co-cultured for 4 days prior to using flow cytometry to measure CD25 activation (FIG. 7A) and foxp3 expression (FIG. 7B) of T cells. Although CD25 activation reached a maximum at 50 µg/mL, foxp3 expression appeared to plateau at 300 mg/mL.

Example 7

Size- and Concentration-Dependent Biodistribution of PLG Particles

Mice were injected either intravenously (IV) or subcutaneously (SC) with 1.25 mg of 400 nm or 80 nm PLG-Cy5.5 nanoparticle formulation. Cells from the liver, kidney, heart, lung, spleen and inguinal lymph nodes were isolated. Data was analyzed by flow cytometry 24 hr after injection. The liver is the primary site of particle accumulation (FIG. 8A).

Figure 8:
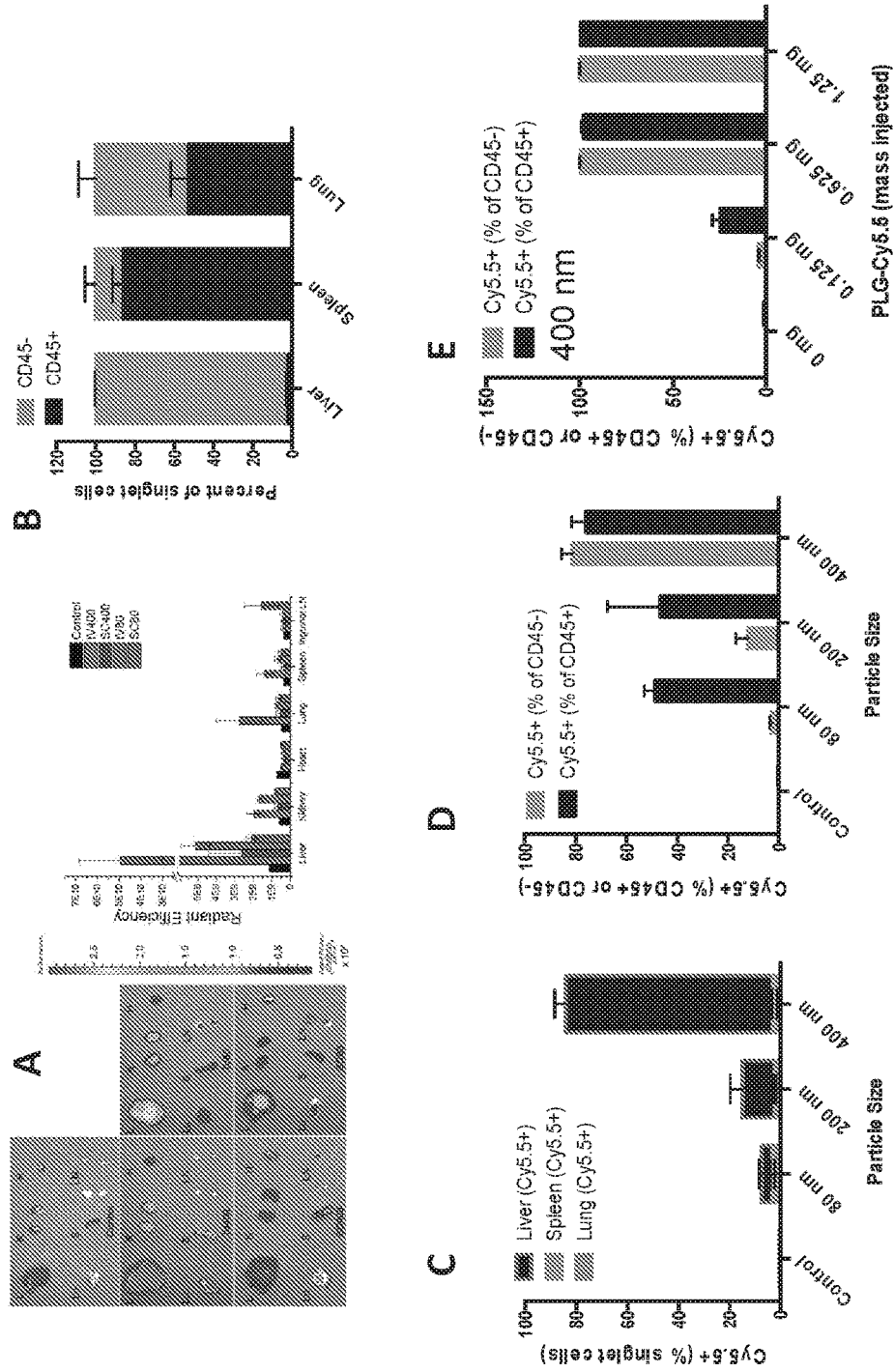
FIG. 8A-8E shows size- and concentration-dependent biodistribution of PLG particles.

The proportion of cells that were CD45+ versus CD45− was determined for liver, spleen and lung (FIG. 8B).

Mice were injected intravenously with 1.25 mg of PLG-Cy5.5 nanoparticle formulations of various particle sizes. Data was analyzed by flow cytometry 24 hr after injection. The proportion of Cy5.5+ cells found in the liver, spleen and lung was determined for a given particle size (FIG. 8C). The vast majority of 400 nm and 200 nm PLG-Cy5.5 nanoparticles were found in the liver. About 50% of CD45+ cells contained 80 nm and 200 nm PLG-Cy5.5 nanoparticles, whereas only about 5% to about 10% of CD45− cells contained 80 nm and 200 nm PLG-Cy5.5 nanoparticles, respectively. By contrast, about 75-80% of both CD45+ and CD45− cells contained 400 nm PLG-Cy5.5 nanoparticles (FIG. 8D). Injection of either 0.625 mg or 1.25 mg of 400 nm PLG-Cy5.5 nanoparticles leads to accumulation of about 100% of the particles in both CD45+ and CD45− cells (FIG. 8E).

Example 8

PLG Particles are Associated with Neutrophils and Monocytes in the Blood

Figure 9:
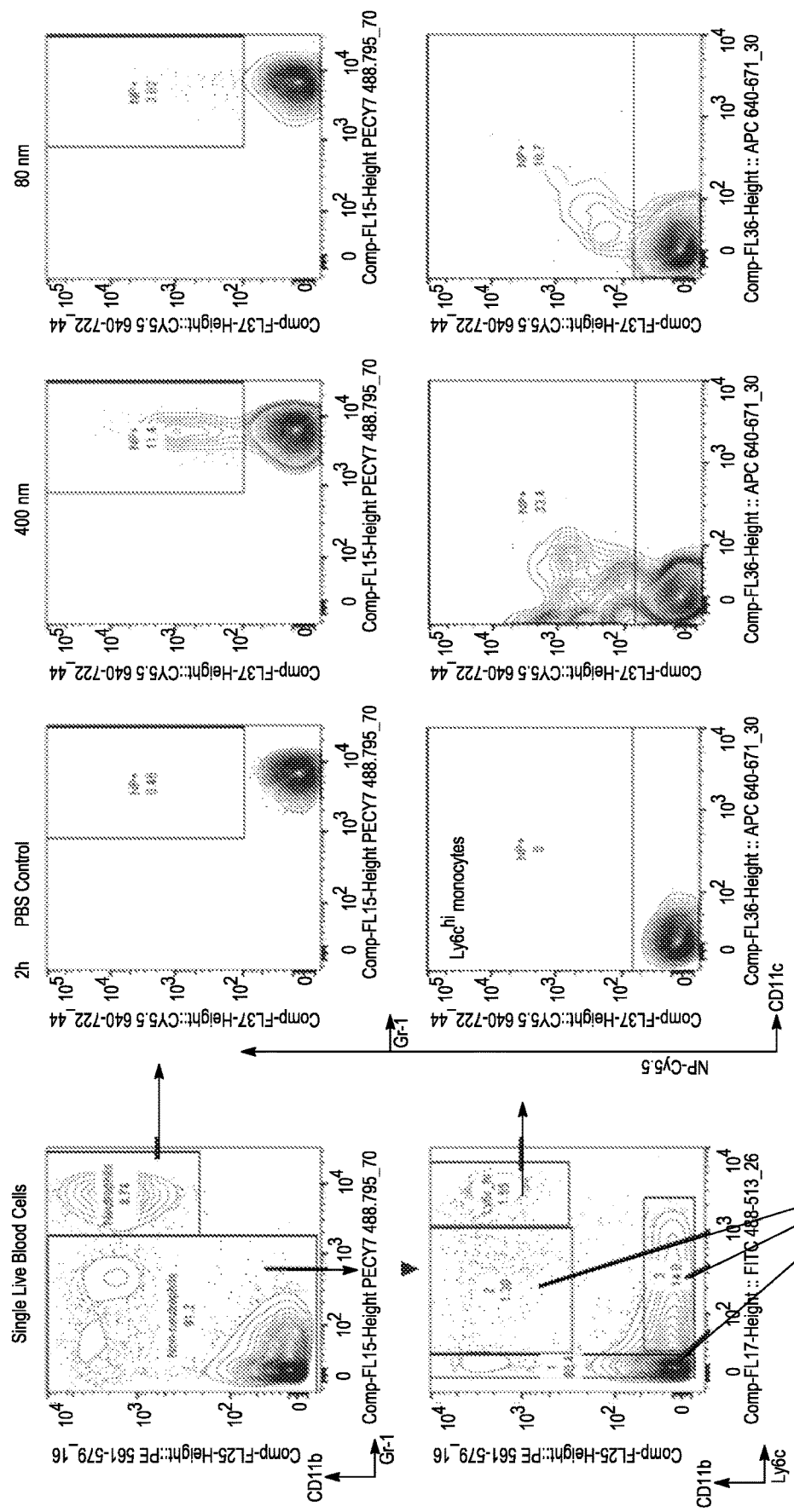
FIG. 9 shows flow cytometric analysis of blood of healthy mice (n=3) injected intravenously with 1.25 mg of 400 nm or 80 nm PLG-Cy5.5 nanoparticle formulation. Blood was collected and analyzed 2 hr after injection. Expression of CD11b, CD11c, Gr-1 and Ly6c markers were used to identify the types of leukocytes. Cy5.5 fluorescence was used to determine which cells had PLG-Cy5.5 nanoparticles.
Figure 9:
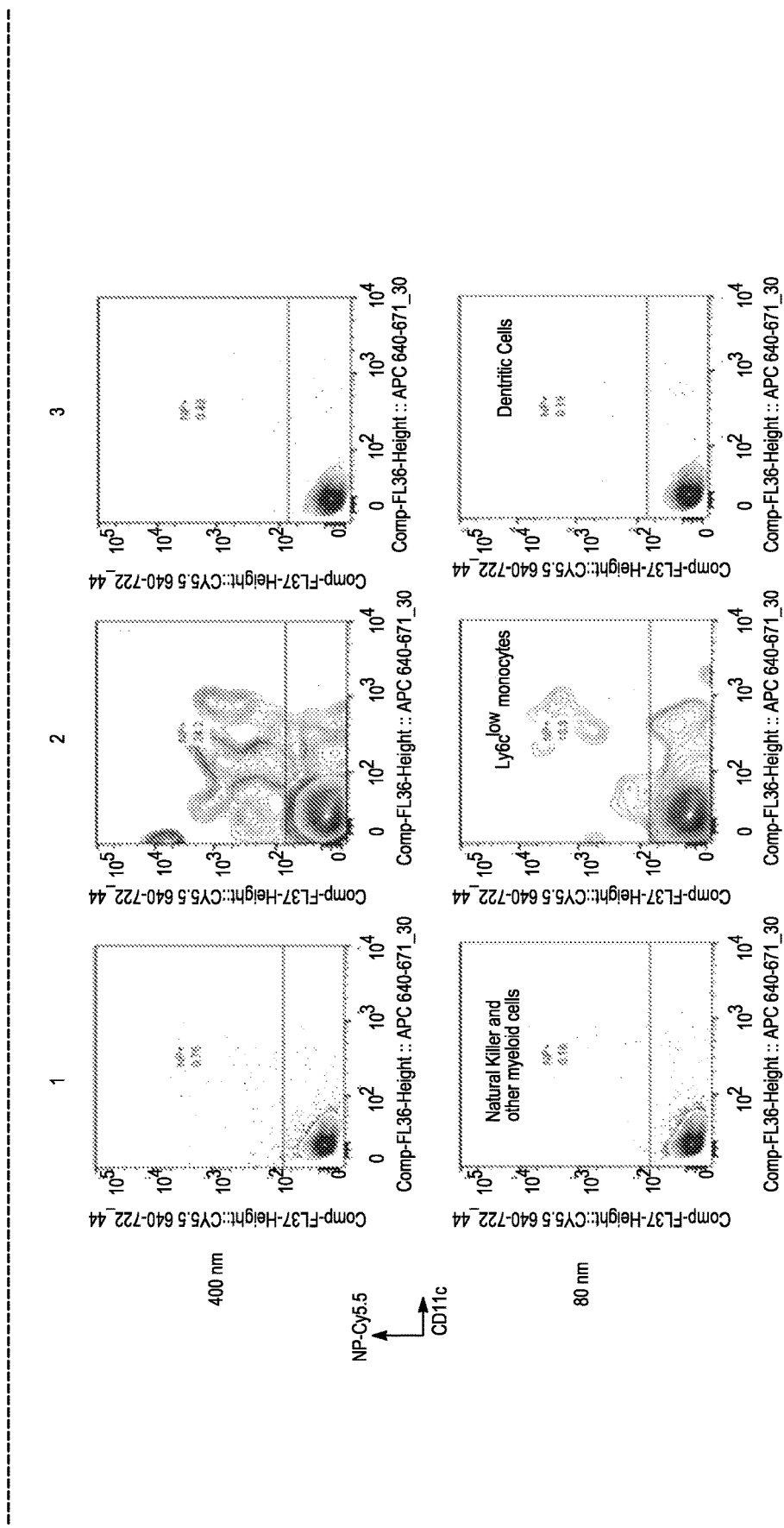

Healthy mice (n=3) were injected intravenously with 1.25 mg of 400 nm or 80 nm PLG-Cy5.5 nanoparticle formulation. Blood was collected and analyzed by flow cytometry 2 hr after injection. Expression of CD11b, CD11c, Gr-1 and Ly6c markers were used to identify the types of leukocytes. Cy5.5 fluorescence was used to determine which cells had 80 nm and 400 nm PLG-Cy5.5 nanoparticles. PLG-Cy5.5 particles are associated with neutrophils and monocytes in the blood (FIG. 9).

Example 9

PLG Particles Induce Regulatory T Cells Ex Vivo and Induce Tolerance in Experimental Autoimmune Encephalitis (EAE)

BMDCs, splenic dendritic cells or liver dendritic cells were treated for 3 hr with 300 µg/mL of either OVA alone or 400 nm PLG-OVA nanoparticle formulations (8 µg/mg PLG antigen loading). Non-internalized PLG-OVA nanoparticles were subsequently washed from the cell surface prior to addition of OT-II T cells and 2 ng/mL of TGF-β1. The cells were co-cultured for 4 days prior to using flow cytometry to measure CD25 activation and foxp3 expression of T cells as indication of induction of regulatory T cells.

Figure 10:
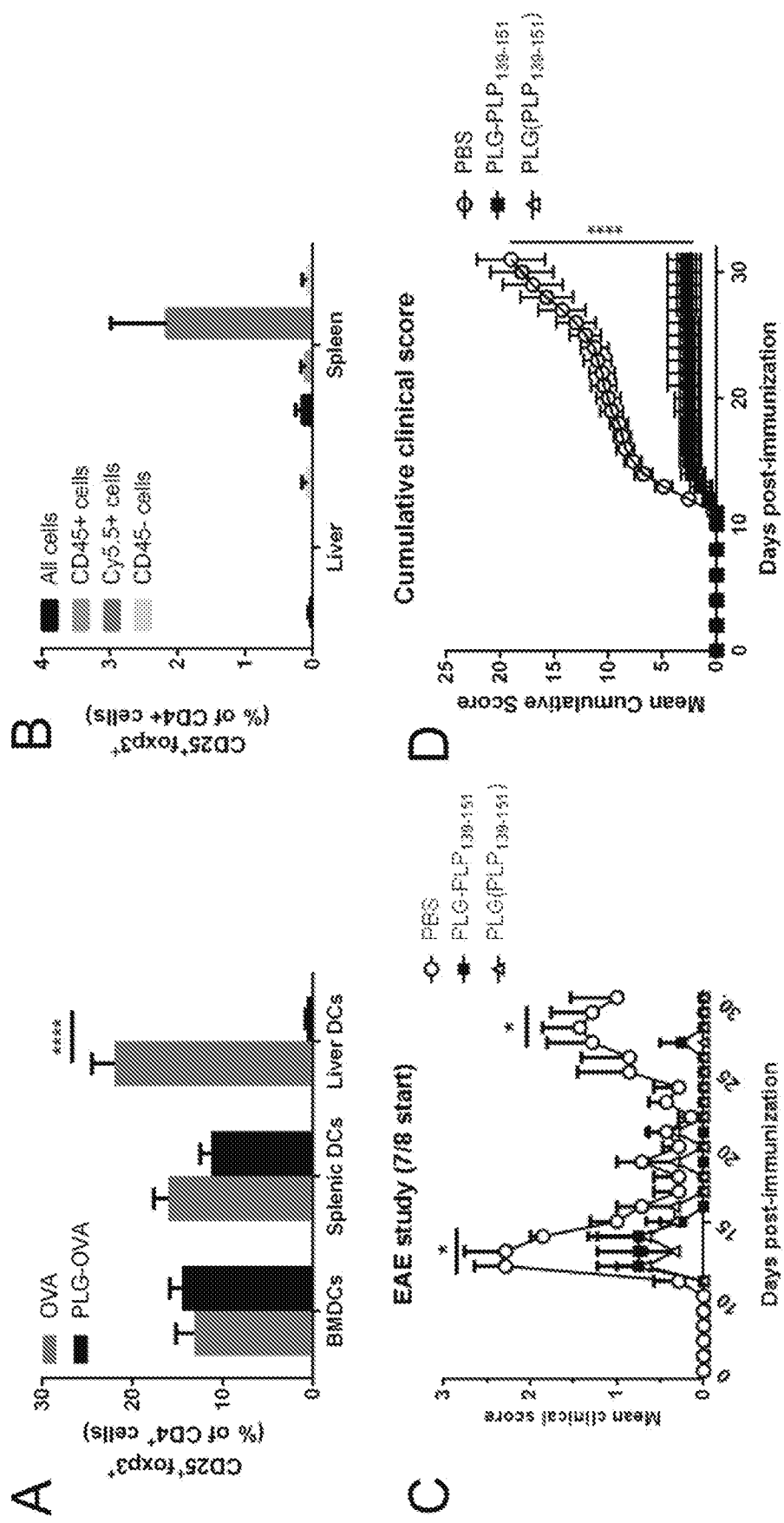
FIG. 10 shows that PLG particles induce regulatory T cells ex vivo and induce tolerance in experimental autoimmune encephalitis (EAE). BMDCs, splenic dendritic cells or liver dendritic cells were treated for 12-24 hr with 0.1 µg/mL of either OVA alone or 0.1 µg/mL PLG-OVA nanoparticle formulations (0.01-10 µg/mg PLG antigen loading). Flow cytometry was used to measure CD25 activation and foxp3 expression of T cells as indication of induction of regulatory T cells (FIG. 10A). Mice were injected intravenously with 1.25 mg of PLG-Cy5.5 nanoparticle formulations. Flow cytometry was used to measure CD25 activation and foxp3 expression of T cells as indication of induction of regulatory T cells 24 hr after injection (FIG. 10B). The peptides administered to the animals were covalently coupled to particles with a diameter of 200-1200 nm. Mice were treated with either PLP$_{139\text{-}151}$-PLG (N=5) or PBS buffer on day −7 relative to the time of immunization (day 0). Peak disease was typically observed around day 12 to 14, and mice were scored for clinical disease. PBS buffer only did not prevent disease induction. However, PLG particles covalently coupled with PLP$_{139\text{-}151}$ or derived from PLGA covalently linked with antigen produced a clinical score of 0 (no disease) at all except low clinical scores of under 1 exhibited between days 20 and 30 (FIG. 10C). Treatment of mice with nanoparticle formulation resulted in significant abrogated clinical disease scores as measured by cumulative disease scores on days 0-30 post immunization (FIG. 10D). * indicates significance at $p<0.05$.

Liver and splenic dendritic cells were activated with just OVA alone, whereas activation of BMDCs was not significantly different between treatment with OVA versus PLG-OVA (FIG. 10A).

Mice were injected intravenously with 1.25 mg of PLG-Cy5.5 nanoparticle formulations. Data was analyzed by flow cytometry 24 hr after injection. Cells in the spleen exhibiting Cy5.5 fluorescence had the highest level of CD25 activation and foxp3 expression, indicative of regulatory T cell induction (FIG. 10B).

PLG nanoparticles were investigated with the immunodominant proteolipid protein $PLP_{139-151}$ epitope (PLG-$PLP_{139-151}$) to induce tolerance for prevention of Relapsing Experimental Autoimmune Encephalitis (R-EAE). The R-EAE mice were generated as described above.

The peptides administered to the animals were covalently coupled to particles. Mice were treated with either $PLP_{139-151}$-PLG (N=3-7) or PBS buffer on day −7 relative to the time of immunization (day 0). Peak disease was typically observed around day 12 to 14, and mice were scored for clinical disease. PBS buffer only did not prevent disease induction. However, PLG particles covalently coupled with $PLP_{139-151}$ produced a clinical score of 0 (no disease) at all except low clinical scores of under 1 exhibited between days 20 and 30 (FIG. 10C). The cumulative disease scores as measured from 0-30 days post immunization clearly show that treatment of mice with nanoparticle formulations resulted in significantly abrogated clinical disease scores compared to controls (FIG. 10D).

Example 10

Figure 11A:
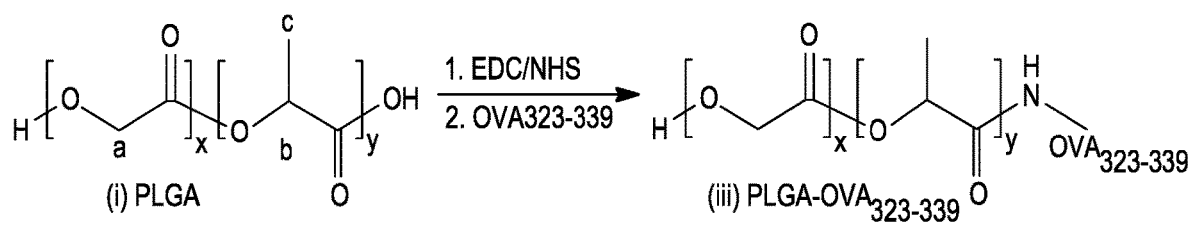
(FIG. 11A) $^1$H-NMR spectrum of (i) PLG, (ii) OVA$_{323\text{-}339}$, and (iii) PLG-OVA$_{323\text{-}339}$ measured in DMSO-d6 (calibrated at 2.5 ppm).
Figure 11A:
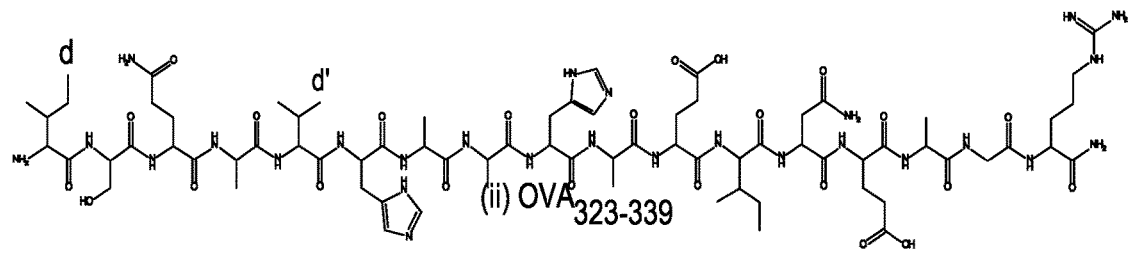
Figure 11A:
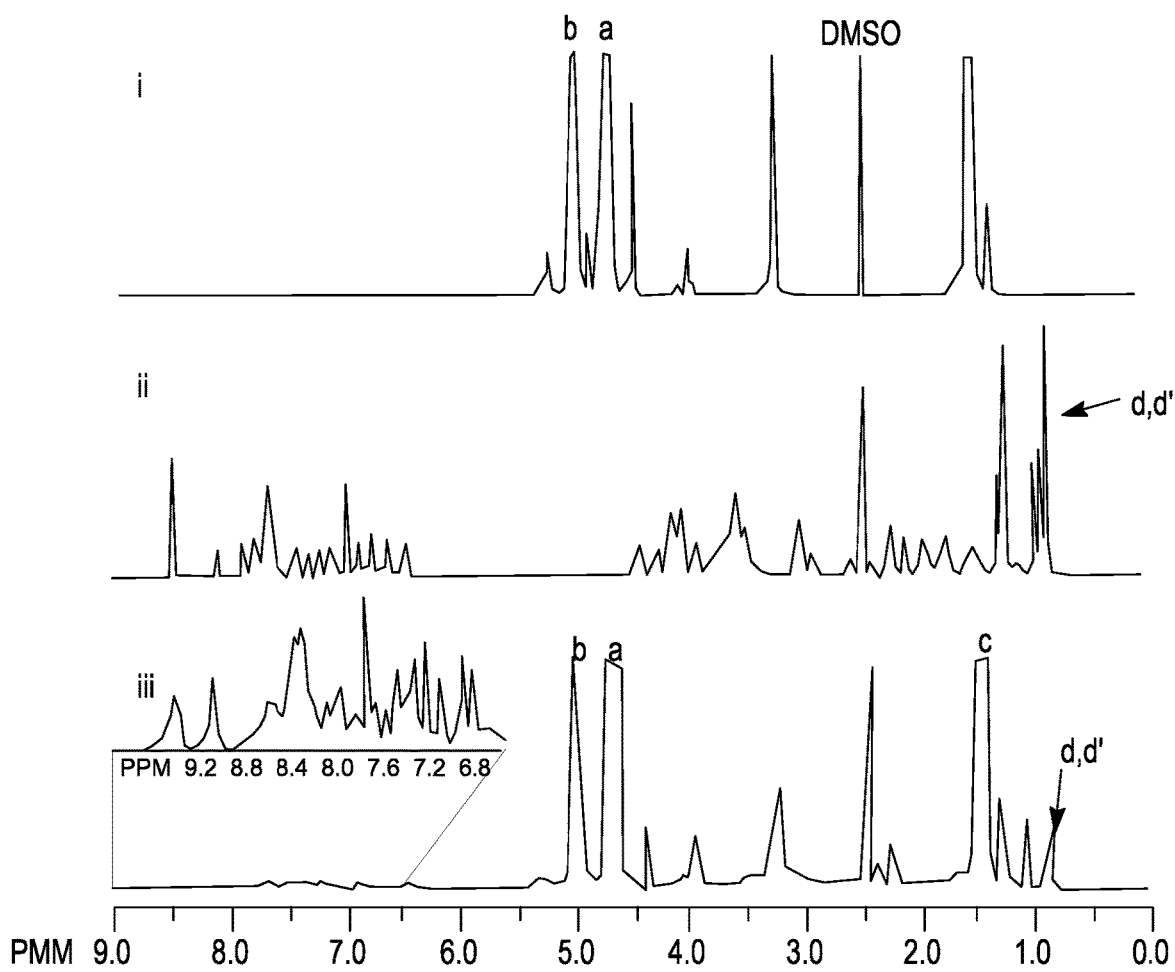
Figures 11B, 11C:
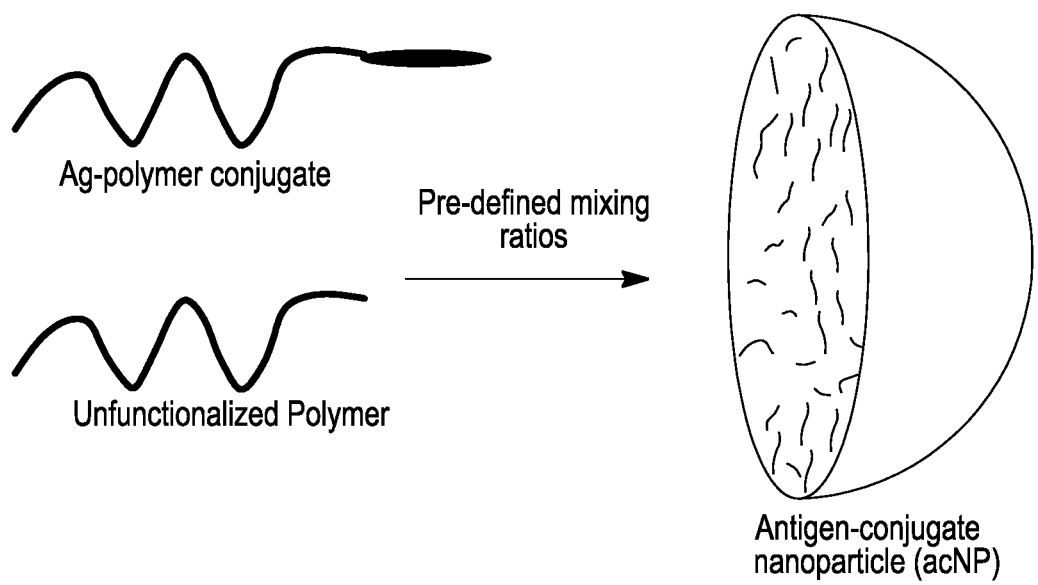
(FIG. 11B) The coupling efficiency of OVA$_{323\text{-}339}$ to PLG was calculated by comparing the integration values of the overlapping methyl proton peaks of leucine and isoleucine present at 1.4 ppm in OVA (d, d') to the methylene proton peak present at 5.3 ppm in PLG (b).
(FIG. 11C) Schematic representation of antigen-conjugate nanoparticles.
Figure 11D:
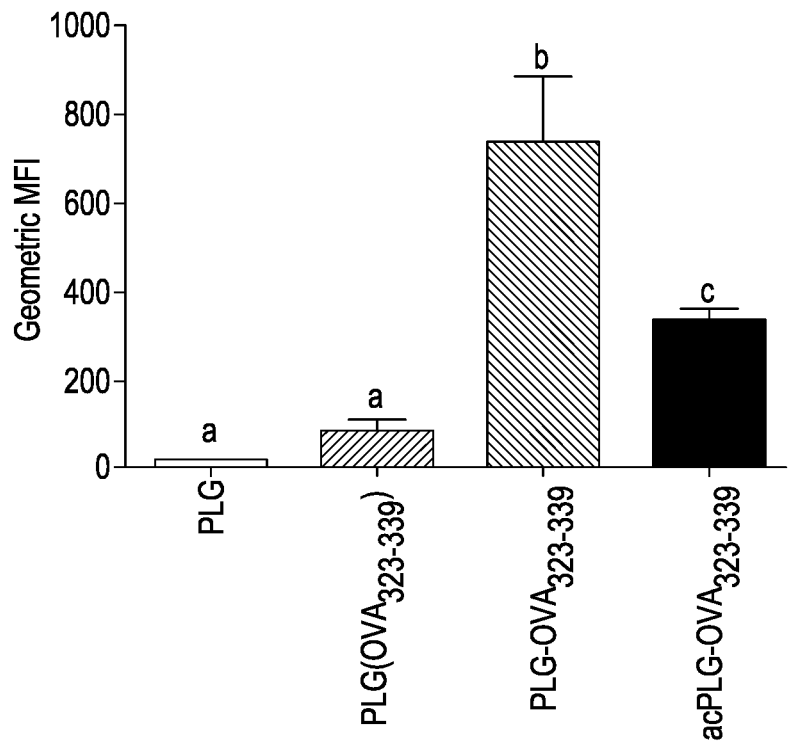
(FIG. 11D) PLG, PLG(OVA), PLG-OVA, and acPLG-OVA were incubated with FITC-labeled anti-OVA$_{323\text{-}339}$ IgG to identify the presence of peptide on the surface of the particles. Results are geometric mean fluorescence intensity.
Figure 11E:
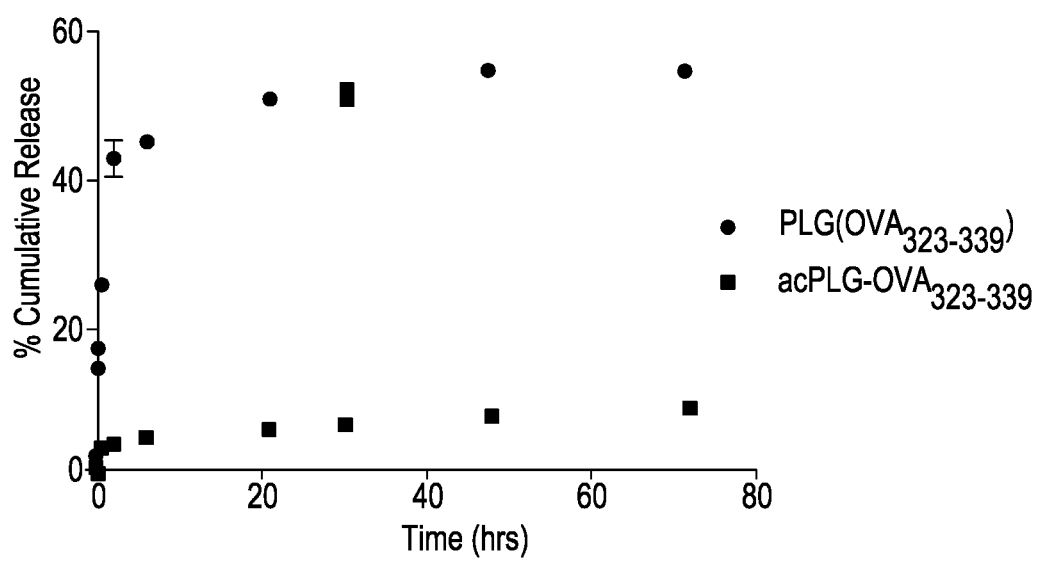
(FIG. 11E) Release profile of PLG(OVA$_{323\text{-}339}$) and acPLG-OVA$_{323\text{-}339}$. $p<0.05$.
Figure 19:
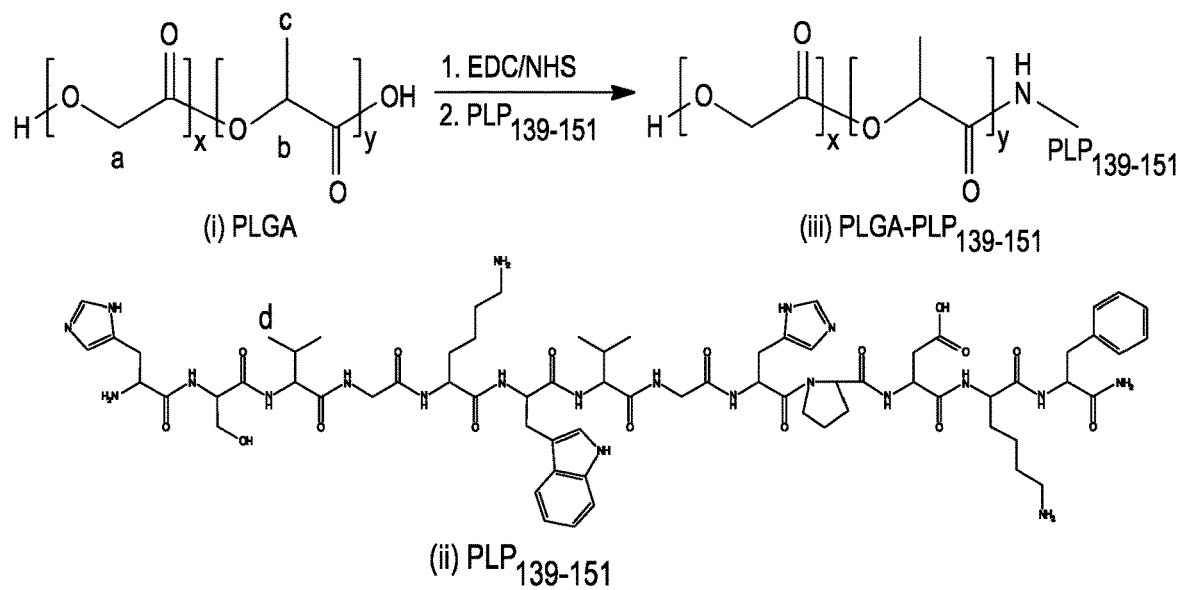
FIG. 19 shows synthesis and characterization of PLGA-$PLP_{139-151}$ conjugates. $^1$H-NMR spectrum of (i) PLGA, (ii) $PLP_{139-151}$, and (iii) PLGA-$PLP_{139-151}$ measured in DMSO-d6 (calibrated at 2.5 ppm).
Figure 19:
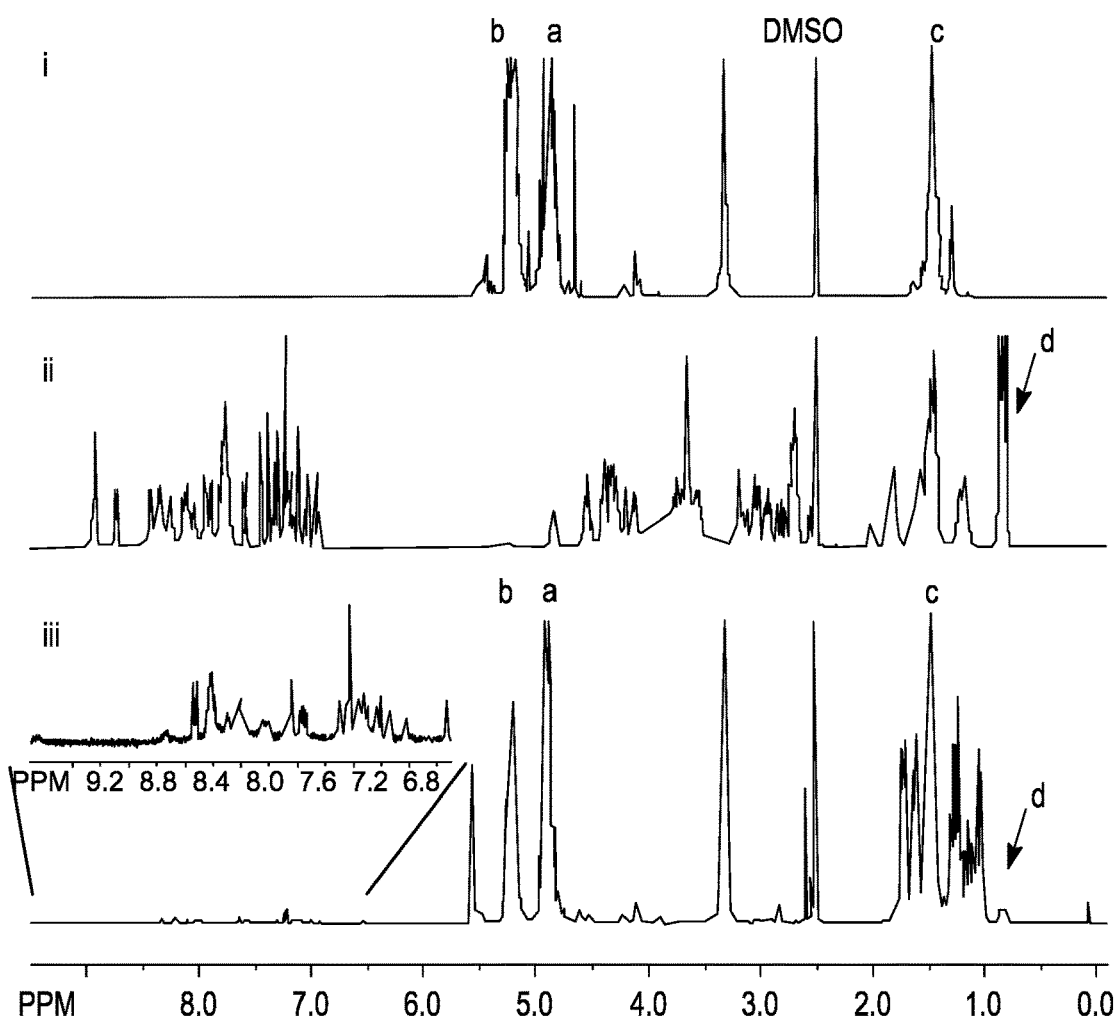
Figure 20:
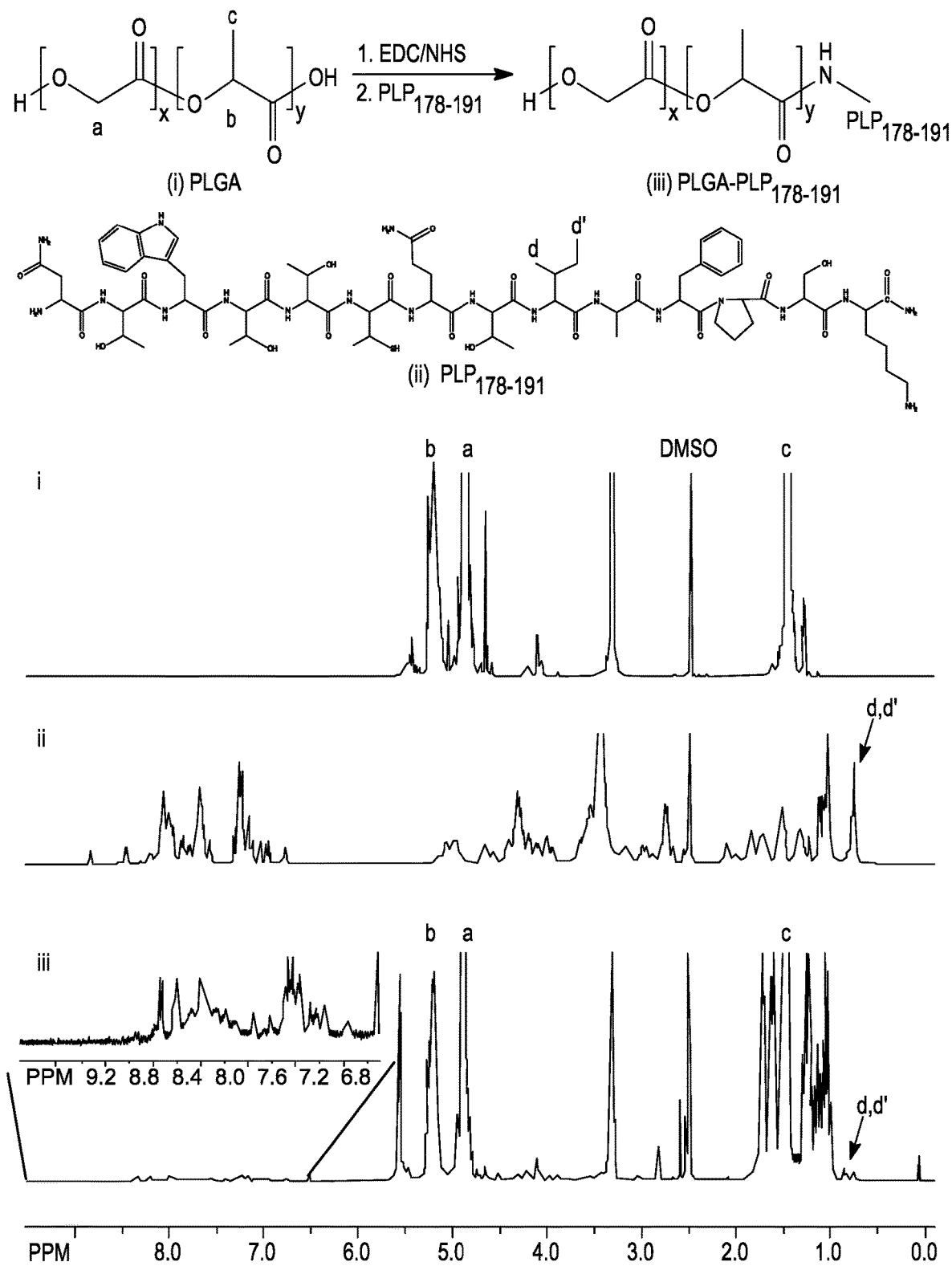
FIG. 20 shows synthesis and characterization of PLGA-$PLP_{178-191}$ conjugates. $^1$H-NMR spectrum of (i) PLGA, (ii) $PLP_{178-191}$, and (iii) PLGA-$PLP_{178-191}$ measured in DMSO-d6 (calibrated at 2.5 ppm).

Controlled Delivery of Single or Multiple Antigens in Tolerogenic Nanoparticles Using Peptide-Polymer Bioconjugates Synthesis of Antigen Polymer Bioconjugates and Particle Preparation Encephalitogenic proteolipid peptides ($PLP_{139-151}$ or $PLP_{178-191}$) and ovalbumin peptide ($OVA_{323-339}$) were conjugated to the terminal carboxylic acid group of PLG (4200 g/mol; 0.17 dL/g) using carbodiimide chemistry (FIG. 11A. FIG. 19, and FIG. 20). Coupling efficiencies were determined by $^1$H-NMR characterization to be 73.6%, 74.1%, and 66.9%, respectively (FIG. 11B). Two sizes (400 nm and 80 nm) of acPLG-Ag particles (antigen-conjugated PLG-Ag particles) were prepared using the solvent evaporation emulsion method (S.E) and nanoprecipitation method, respectively. Ag loadings were controlled by admixing Ag-PLG bioconjugates with unmodified PLG at various ratios (FIG. 11C). Given these coupling efficiencies, a maximum Ag loading (µg of Ag per mg of particle) of 211 µg/mg (266 µg/mg theoretical), 218 µg/mg (274 µg/mg theoretical), and 220 µg/mg (297 µg/mg theoretical) is possible to be achieved for acPLG-$PLP_{139-151}$, acPLG-$PLP_{178-191}$, and acPLG-$OVA_{323-339}$, respectively. The size of the acPLG-Ag particles prepared by the S.E. method was minimally affected by varying the Ag loading to 25 µg/mg, but increased slightly with antigen loadings of 50 µg/mg and higher (Table 4). However, surface coupling of Ag to PLG particles led to significantly increased size and polydispersity. The sizes for particles prepared by nanoprecipitation trended upwards depending on Ag loading and a maximum loading of only 2 µg/mg could be achieved. The zeta potential was not impacted by the Ag loading and was highly negative for all acPLG particles (between −30 to −56 mV). These experiments confirmed that acPLG particles could be prepared with controllable Ag loadings through systematic combination of PLG-Ag bioconjugates with unmodified PLG with well-controlled physicochemical properties.

acPLG particles were compared to Ag-coupled PLG particles (PLG-Ag), and Ag-encapsulated PLG particles (PLG (Ag)) for Ag-specific antibody binding to their surface using a fluorescence-tagged $OVA_{323-339}$-IgG1. Encapsulation of Ag into particles (PLG(Ag)) has been demonstrated to reduce the potential for antibody binding to particle that could result in immune activation in vivo. Binding to the surface of the three particle variations demonstrated significantly less binding of IgG1 to acPLG-$OVA_{323-339}$ (8 µg/mg) than PLG-$OVA_{323-339}$ particles (7.5 µg/mg) (FIG. 1D). Ag-encapsulated PLG($OVA_{323-339}$) bound the least amount of IgG1, however a maximal antigen loading of only 3 µg/mg was achievable. The decreased IgG1 binding is suspected to result from the significantly lower Ag loading and burst release of Ag, that was similarly observed for other PLG particles Importantly, acPLG particles did not display any significant burst release of Ag compared to PLG(Ag) particles (FIG. 11E).

Figure 12:
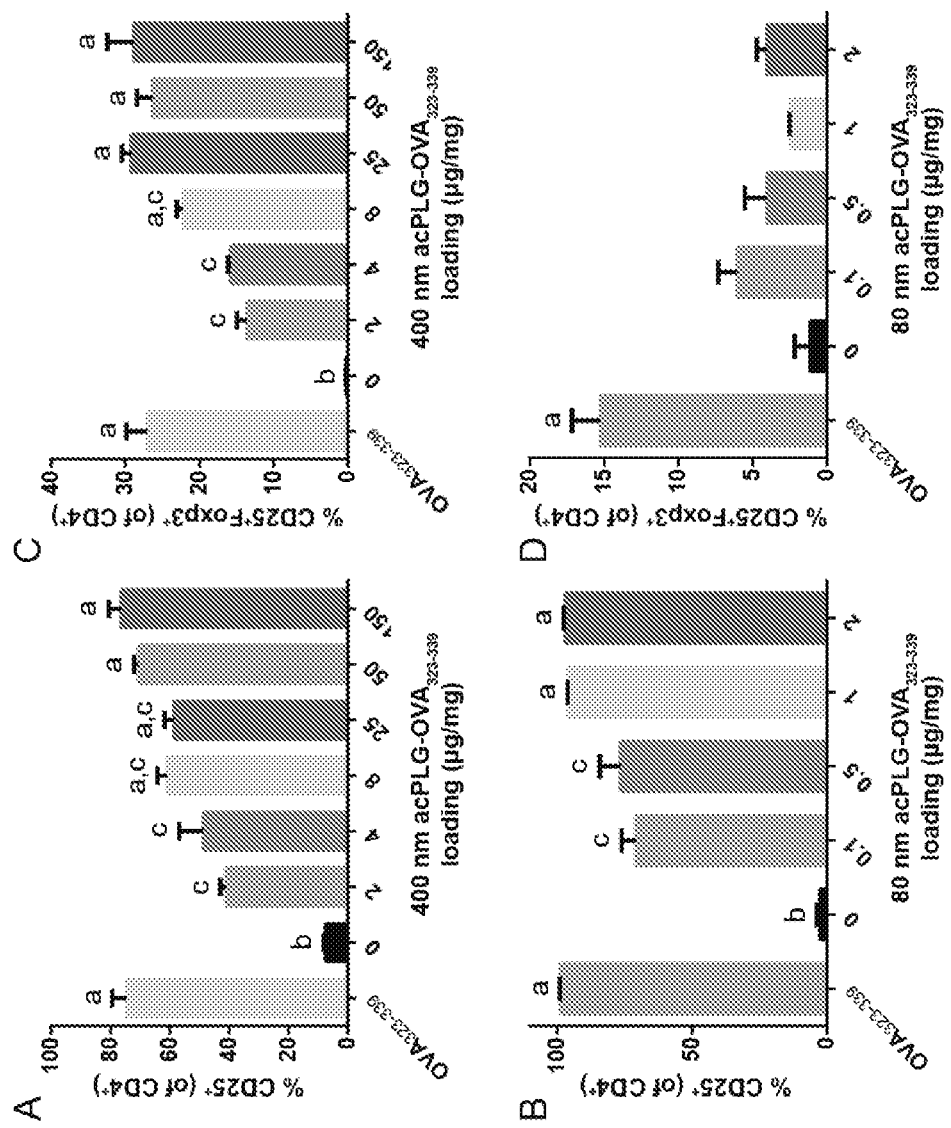
FIG. 12 shows that regulatory T cell induction in vitro is dependent on nanoparticle size and Ag loading. Bone marrow-derived dendritic cells were treated for 3 h with 300 µg/mL of 400 nm (FIG. 12A and FIG. 12C) and 80 nm (FIG. 12B and FIG. 12D) acPLG-OVA$_{323\text{-}339}$ particles. Excess acPLG-OVA$_{323\text{-}339}$ particles were subsequently washed from the wells prior to addition of naïve CD4$^+$ OT-II T cells and 2 ng/mL of TGF-β. Cells were co-cultured for 4 days prior to flow cytometric analysis. Single, live, CD4+ cells were examined for CD25 and Foxp3 expression.

Regulatory T Cell Induction by acPLG-Ag Particles is Size and Ag Loading-Dependent The ability of acPLG-Ag particles to promote antigen presentation by dendritic cells and subsequently influence the activation of naïve $CD4^+CD25^-$ T cells and induce the formation of regulatory T cells (Tregs) was next investigated in vitro as a function of particle size and Ag loading. Treg induction was used to determine tolerogenic effects of acPLG particles because they have been shown to mediate immune tolerance in vivo. Delivery of both 80 and 400 nm acPLG-$OVA_{323-339}$ particles to bone-marrow derived dendritic cells (BMDCs) followed by co-culture with Ag-specific naïve OTII $CD4^+CD25^-$ T cells in the presence of TGFβ resulted in upregulation of CD25 on T cells, even at the lowest Ag loading conditions tested (FIGS. 12A and 12B). Although CD25 expression was increased by both acPLG-$OVA_{323-339}$ particle sizes, it did not correlate with Treg induction as measured by CD25 and Foxp3 expression. Tregs were induced at high levels only with the 400 nm acPLG-$OVA_{323-339}$ particles, and was dependent on Ag loading (FIG. 12C). At a NP concentration of 300 µg/mL, maximal Treg induction was observed at an Ag loading of 8 µg/mg and there was no significant difference observed by increasing the loading to 150 µg/mg. acPLG-$OVA_{323-339}$ particles with a diameter of 80 nm, regardless of Ag loading, only induced low levels of Tregs (FIG. 12D). Taken together, the T cell expression of CD25 was particle size independent and induction of Tregs was particle size dependent. Importantly, we found that at high concentrations, acPLG-$OVA_{323-339}$ particles up to 150 µg/mg loading were not significantly different than particles with 8 µg/mg loading for inducing Tregs in vitro.

Figure 13:
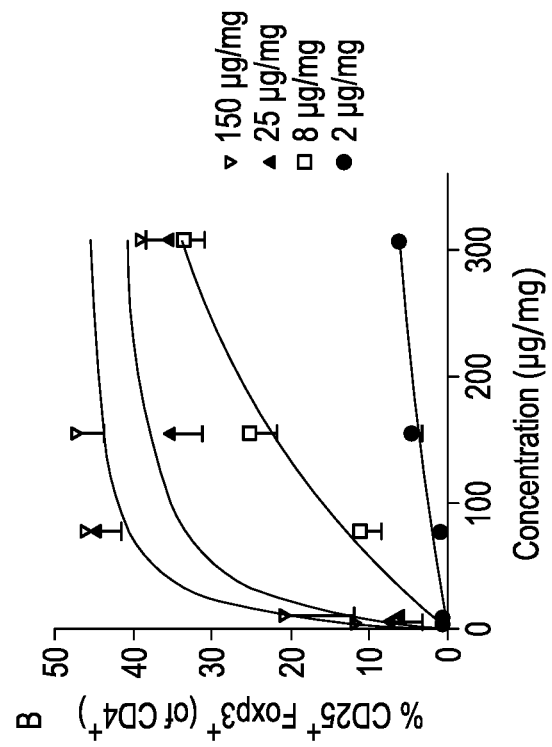
FIG. 13 shows that regulatory T cell induction is dependent on nanoparticle concentration. Bone marrow-derived dendritic cells were treated for 3 hr with various concentrations of 400 nm of PLG-OVA nanoparticles (8 µg/mg loading) formulation. Excess acPLG-OVA$_{323\text{-}339}$ particles were subsequently washed from the cell surface prior to addition of OT-II T cells and 2 ng/mL of TGF-β1. The cells were co-cultured for 4 days prior to using flow cytometry to measure CD25 activation (FIG. 13A) and Foxp3 expression (FIG. 13B) of T cells.
Figure 13:
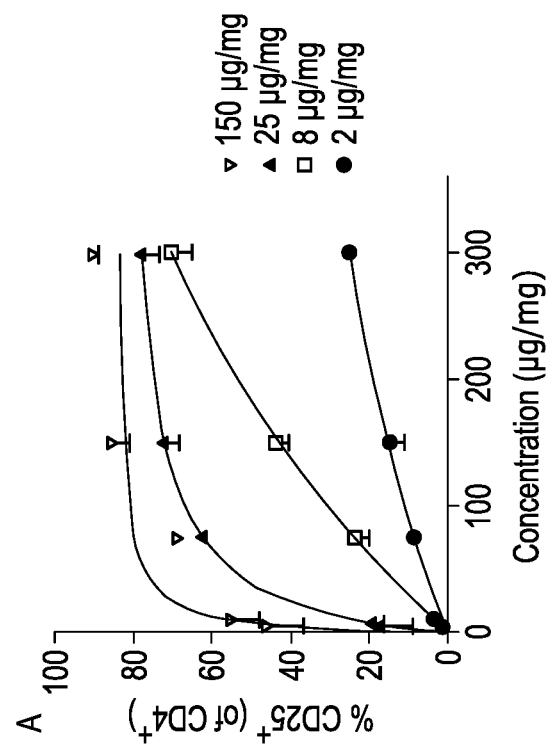

Regulatory T Cell Induction by acPLG-Ag Nanoparticles is Particle Concentration-Dependent The concentration dependency of acPLG particles on the activation of naïve $CD4^+CD25^-$ T cells and induction of Tregs was tested using S.E. acPLG-$OVA_{323-339}$ at multiple Ag loadings (2, 8, 25, 150 µg/mg) and particle concentrations (0, 5, 10, 75, 150, and 300 µg/mL). The range of Ag delivered to the BMDCs varied from 10 to 45,000 ng/mL (Table 4). A minimum of 1,200 ng/mL of Ag was required to achieve CD25 expression in greater than 40% of CD4 T cells. This level of expression was achieved even at low acPLG concentrations (5-10 µg/mL) with 150 µg/mg Ag loading (FIG. 13A). Similar CD25 expression was achieved using acPLG particles with 8 µg/mg Ag loading at a NP concentration of 150 µg/mL (1,200 ng/mL Ag delivered). CD25 expression over 60% of CD4 T cells occurred for an Ag concentration of 1,875 ng/mL or greater. Foxp3 expression on $CD4^+CD25^+$ T cells required a larger amount of Ag to reach the highest expression levels (over 30%). Treg induction correlated to levels of CD25 expression greater than 60% of CD4 T cells. Treg induction by acPLG-$OVA_{323-339}$ particles was highly dependent on the total amount of Ag delivered per well. Additional Ag delivered over 1,875 ng/mL did not dramatically influence the percentage of Tregs detected in vitro (FIG. 13B). acPLG particles prepared with various Ag loadings enabled the Ag requirements to induce significant levels of Tregs in vitro to be determined and presents the possibility to utilize acPLG particles to modulate biological responses in vivo.

TABLE 4

Concentration of antigen delivered per well as a function of acPLG-$OVA_{323-339}$ particle concentration and loading. Bolded and italicized cells represent the protein loadings evaluated in FIG. 13.

| Particle loading (µg/mg) | Concentration (µg/mg) | | | | | |
| --- | --- | --- | --- | --- | --- | --- |
| | 0 | 5 | 10 | 75 | 150 | 300 |
| 0 | 0 | 0 | 0 | 0 | 0 | 0 |
| 2 | 0 | 10 | 20 | 150 | 300 | 600 |
| 4 | 0 | 20 | 40 | 300 | 600 | 1200 |
| *8* | 0 | 40 | 80 | 600 | 1200 | 2400 |
| *25* | 0 | 125 | 250 | 1875 | 3750 | 7500 |
| 50 | 0 | 250 | 500 | 3750 | 7500 | 15000 |
| *150* | 0 | 750 | 1500 | 11250 | 22500 | 45000 | acPLG-Ag Particles Suppress EAE Induced by $PLP_{139-151}$ Immunization

Figure 14:
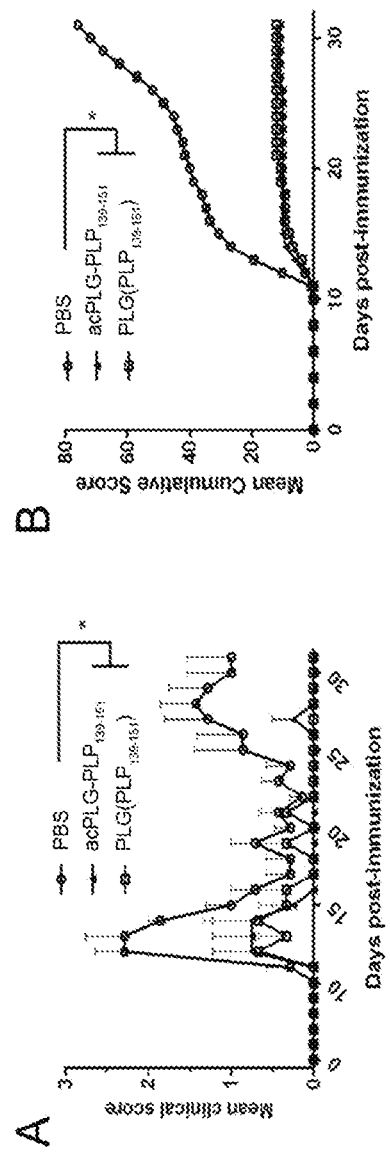
FIG. 14 shows that acPLG(Ag) nanoparticles prophylactically induce tolerance in R-EAE. Clinical scores for SJL/J mice treated with PBS (control), 2.5 mg of PLG(PLP$_{139\text{-}151}$) (1.4 µg/mg PLP) or 1.25 mg of acPLG-PLP$_{139\text{-}151}$ (8 µg/mg PLP$_{139\text{-}151}$) and immunized with PLP$_{139\text{-}151}$/CFA to induce R-EAE 7 days later.

The ability of acPLG-Ag particles to induce Ag-specific immune tolerance was tested using the R-EAE disease model of MS. While the in vitro data support particle internalization, Ag presentation, and Treg induction, the in vivo study is more challenging since the NPs must reach the appropriate cell types to elicit a tolerogenic response. In previous studies, Ag-encapsulated PLG($PLP_{139-151}$) particles were administered with Ag loading of approximately 2-3 µg/mg at a dose of 2.5 mg. Using a prophylactic disease model, acPLG-$PLP_{139-151}$ particles were administered intravenously to SJL/J mice on day −7 relative to R-EAE immunization. Untreated control mice displayed severe clinical symptoms, whereas acPLG-$PLP_{139-151}$ particle-treated mice displayed significantly reduced disease symptoms as measured by both the mean clinical score (FIG. 14A) and cumulative clinical score (FIG. 14B). Furthermore, the acPLG-$PLP_{139-151}$ particles demonstrated similar effectiveness as Ag-encapsulated PLG($PLP_{139-151}$) particles given at a dose of 2.5 mg (FIGS. 14A-14B). These results confirmed that the higher Ag loading in acPLG particles could enable the dose of acPLG particles to be reduced with similar abilities to induce tolerance in vivo.

acPLG Particles Suppress EAE Induced with a Cocktail of Encephalitogenic Peptides ($PLP_{139-151}$ and $PLP_{178-191}$)

Figure 15:
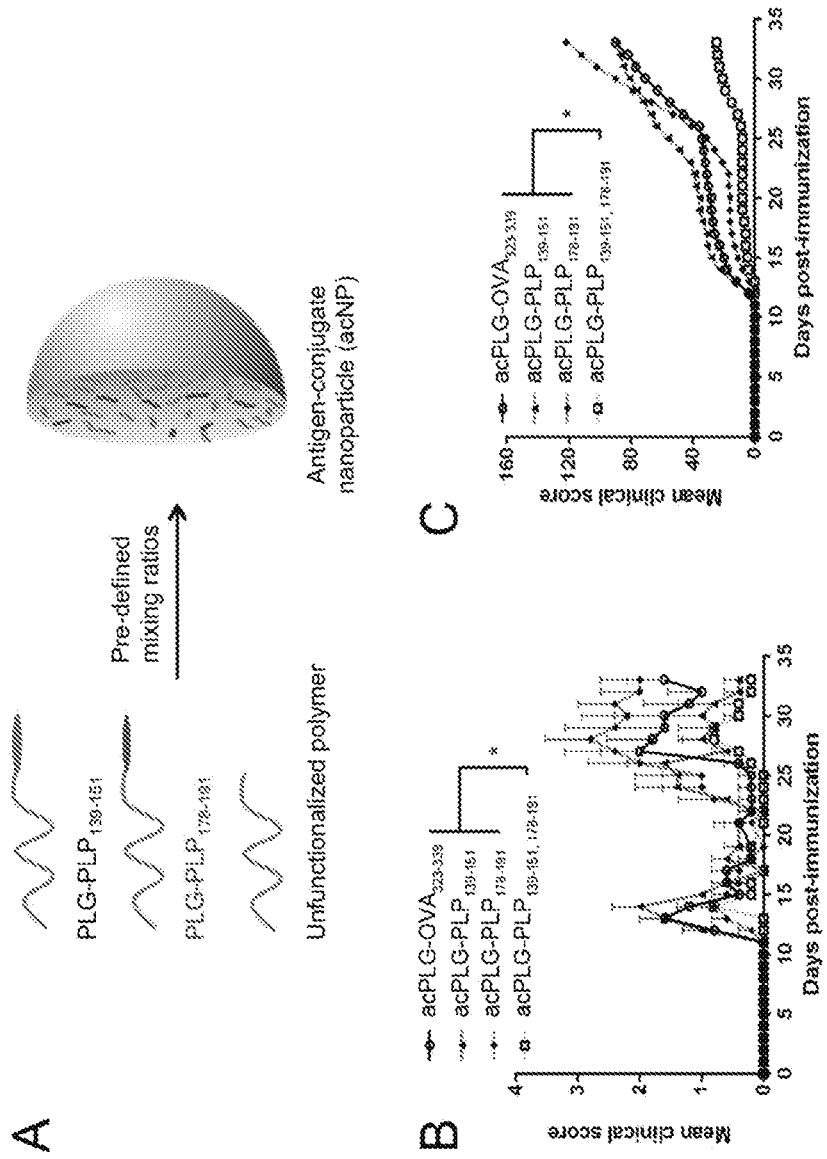
FIG. 15 shows that acPLG(Ag) particles induce protective tolerance against R-EAE induced with cocktail of autoantigens. Clinical scores of SJL/J mice treated with 1.25 mg of pcPLG-OVA$_{323\text{-}339}$ (8 µg/mg OVA$_{323\text{-}339}$), pcPLG-PLP$_{139\text{-}151}$ (8 µg/mg PLP$_{139\text{-}151}$), pcPLG-PLP$_{178\text{-}191}$ (8 µg/mg PLP$_{178\text{-}191}$), or pcPLG-PLP$_{139\text{-}151,178\text{-}191}$ (8 µg/mg PLP$_{139\text{-}151}$ and 8 µg/mg PLP$_{178\text{-}191}$) and immunized with PLP$_{139\text{-}151}$ and PLP$_{178\text{-}191}$ in CFA to induce R-EAE 7 days later.
Figure 16:
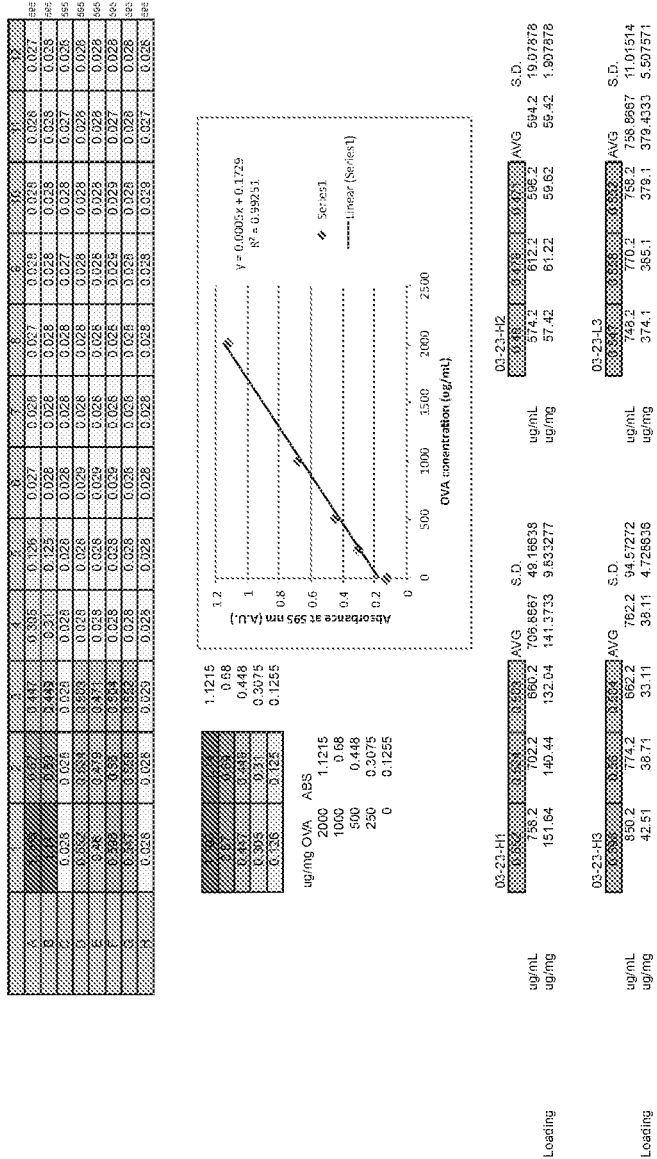
FIG. 16 shows BCA assay raw data for determination of protein content per mg of PLGA-OVA conjugate.
Figure 17:
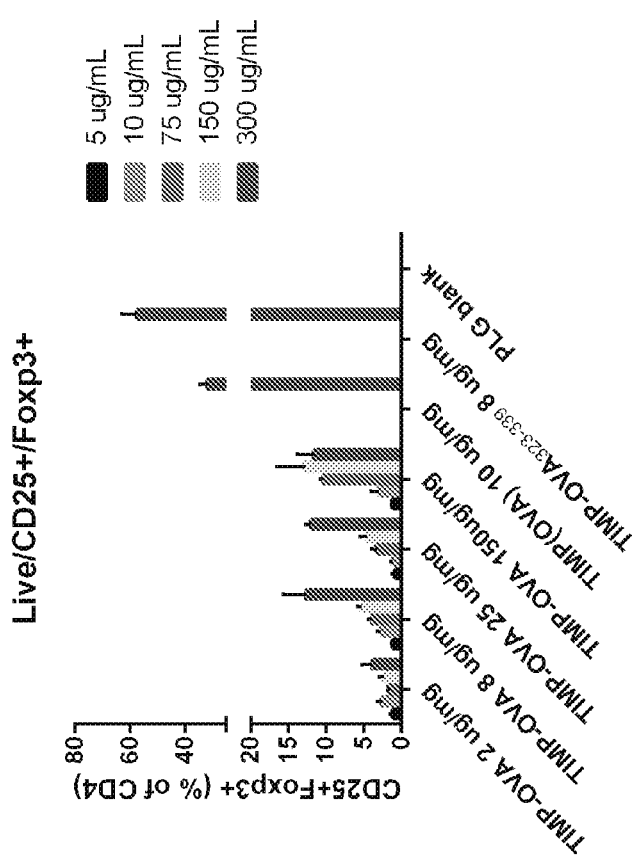
FIG. 17 shows CD25+Foxp3+ cell percentage of CD4+ T cells.
Figure 18:
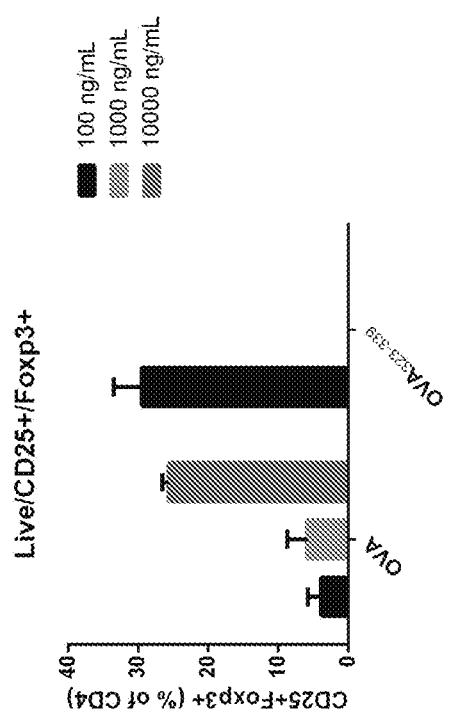
FIG. 18 shows CD25+Foxp3+ cell percentage of CD4+ T cells.

Diversity in the autoreactive T cell repertoire has been well established in autoimmune diseases such as MS; therefore, tolerogenic NPs will likely need to deliver multiple epitopes to effectively treat a disease whose pathogenesis can be complex. We tested if multiple myelin peptide—PLG bioconjugates, namely PLG-$PLP_{139-151}$ and PLG-$PLP_{178-191}$, could be incorporated into a single acPLG particle at precise Ag loadings and be used as an effective treatment for R-EAE induced by immunization with $PLP_{139-151}$/$PLP_{178-191}$/CFA (FIG. 15A).

acPLG particles were administered intravenously to SJL/J mice on day −7 relative to R-EAE immunization. Control mice, treated with acPLG-OVA$_{323-339}$, acPLG-PLP$_{139-151}$, or acPLG-PLP$_{178-191}$ particles, displayed severe clinical disease symptoms compared to acPLG-PLP$_{139-151,178-191}$ particles as measured by both the mean clinical score (FIG. 15B) and cumulative clinical score (FIG. 15C). Interestingly, the acute disease of mice treated with acPLG-PLP$_{139-151}$ particles displayed a strong acute disease phase and a less severe relapse. This result was in contrast to mice treated with acPLG-PLP$_{178-191}$ particles where a reduced acute disease was observed and a severe relapse occurred. Mice treated with acPLG-PLP$_{139-151,178-191}$ displayed significantly reduced acute and relapse disease scores that resulted in a major diminishment in the measured cumulative scores. These results demonstrate the ability for acPLG particles to simultaneously tolerize against multiple peptides associated with the pathogenesis of disease. The modular design of acPLG particles incorporating various Ags using a PLG-Ag bioconjugate "mix-and-match" approach clearly demonstrates the versatility of the acPLG particle platform and design.

Soluble peptide, Ag-coupled cells, genetically engineered food products, and particles have been investigated as treatment options for applications including allergy, autoimmune disease, and cell transplantation. An advantage of the particles of the current invention (acPLG particles) over current nano-based tolerance platforms is that tolerance induction by acPLG particles is achieved without co-delivery of immunosuppressive agents that have been associated with many side effects. Differences in uptake mechanism and context of Ag presentation of acPLG particles may partially account for platforms such as soluble Ag arrays, tolerogenic nanoparticles (tNPs), and PEGylated gold nanoparticles requiring co-delivery of various immunomodulatory agents to induce tolerance. The results presented herein demonstrate a novel NP platform that achieves precise control over Ag delivery and tolerogenic responses in vivo. This controllable Ag delivery platform enabled the identification of the relationship between Ag loading, concentration, and size of acPLG particles with respect to the activation of T cells and induction of Tregs in vitro.

Materials and Methods:

Poly(lactide-co-glycolide) (50:50) (PLG) with a single carboxylic acid end-group and an inherent viscosity of 0.17 dL/g in hexafluoro-2-propanol was purchased from Lactel Absorbable Polymers (Birmingham, Ala.). Poly(ethylene-alt-maleic anhydride) (PEMA) was purchased from Polyscience, Inc. (Warrington, Pa.). Amine-terminated ovalbumin peptide (NH$_2$-OVA$_{323-339}$) and proteolipid peptide (NH$_2$-PLP$_{139-151}$ or NH$_2$-PLP$_{178-191}$) was purchased from Genscript (Piscataway, N.J.). All other reagents were purchased from Sigma Aldrich (St. Louis, Mo.) unless noted otherwise.

PLG-Ag Bioconjugation

PLG (37.8 mg, 0.009 mmol, 4200 g/mol) of was dissolved in 2 mL of N,N-dimethylformamide (DMF) in a 20 mL scintillation vial equipped with a stir bar. N-(3-Dimethylaminopropyl)-N'-ethylcarbodiimide hydrochloride (EDC) (9.0 mg, 0.047 mmol, 5× to PLG) was dissolved in 0.5 mL of DMF and added dropwise to the PLG solution. N-Hydroxysuccinimide (NHS) (5.5 mg, 0.047 mmol, 5× to PLG) was dissolved in 0.5 mL DMF and added dropwise to the solution. The reaction was allowed to stir for 15 minutes at room temperature. Antigenic peptide (1.2× to PLG) was dissolved in a solution of 1 mL dimethyl sulfoxide (DMSO) and 0.5 mL DMF and stirred at 400 RPM. Triethylamine (5× to peptide) was added to peptide solution and the mixture was added dropwise to the stirring PLG solution. The reaction was allowed to proceed overnight at room temperature. The resulting polymer was isolated and purified by dialysis using 3,500 molecular weight cut-off membrane against four liters of distilled water over two days. Distilled water was replaced a total of six times. The dialyzed polymer was collected and washed with MilliQ water three times MilliQ water by centrifugation at 7000×g before resuspension in 20 mL of water and lyophilization for two days. Coupling efficiency peptide to PLG was determined by NMR analysis in DMSO-d6.

Mice

Female SJL/J mice (6-8 weeks) were purchased from Harlan Laboratories (Indianapolis, Ind.). OT-II mice (B6.Cg-Tg(TcraTcrb)425Cbn/J) were purchased from Jackson Laboratory (Bar Harbor, Me.).

Nanoparticle Preparation

Nanoparticles (acPLG) of two different sizes (80 and 400 nm) were prepared following either the nanoprecipitation or emulsion solvent evaporation method, respectively. To produce acPLG particles using the emulsion solvent evaporation method, Ag-polymer bioconjugates were combined with unconjugated PLG at various ratios to give calculated Ag loadings in particles as described in Table 4. The method has been described in our previous publications. To prepare smaller, approximately 80-120 nm acPLGs, the nanoprecipitation method was employed. Briefly, 100 mg of PLG (Ag-polymer bioconjugates and unconjugated PLG at desired ratios) was dissolved in acetonitrile at a concentration of 1 mg/mL and poured into 300 mL of MilliQ water under rapid stirring. The solutions were stirred for 24-48 h to completely remove residual acetonitrile. The acPLG particles were recovered using an ultracentrifuge membrane filter 10 kDa MWCO at 4000×g. Cryoprotectants (4% (w/v) sucrose and 3% (w/v) mannitol) were then added to the particles before lyophilization.

Nanoparticle Characterization

The size and zeta potential of the nanoparticles was determined by dynamic light scattering (DLS) by mixing 10 μL of a 25 mg/mL particle solution into 990 μL of MilliQ water using a Malvern Zetasizer ZSP (Westborough, Mass.). The release of peptide from PLG(OVA$_{323-339}$) and acPLG-OVA$_{323-339}$ particles was measured over 72 hr. Approximately 8 mg of each particle was dispersed in 1 mL of PBS and incubated at 37° C. At pre-determined time points, the particles were centrifuged at 7000×g for 5 min and 0.5 mL of supernatant was collected. The particles were resuspended and 0.5 mL of fresh PBS was added to each sample. All supernatant samples were stored at −20° C. until the experiment was completed. After the final time point, the pellet of particles was dissolved in DMSO and the total amount of remaining protein was determined. Protein content was determined using the Micro BCA assay (Pierce, Waltham, Mass.).

OVA$_{323-339}$-IgG1 Binding In Vitro

OVA$_{323-339}$ antibody (Innovagen, Sweden) was fluorescently labeled with FITC using Abcam Easy Link FITC Conjugation Kit (Abcam, Cambridge, Mass.). 20 μg of acPLG particles were incubated with 1 mg/mL FITC-labeled OVA$_{323-339}$ antibody for 20 mM at 4° C. and washed. Fluorescence was measured using a Beckman Coulter CyAn ADP Analyzer (Indianapolis, Ind.). Statistical differences between groups was determined by performing a one-way ANOVA and Tukey's Post-hoc test ($p<0.05$).

Cell Culture

BMDC media consisted of RPMI containing L-glutamine (Life Technologies, Carlsbad, Calif.) supplemented with penicillin (100 units/mL), streptomycin (100 mg/mL), 10% heat-inactivated fetal bovine serum (FBS) (Invitrogen Corporation, Carlsbad, Calif.) and 50 mM β-mercaptoethanol (Sigma Aldrich). Co-culture media was the same without β-mercaptoethanol and supplemented with 1 mM sodium pyruvate, and 0.1 mM non-essential amino acids (Life Technologies, Carlsbad, Calif.).

Antibodies and Flow Cytometry

FcR blocking was performed with anti-CD16/32 (Biolegend) prior to staining with various combinations of the following antibodies: anti-CD4 (RM4-5), -CD25 (PC61) (Biolegend), and -Foxp3 (FJK-165) (eBioscience, San Diego, Calif.). Viability was assessed with fixable violet dead cell stain kit (Invitrogen, Carlsbad, Calif.). Foxp3 staining was performed with eBioscience staining kit according to the manufacturer's protocol. Cytometric data were collected using a Beckman Coulter CyAn ADP Analyzer. Analysis was performed using FlowJo (FlowJo, Ashland, Oreg.).

Cell Isolation and In Vitro Treg Induction Assay

Treg induction assays were carried out with slight modifications as described. $CD4^+CD25^-Foxp3^-$ T cells were isolated from the spleen of OT-II mice using a naïve $CD4^+$ T cell isolation kit (Miltenyi Biotec, San Diego, Calif.). The assay was carried out in T cell media. Bone marrow-derived dendritic cells ($2\times10^4$/well) were seeded into 96-well round-bottom cell culture plates and incubated with acPLG-$OVA_{323-339}$ of various particle concentrations and Ag loadings for 3 hours. Following incubation, all wells were washed to remove excess particles that had not been internalized by cells. Cells were co-cultured with $2\times10^4$/well naïve T cells in the presence of 2 ng/mL TGF-β1 (Cell Signaling Technology, Danvers, Mass.). Groups receiving antigen in lieu of acPLG-$OVA_{323-339}$ received soluble $OVA_{323-339}$ (100 ng/mL) at this time. After 4 days of co-culture, the T cells were collected, stained for viability, CD4, CD25, and Foxp3, and analyzed using flow cytometry. Statistical differences between groups was determined by performing a one-way ANOVA and Tukey's Post-hoc test ($p<0.05$).

R-EAE Disease Induction and Measurement

R-EAE was induced by immunization with encephalitogenic peptides as previously described. To induce R-EAE with $PLP_{139-151}$ or both $PLP_{139-151}$ and $PLP_{178-191}$, mice were immunized by s.c. administration of 100 μL of 1 mg/mL $PLP_{139-151}$/complete Freund's adjuvant (CFA) or 0.25 mg/mL of $PLP_{139-151}$/CFA and 0.5 mg/mL of $PLP_{178-191}$/CFA, respectively, distributed over 3 spots on the nape and hind flanks of SJL/J mice. Disease severity in individual mice was assessed using a 0 to 5 point scale: 0=no disease, 1=limp tail or hind limb weakness, 2=limp tail and hind limb weakness, 3=partial hind limb paralysis, 4=complete hind limb paralysis, 5=moribund. Differences between disease courses of different treatment groups were analyzed for statistical significance using the Kruskal-Wallis test.

TABLE 5

Size and zeta potential of the nanoparticle formulations used in this study. Ag loading (μg Ag/mg PLG) was precisely controlled by combining PLG-Ag conjugates with unconjugated PLG at predetermined mixing ratios.

| Particle | Loading (μg/mg) | Size (nm ± S.D.) | Zeta (mV ± S.D.) |
|---|---|---|---|
| PLG | 0 | 521.5 ± 23.0 | −56.0 ± 0.7 |
| acPLG-$OVA_{323-339}$ | 2 | 322.0 ± 4.0 | −49.9 ± 4.9 |
| acPLG-$OVA_{323-339}$ | 4 | 326.6 ± 5.8 | −44.7 ± 1.5 |
| acPLG-$OVA_{323-339}$ | 8 | 321.5 ± 8.5 | −43.8 ± 1.8 |
| acPLG-$OVA_{323-339}$ | 25 | 345.5 ± 5.2 | −37.9 ± 0.4 |
| acPLG-$OVA_{323-339}$ | 50 | 468.0 ± 6.5 | −36.4 ± 0.7 |
| acPLG-$OVA_{323-339}$ | 150 | 558.1 ± 5.3 | −38.9 ± 0.5 |
| acPLG-$PLP_{139-151}$ | 8 | 656.5 ± 13.7 | −45.5 ± 1.4 |
| acPLG-$PLP_{178-191}$ | 8 | 490.9 ± 15.0 | −51.3 ± 1.0 |
| acPLG-$PLP_{139-151, 178-191}$ | 16* | 454.7 ± 17.4 | −45.0 ± 0.9 |
| PLG($PLP_{139-151}$) | 1.4 | 384.7 ± 10.4 | −45.9 ± 0.8 |
| PLG | 0 | 72.2 ± 1.9 | −33.5 ± 1.1 |
| acPLG-$OVA_{323-339}$ | 0.1 | 74.8 ± 0.3 | −34.5 ± 0.3 |
| acPLG-$OVA_{323-339}$ | 0.5 | 85.6 ± 1.9 | −31.5 ± 1.2 |
| acPLG-$OVA_{323-339}$ | 1 | 103.9 ± 0.3 | −32.4 ± 0.6 |
| acPLG-$OVA_{323-339}$ | 2 | 112.0 ± 0.6 | −32.0 ± 0.9 |

*ac-PLG-$PLP_{139-151, 178-191}$ particles contained 8 μg/mg of both $PLP_{139-151}$ and $PLP_{178-191}$.

Example 11

Covalent Modification of Ovalbumin Protein with Poly (Lactide-Co-Glycolide), TIMP Formulation, and In Vitro Treg Induction Assay Covalent modification of polymers with proteins offers numerous advantages to improve the physicochemical properties of nanoparticulate drug delivery systems. Importantly, properties such as protein loading as well as nanoparticle size and zeta potential are easier to control.

Ovalbumin contains numerous CD4 ($OVA_{323-334}$, $OVA_{265-280}$), CD8 ($OVA_{257-264}$), and B cell epitopes. One of the outstanding questions is whether TIMP encapsulating complete ovalbumin (TIMP-OVA) is capable of tolerizing all antigenic epitopes on CD4, CD8 and B cells. Because the precise number of these epitopes is known within the ovalbumin protein and the particles being used can exquisitely control the amount of protein and polymer used, the molecular quantities of antigen required to tolerize differential T and B cell receptors can be addressed. As such the dose for different T cell epitopes within the same protein can be addressed.

General Experimental Design

Full-length ovalbumin (OVA) protein was conjugated to high molecular weight and low molecular weight PLGA. Furthermore, once the conjugation was confirmed, TIMP-OVA particles with various controlled loadings of OVA were prepared and characterized.

The progression of experiments is as follows:
1. Synthesis of PLGA-OVA bioconjugates using EDC/NETS chemistry.
2. Solubility testing of resultant PLGA-OVA conjugates in DCM and DMSO to determine suitability for use in particle formation.
3. Determination of the coupling efficiency of PLGA-OVA conjugates thus enabling TIMP-OVA particles to be prepared at various and predetermined Ag loadings.
4. Formulation of TIMP-OVA particles with Ag-loadings that varied from 0 to 150 μg OVA/mg PLGA.
5. Characterization of TIMP-OVA particles by DLS and zeta potential analysis.

TABLE 6

Reagents for synthesis of PLGA-OVA bioconjugates:

| Compound | Molecular weight (g/mol) |
|---|---|
| N-(3-dimethylaminopropyl)-N'-ethylcarbodiimide hydrochloride (EDC) | 191.70 |
| N-hydroxysuccinimide (NHS) | 115.09 |
| Poly(lactide-co-glycolide) (low molecular weight) | 4200 |
| Poly(lactide-co-glycolide) (high molecular weight) | 43478 |
| Ovalbumin grade V (OVA) | 44278 |
| N,N-Diisopropylethylamine (DIPEA) | 129.24 |

OVA contains 20 lysine groups available for covalent modification. Additionally, 14 aspartic acids and 33 glutamic acids are contained within OVA.

Due to the differential solubility of PLGA and OVA, a solvent system to perform the conjugation reactions as well as the appropriate stoichiometric ratio of PLGA to OVA needs to be determined to yield a polymer-Ag conjugate with high solubility in organic solvents such as DCM or DMSO that are necessary for particle fabrication.

To address these questions experimentally, varying the molar ratio of PLGA to OVA from 5 to 20 six-conjugation reactions were performed. A maximum ratio of 20 PLGA:1 OVA was chosen based on the protein structure of OVA where 20 lysine residues are available for coupling with the terminal carboxylic acid group of PLGA. Furthermore, two molecular weights of PLGA were tested for conjugation efficiency and solubility testing. The choice of these reaction conditions was determined to yield the greatest potential to obtain a PLGA-OVA bioconjugate with the necessary Ag contents and solubility requirements. A summary of the reactions conditions is presented in Table 7.

Table 7 shows conditions for Ovalbumin conjugation. 6 reaction conditions were evaluated with the goal to completely solubilize OVA and PLGA in the same solvent system during the reaction. Furthermore, the stoichiometric ratio of PLGA to OVA was varied to yield a final product that was soluble in dimethyl sulfoxide (DMSO).

TABLE 7

Conditions for Ovalbumin conjugation

| Lot no. | Stoichiometric ratio (PLGA:OVA) |
|---|---|
| 03-23-L1 (LMW PLGA) | 5 |
| 03-23-L2 (LMW PLGA) | 10 |
| 03-23-L3 (LMW PLGA) | 20 |
| 03-23-H1 (HMW PLGA) | 5 |
| 03-23-H2 (HMW PLGA) | 10 |
| 03-23-H3 (HMW PLGA) | 20 |

Table 8 shows reaction conditions for Ovalbumin conjugation using low (L) and high (H) molecular weight PLGA. PLGA was prepared at a concentration of 25 mg/mL in DMSO. OVA was prepared at a concentration of 25 mg/mL in MilliQ water. Prior to addition of OVA to the solution containing PLGA, the concentration of PLGA was adjusted to 5 mg/mL to prevent precipitation of the polymer during the conjugation reaction. Furthermore, the solvent ratio was maintained to contain between 15-20 Vol/Vol % MilliQ water in DMSO during the conjugation of PLGA to OVA.

TABLE 8

Reaction conditions for Ovalbumin conjugation

| Reagents | 03-23-L1 | 03-23-L2 | 03-23-L3 |
|---|---|---|---|
| PLGA (25 mg/mL) | 949 µL | 1.89 mL | 3.79 mL |
| EDC (50 mg/mL) | 216.6 µL | 433 µL | 866 µL |
| NHS (25 mg/mL) | 260 µL | 520 µL | 1040 µL |
| DIPEA | 9.84 µL | 19.7 µL | 39.4 µL |
| Additional DMSO | 3.8 mL | 7.594 mL | 15.188 mL |
| OVA (25 mg/mL) | 2 mL | 2 mL | 2 mL |
| Additional water | | | 1.69 mL |

| Reagents | 03-23-H1 | 03-23-H2 | 03-23-H3 |
|---|---|---|---|
| PLGA (25 mg/mL) | 3.92 mL | 3.92 mL | 3.92 mL |
| EDC (50 mg/mL) | 86 µL | 172 µL | 344 µL |
| NHS (25 mg/mL) | 103.5 µL | 207 µL | 414 µL |
| DIPEA | 3.92 µL | 7.84 µL | 15.68 µL |
| Additional DMSO | 15.7 mL | 15.7 mL | 15.7 mL |
| OVA (25 mg/mL) | 0.8 mL | 0.4 mL | 0.2 mL |
| Additional water | 2.69 mL | 3.13 mL | 3.40 mL |

Protocol for PLGA-OVA Conjugation Using Volumes Listed in Table 7.

The following protocol was used. A 60 mL glass scintillation vial containing a magnetic stirbar was prepared. Separately, a 20 mL glass scintillation vial containing the appropriate amount of OVA, additional water, and DIPEA was prepared. The appropriate amount of PLGA dissolved in DMSO and the specified additional DMSO was added to the 60 mL scintillation vial. Under stirring (300-600 RPM) the appropriate amount of EDC was added dropwise to the PLGA solution and stirred for 5 min. Under stirring (300-600 RPM) the appropriate amount of NHS was added dropwise to the EDC-activated PLGA solution and stirred for an additional 10 min. Under stirring (300-600 RPM) the water solution containing OVA and DIPEA was added dropwise to the NHS-activated PLGA solution. (Note that the solutions should be transparent when finished adding this solution to PLGA.) The reaction was allowed to proceed overnight at room temperature. To recover the PLGA-OVA conjugate, the product-containing solution was transferred to a 3500 Da MWCO dialysis membrane and dialyze against 4 L of MilliQ water for 2 days to remove any unreacted EDC/NHS/DIPEA and to remove DMSO. (Note: the product may precipitate in the dialysis bag. Change the water in the dialysis beaker at least 6 times over 2 days.) To collect the product, the precipitate was transferred from the dialysis bag to 50 mL conical centrifuge tubes. The material was centrifuged at 7000×g for 15 min at 4° C. to pellet the product. The product was washed by resuspension and centrifugation twice more. The final product was resuspended in 5 mL of MilliQ water, freeze, and lyophilize for 2 days or until the product is dry.

PLGA-OVA Conjugate Solubility Testing.

To evaluate the solubility of PLGA-OVA conjugates in solvent utilized for particle formulation, approximately 1 mg of conjugate was placed into a 1.5 mL MCT. The results are presented in Table 9. It was identified that conjugates 03-23-L3, and 03-23-H1-3 were soluble in DMSO. This enabled those conjugates to be characterized further.

Table 9 shows solubility testing of PLG-OVA polymer conjugates in DMSO. The precipitate observed after DCM addition is minimal in all cases and does not appear like it would affect particle formation.

TABLE 9

Solubility testing of PLG-OVA polymer conjugates in DMSO

| Polymer conjugate | Comments |
|---|---|
| 03-23-L1 | Not soluble in water, 50:50 DMSO:water, or DMSO |
| 03-23-L2 | Not soluble in water, 50:50 DMSO:water, or DMSO |
| 03-23-L3 | Soluble DMSO. Slight precipitate with DCM added. |
| 03-23-H1 | Soluble DMSO. Slight precipitate with DCM added. |
| 03-23-H2 | Soluble DMSO. Slight precipitate with DCM added. |
| 03-23-H3 | Soluble DMSO. No precipitate with DCM added. |

BCA Assay of PLG-OVA Conjugates to Determine Coupling Efficiency.

Due to the insolubility of 03-23-L1 and 03-23-L2 in DMSO, these samples were not evaluated for protein content.

The protein content present per milligram of polymer was determined using the Pierce BCA protein assay kit (Cat no. 23225). Results are reported in Table 10.

TABLE 10

Concentration of PLGA-OVA conjugates in DMSO and measured protein content using the BCA assay.

| Polymer conjugate | Concentration of PIG-OVA in DMSO used for BCA | Protein content (µg/mg) |
|---|---|---|
| 03-23-L3 | 2 mg/mL | 379 ± 5.5 |
| 03-23-H1 | 5 mg/mL | 141 ± 9.8 |

TABLE 10-continued

Concentration of PLGA-OVA conjugates in DMSO and measured protein content using the BCA assay.

| Polymer conjugate | Concentration of PIG-OVA in DMSO used for BCA | Protein content (µg/mg) |
|---|---|---|
| 03-23-H2 | 10 mg/mL | 59.4 ± 1.9 |
| 03-23-H3 | 20 mg/mL | 38.1 ± 4.7 |

Protocol for Particle Fabrication Using PLGA-OVA Conjugate 03-23-L3

TABLE 11

Formulation parameters for TIMP-OVA with varied Ag loading.

| Formulation | Ag loading | PLG-OVA conjugate | PLGA | Total |
|---|---|---|---|---|
| 1 | 150 | 11.86 mg | 18.14 mg | 30 mg |
| 2 | 50 | 9.88 mg | 65.12 mg | 75 mg |
| 3 | 25 | 9.88 mg | 140.12 mg | 150 mg |
| 4 | 8 | 3.16 mg | 146.84 mg | 150 mg |
| 5 | 4 | 1.58 mg | 148.42 mg | 150 mg |
| 6 | 2 | 0.79 mg | 149.21 mg | 150 mg |
| 7 | 0.5 | 0.2 mg | 149.80 mg | 150 mg |
| 8 | 0 | 0 mg | 150 mg | 150 mg |
| Total | | 37.36 mg | 967.64 mg | 1005 mg |

PLGA at a concentration of 200 mg/mL in DCM was prepared.

PLG-OVA (03-23-L3) at a concentration of 25 mg/mL in DMSO was prepared.

TABLE 12

Formulation specifications for production of TIMP-OVA with various Ag loading.

| Formulation | Ag loading | PLG-OVA conjugate | PLGA | Total | 1% PEMA | 0.5% PEMA |
|---|---|---|---|---|---|---|
| 1 | 150 | 474.4 µL | 907 µL (20 mg/mL) | 30 mg | 3.75 mL | 30 mL |
| 2 | 50 | 395.2 µL | 1628 µL (40 mg/mL) | 75 mg | 5 mL | 75 mL |
| 3 | 25 | 395.2 µL | 1401.2 µL (100 mg/mL) | 150 mg | 10 mL | 150 mL |
| 4 | 8 | 126.4 µL | 734.2 µL (200 mg/mL) | 150 mg | 10 mL | 150 mL |
| 5 | 4 | 63.2 µL | 742.1 µL (200 mg/mL) | 150 mg | 10 mL | 150 mL |
| 6 | 2 | 746.1 µL | 31.6 µL (200 mg/mL) | 150 mg | 10 mL | 150 mL |
| 7 | 0.5 | 8 µL | 749 µL (200 mg/mL) | 150 mg | 10 mL | 150 mL |
| 8 | 0 | 0 µL | 750 µL (200 mg/mL) | 150 mg | 10 mL | 150 mL |
| Total | | 37.36 mg | 967.64 mg | 1005 mg | | |

Procedure for TIMP-OVA Formulation
The following protocol was used.
1.1. Clean the sonicator with acetone, ethanol and then water.
1.2. Pipette the appropriate volume of PLGA as noted in the above table into a 20 mL scintillation vial.
1.3. Pipette the appropriate volume of PLG-OVA as noted in the above table into the same 20 mL scintillation vial from step 1.2.
1.4. Add the appropriate volume of 1% PEMA to the 20 mL scintillation vial containing PLGA and PLG-OVA.
1.5. Sonicate the solution for 30 seconds at 100% amplitude.
1.6. Pour sonicated mixture into the appropriate volume of 0.5% w/v poly(ethylene-alt-maleic anhydride) dissolved in water under stirring at 300 RPM.
1.7. Stir particles overnight to evaporate dichloromethane.
1.8. Prepare solutions of cryoprotectants (sucrose 10 g/25 mL MilliQ water; mannitol 6 g/20 mL MilliQ water). The mannitol solution will take time to dissolve and will require heating. Heat at 70° C. for 15-30 min with frequent vortexing. Upon storage, the mannitol will crystalize out of solution and need to be heated again. The sucrose solution should be soluble at all times. It is acceptable to use premade solutions and heat up the mannitol again.
1.9. Pass particle solution through a 40 μm cell strainer. Distribute the solution into 50 mL falcon tubes.
1.10. Allow particles to chill on ice for 15 min.
1.11. Centrifuge under a relative centrifugal force of 7000×g for 15 minutes at 4° C.
1.12. Aspirate supernatant completely.
1.13. Add 3 mL of 1 M sodium bicarbonate-sodium carbonate buffer to each tube and allow particles to chill on ice for 15 min.
1.14. Resuspend the pellets using a 1 mL pipette or a pipette aid equipped with a 5 mL serological pipette.
1.15. After the pellet is dispersed well (no visible aggregates), add 1 M sodium bicarbonate-sodium carbonate buffer to each tube until total volume is 25 mL.
1.16. Centrifuge under a relative centrifugal force of 7000×g for 15 minutes at 4° C.
1.17. Aspirate supernatant completely.
1.18. Add 3 mL of 1 M sodium bicarbonate-sodium carbonate buffer to each tube and allow particles to chill on ice for 15 min.
1.19. Resuspend the pellets. After the pellet is dispersed well, add 1 M sodium bicarbonate-sodium carbonate buffer to each tube until the total volume is 25 mL.
1.20. Centrifuge under a relative centrifugal force of 7000×g for 15 minutes at 4° C.
1.21. Aspirate supernatant completely.
1.22. Add 3 mL of MilliQ water into the tube and allow particles to chill on ice for 15 min.
1.23. Resuspend the pellet. After the pellet is dispersed well, add additional MilliQ water until the particle concentration is between 4-8 mg/mL. Assuming that the recovery of particle will be 40%.
1.24. Homogeneously disperse the particles in the water.
1.25. Pass particle solution through a 40 μm cell strainer.
1.26. Prepare sample tubes for lyophilization, 2 mL tubes for particle aliquoting. Pre-mass at least 1-3 of those tubes to determine the amount of particles per tube.
1.27. Pipette 800 μL of the particle solution into each tube and save at least 200 μL of particle solution for characterization by DLS/Zeta analysis in a 1.5 mL microcentrifuge tube (only need to use 20 μL of particle sample in MilliQ water to perform DLS/Zeta analysis).
1.28. For each sample tube that gets cryoprotectant, mix 100 μL of the sucrose and 100 μL of the mannitol solutions together and add to the particles with mixing by pipette. The total volume per tube will now be 1 mL. The concentration of cryoprotectant will be 4% w/v sucrose and 3% w/v Mannitol.
1.29. Freeze all samples, including the ones with no cryoprotectant, except for the sample to be used for DLS/Zeta analysis (put in 4 deg. Fridge for characterization later) in the −80 freezer for at least 5 hr.
1.30. Lyophilize the samples for 1-2 days.

TABLE 13

Measurement of the size and zeta potential of TIMP-OVA particles

| Particle | Size (nm) | Zeta potential (mV) | PDI |
| --- | --- | --- | --- |
| TIMP-OVA150 | 847.7 ± 33.4 | −60.4 ± 1.2 | 0.710 |
| TIMP-OVA50 | 464.0 ± 12.8 | −28.6 ± 0.2 | 0.410 |
| TIMP-OVA25 | 340.6 ± 6.2 | −29.1 ± 0.9 | 0.190 |
| TIMP-OVA8 | 405.8 ± 8.8 | −34.7 ± 0.9 | 0.270 |
| TIMP-OVA4 | 386.2 ± 2.5 | −33.0 ± 0.6 | 0.260 |
| TIMP-OVA2 | 518.5 ± 3.4 | −34.9 ± 0.9 | 0.370 |
| TIMP-OVA0.5 | 391.1 ± 3.8 | −35.6 ± 0.4 | 0.230 |
| PLG blank (IMP) | 286.9 ± 0.4 | 39.7 ± 0.3 | 0.130 |

Evaluation of the Biological Activity of TIMP-OVA Conjugates Using an In Vitro Treg Induction Assay.

The objective of this study was to determine the effect of antigen loading in polymer conjugate TIMP-OVA on the induction of naïve CD4+ T cells (OTII) to regulatory T cells (CD4+CD25+Foxp3+).

Experimental Groups:

| Particle | Ag or particle dose | TGF-b dose |
| --- | --- | --- |
| TGF ONLY | 0 ng/mL | 2 ng/mL |
| OVA$_{323-339}$ | 100 ng/mL | 2 ng/mL |
| OVA | 100 ng/mL | 2 ng/mL |
| OVA | 1000 ng/mL | 2 ng/mL |
| OVA | 10000 ng/mL | 2 ng/mL |
| TIMP(OVA) 02-204 10 μg/mg | 300 μg/mL | 2 ng/mL |
| TIMP-OVA$_{323-339}$ 8 μg/mg | 300 μg/mL | 2 ng/mL |
| TIMP-OVA 150 μg/mg | 5, 10, 75, 150, 300 μg/mL | 2 ng/mL |
| TIMP-OVA 25 μg/mg | 5, 10, 75, 150, 300 μg/mL | 2 ng/mL |
| TIMP-OVA 8 μg/mg | 5, 10, 75, 150, 300 μg/mL | 2 ng/mL |
| TIMP-OVA 2 μg/mg | 5, 10, 75, 150, 300 μg/mL | 2 ng/mL |
| PLG blank (IMP) | 300 μg/mL | 2 ng/mL |

The amount of OVA antigen per mL of media was calculated based on the dose of TIMP-OVA and the loading amount of OVA protein per mg of TIMP. The bolded and italicized cells in Table 14 indicate the particles that were tested in the Treg experiment. Importantly, the amount of Ag delivered per well covered significant breadth from 0 ng/mL to 45000 ng/mL.

TABLE 14

Antigen calculation per mL in each well treated with TIMP-OVA

| Particle loading (μg/mg) | Concentration (μg/mg) | | | | | |
|---|---|---|---|---|---|---|
| | 0 | 5 | 10 | 75 | 150 | 300 |
| 0 | 0 | 0 | 0 | 0 | 0 | 0 |
| *2* | 0 | 10 | 20 | 150 | 300 | 600 |
| 4 | 0 | 20 | 40 | 300 | 600 | 1200 |
| *8* | 0 | 40 | 80 | 600 | 1200 | 2400 |
| 25 | 0 | 125 | 250 | 1875 | 3750 | 7500 |
| 50 | 0 | 250 | 500 | 3750 | 7500 | 15000 |
| *150* | 0 | 750 | 1500 | 11250 | 22500 | 45000 |

Bone Marrow Derived Dendritic Cell Culture (Following the Method of Lutz et al.)

The preparation of BMDCs was performed as described previously. DCs were prepared by culturing bone marrow cells obtained from C57BL/6 mice. Bone marrow cells were flushed from the tibias and femurs using a needle-equipped syringe. The recovered cells were incubated in ACK lysis buffer to lyse red blood cells. The bone marrow cells were cultured in RPMI-1640 medium supplemented with 10% fetal bovine serum, 100 units/mL penicillin, 100 mg/mL streptomycin, 2 mM L-glutamine, 50 uM 2-mercaptoethanol, and 20 ng/mL granulocyte-macrophage colony-stimulating factor. The culture medium was changed on days 3, 6, and 8. The cells were ready to use on day 10.

Cell Isolation and In Vitro Treg Induction Assay

CD4+CD25-foxp3− T cells were isolated from the spleen of OT-II mice (B6.Cg-Tg(TcraTcrb)425Cbn/J, Jackson Laboratory, Bar Harbor, Me.) using a naïve CD4+ T cell isolation kit (Miltenyi Biotec, San Diego, Calif.). The assay was carried out in RMPI media supplemented with 10% fetal bovine serum, 1% pen/strep, and non-essential amino acids. APCs ($2 \times 10^4$/well) were seeded into 96 well round bottom cell culture plates and treated with soluble $OVA_{323-339}$ peptide (100 ng/mL) or particles with various Ag-loadings or particle doses and co-cultured with $2 \times 10^4$/well naïve T cells in the presence of 2 ng/mL TGFβ. After 4 days of co-culture, the T cells were collected and stained for CD4, CD25, and Foxp3 and analyzed using the Cyan cytometer.

CONCLUSIONS

PLGA-OVA bioconjugates were successfully synthesized using EDC/NHS (carbodiimide) chemistry. Using the BCA assay, the protein content per mg of PLGA-OVA bioconjugate was determined. The amount of protein per mg was dependent on the polymer molecular weight as well as the stoichiometric ratio of PLGA:OVA. The PLGA-OVA conjugate with the highest protein content was 03-23-L3 and the lowest was 03-23-H3.

As a starting point, TIMP-OVA particles were formulated with various Ag loadings from 0 μg/mg to 150 μg/mg using the PLGA-OVA conjugate 03-23-L3 due to its high protein loading capability. TIMP-OVA particles prepared using 03-23-L3 displayed sizes measured by DLS between 300 nm and 850 nm. TIMP-OVA 150 μg/mg displayed an unusually high PDI greater than 0.7. The zeta potentials of TIMP-OVA ranged between −30 and −60 mV.

Preliminary in vitro testing using a Treg induction assay that characterized the ability of various TIMP-OVA particles to induce regulatory T cells in the presence of TGFb indicated that the protein remained active following conjugation and TIMP formulation. It should be noted that TIMP-OVA did not appear to be as effective as $TIMP-OVA_{323-339}$ or TIMP(OVA) particles with similar loadings.

While specific embodiments of the invention have been described and illustrated, such embodiments should be considered illustrative of the invention only and not as limiting the invention as construed in accordance with the accompanying claims.

All patents, applications and other references cited herein are incorporated by reference in their entireties.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11510996B2). An electronic copy of the "Sequence Listing" will also be available from the USPTO upon request and payment of the fee set forth in 37 CFR 1.19(b)(3).

What is claimed is:

1. A composition comprising one or more antigens covalently attached to a polymeric carrier particle comprising a poly(lactide-co-glycolide) (PLG) particle, a polylactic acid (PLA) particle or a poly(lactic-co-glycolic acid) particle, wherein said one or more antigens are encapsulated in said particle by covalent attachment to the internal particle surfaces, and, optionally wherein said antigens are further attached to the surface of the polymeric particle, and wherein the zeta potential of the particle is from −80 to −30 mV and the particle has an average diameter between about 0.3 μm to about 5 μm.

2. The composition of claim 1, wherein the composition further comprises an unconjugated carrier polymer.

3. The composition of claim 1, wherein the particle comprises a co-polymer having a molar ratio from about 50:50, 80:20 to about 100:0.

4. The composition of claim 1, wherein the particle comprises poly(lactic-co-glycolic acid).

5. The composition of claim 1, wherein the particle has an average diameter of between about 400 to about 800 nanometers.

6. The composition of claim 1, wherein said one or more antigens comprises an autoimmune antigen, an antigen expressed on a tissue to be transplanted into a subject, an enzyme for enzyme and/or protein replacement therapy, or an allergen.

7. The composition of claim 1, wherein said one or more antigens comprises one or more epitopes.

8. The composition of claim 7, wherein the one or more epitopes is associated with an allergy, an autoimmune disease, an enzyme used in enzyme and/or protein replacement therapy, lysosomal storage disease, or an inflammatory disease or disorder.

9. The composition of claim 1, wherein said one or more antigens is directly covalently bound to said carrier particle.

10. A method of inducing antigen-specific tolerance in a subject comprising: administering to said subject an effective amount of a composition of claim 1.

11. The method of claim 10, wherein said administering is performed to treat or prevent a disease or condition.

12. The method of claim 11, wherein said disease or condition is selected from the group consisting of: an autoimmune disease, a lysosomal storage disease, an enzyme deficiency, a protein deficiency, inflammatory disease, an allergy, transplantation rejection, and a hyperimmune response.

13. The method of claim 10, wherein the carrier particle comprises a polystyrene particle, a carboxylated polystyrene particle, a polaxamer stabilized polypropylene sulfide particle, a poly(lactide-co-glycolide) (PLG) particle, a polylactic acid (PLA) particle, or a poly(lactic-co-glycolic acid) particle.

14. The method of claim 10, wherein the carrier particle comprises a poly(lactic-co-glycolic acid) particle.

15. The method of claim 10, wherein said composition is administered intravenously.

16. A method of inducing regulatory T cells comprising treating said T cells with an effective amount of a composition of claim 1, wherein the particle size is greater than 80 nm.

17. A process for the preparation of the composition of claim 1 which forms a tolerizing immune modifying particle (TIMP) having one or more antigens encapsulated within said particle by covalent attachment to the internal particle surfaces, said process comprising:
    a) covalently linking one or more carrier polymers with one or more antigens to form carrier polymer-antigen conjugates; and
    b) contacting the carrier polymer-antigen conjugates with a solution under conditions effective to form the TIMP, wherein the TIMP having one or more antigens encapsulated in the TIMP by covalent attachment to the internal particle surfaces, is formed.

18. The process of claim 17, wherein the particle comprises a poly(lactide-co-glycolide) (PLG) particle, a polylactic acid (PLA) particle or a poly(lactic-co-glycolic acid) particles.

* * * * *

UNITED STATES PATENT AND TRADEMARK OFFICE
CERTIFICATE OF CORRECTION

PATENT NO. : 11,510,996 B2
APPLICATION NO. : 16/064528
DATED : November 29, 2022
INVENTOR(S) : Ryan Pearson et al.

It is certified that error appears in the above-identified patent and that said Letters Patent is hereby corrected as shown below:

On the Title Page

At item (73), Line 2, "COMPANY" should be -- COMPANY, --.

In the Claims

At Column 73, Line 20, "polaxamer" should be -- poloxamer --.

At Column 74, Line 24, "particles." should be -- particle. --.

Signed and Sealed this
Twenty-third Day of May, 2023

Katherine Kelly Vidal
*Director of the United States Patent and Trademark Office*